United States Patent
Yaffe et al.

(10) Patent No.: US 9,320,750 B2
(45) Date of Patent: Apr. 26, 2016

(54) COMPOSITIONS AND METHODS OF TREATMENT OF DRUG RESISTANT CANCERS

(71) Applicant: Massachusetts Institute of Technology, Cambridge, MA (US)

(72) Inventors: Michael B. Yaffe, Somerville, MA (US); Michael Jungho Lee, Cambridge, MA (US); Paula T. Hammond, Newton, MA (US); Stephen W. Morton, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 255 days.

(21) Appl. No.: 13/869,012

(22) Filed: Apr. 23, 2013

(65) Prior Publication Data

US 2014/0011759 A1 Jan. 9, 2014

Related U.S. Application Data

(60) Provisional application No. 61/646,034, filed on May 11, 2012.

(51) Int. Cl.
*A61K 9/127* (2006.01)
*A61K 31/704* (2006.01)
*C07H 15/252* (2006.01)
*A61K 31/517* (2006.01)
*A61K 45/06* (2006.01)

(52) U.S. Cl.
CPC ............... *A61K 31/704* (2013.01); *A61K 9/127* (2013.01); *A61K 31/517* (2013.01); *A61K 45/06* (2013.01); *C07H 15/252* (2013.01)

(58) Field of Classification Search
None
See application file for complete search history.

(56) References Cited

U.S. PATENT DOCUMENTS

| | | | |
|---|---|---|---|
| 6,120,751 A * | 9/2000 | Unger | 424/9.51 |
| 2007/0197568 A1 | 8/2007 | Bunn et al. | |
| 2010/0189683 A1 | 7/2010 | Holmlund et al. | |
| 2011/0301209 A1 | 12/2011 | Zaknoen et al. | |

OTHER PUBLICATIONS

Isakoff et al., "Triple Negative Breast Cancer: Role of Specific Chemotherapy Agents" Cancer Journal (2010) vol. 16 No. 1 pp. 53-61.*
Shi et al., "The epidermal growth factor tyrosine kinase inhibitor AG1478 and erlotinib reverse ABCG2-mediated drug resistance" Oncology Reports (2008) vol. 21 pp. 483-489.*
Baselga et al., "Phase II Multicenter Study of the Antiepidermal Growth Factor Receptor Monoclonal Antibody Cetuximab in Combination With Platinum-Based Chemotherapy in Patients With Platinum-Refractory Metastatic and/or Recurrent Squamous Cell Carcinoma of the Head and Neck" Journal of Clinical Oncology (2005) vol. 23 No. 25 pp. 5568-5577.*
Nagashima et al., "BCRP/ABCG2 levels account for the resistance to topoisomerase I inhibitors and reversal effects by gefitinib in non-small cell lung cancer" Cancer Chemotherapy and Pharmacology (2006) vol. 58 pp. 594-600.*
Abeloff, M.D. et al., Chapter 95: Cancer of the Breast, in Abeloff's Clinical Oncology, Fourth Edition, pp. 1875-1943, Churchill Livingstone Elsevier (2008).
Albeck, J.G. et al., Modeling a Snap-Action, Variable-Delay Switch Controlling Extrinsic Cell Death, PLoS Biology, 6(12):2831-2852 (2008).
Balko, J.M. et al., Gene expression patterns that predict sensitivity to epidermal growth factor receptor tyrosine kinase inhibitors in lung cancer cell lines and human lung tumors, BMC Genomics, 7:289-302 (2006).
Carey, L.A. et al., TBCRC 001: EGFR inhibition with cetuximab added to carboplatin in metastatic triple-negative (basal-like) breast cancer, Supplement to Journal of Clinical Oncology, 2008 ASCO Annual Meeting Proceedings, 26(155):1009 (2008).
Carpenter, A.E. et al., CellProfiler: image analysis software for identifying and quantifying cell phenotypes, Genome Biology, 7(10):R100-R100.11 (2006).
Chou, T-C. et al., Quantitative Analysis of Dose-Effect Relationshiios: The Combined Effects of Mutliple Drugs or Enzyme Inhibitors, Advances in Enzyme Regulation, 22:27-55 (1984).
Corkery, B. et al., Epidermal growth factor receptor as a potential therapeutic target in triple-negative breast cancer, Annals of Oncology, 20:862-867 (2009).
Dent, R. et al., Triple-Negative Breast Cancer: Clinical Features and Patterns of Recurrence, Clinical Cancer Research, 13:4429-4434 (2007).
Diaz, R. et al., Antitumor and antiangiogenic effect of the dual EGFR and HER-2 tyrosine inhibitor lapatinib in a lung cancer model, BMC Cancer, 10:188 (2010).
Dowben, R.M., General Physiology: A Molecular Approach, pp: 142-143, Harper & Row Publishers (1969).

(Continued)

*Primary Examiner* — Eric Olson
(74) *Attorney, Agent, or Firm* — Foley Hoag LLP

(57) ABSTRACT

Time-staggered inhibition of EGFR, in combination with DNA damaging agents, is a useful therapeutic strategy for treating cancers, particularly drug resistant cancers such as a subset of triple-negative tumors, particularly those with high basal levels of phosphorylated EGFR. The staggered therapy was also demonstrated to be applicable to other types of tumors, especially lung cancers, which contain either high levels of phosphorylated wild-type EGFR or mutations within EGFR itself. EGFR inhibition dramatically sensitizes cancer cells to DNA damage if the drugs are given sequentially, but not simultaneously. The first drug must be administered in a dosage and for a period of time sufficient for the dynamic network rewiring of an oncogenic signature maintained by active EGFR signaling to unmask an apoptotic process that involves activation of caspase-8.

10 Claims, 44 Drawing Sheets

(56) References Cited

OTHER PUBLICATIONS

Ekins, S. et al., Pathway Mapping Tools for Analysis of High Content Data, Methods in Molecular Biology, 356:319-350 (2007).

Fitzgerald, J.B. et al., Systems biology and combination therapy in the quest for clinical efficacy, Nature Chemical Biology, 2(9):458-466 (2006).

Gaudet, S. et al., A Compendium of Signals and Responses Triggered by Pro-death and Prosurvival Cytokines, Molecular & Cellular Proteomics, 4:1569-1590 (2005).

Hanahan, D. et al., The Hallmarks of Cancer, Cell, 100 57-70 (2000).

Harper, J.W. et al., The DNA Damage Response: Ten Years After, Molecular Cell, 28(5):739-745 (2007).

Helfrich, B.A. et al., Antitumor Activity of the Epidermal Growth Factor Receptor (EGFR) Tyrosine Kinase Inhibitor Gefitinib (ZD1839, Iressa) in Non-Small Cell Lung Cancer Cell Lines Correlates with Gene Copy Number and EGFR Mutations but not EGFR Protein Levels, Clinical Cancer Research, 12:7117-7125 (2006).

Janes, K.A. et al., A Systems Model of Signaling Identifies a Molecular Basis Set for Cytokine-Induced Apoptosis, Science, 310:1646-1653 (2005).

Janes, K.A. et al., Cytokine-Induced Signaling Networks Prioritize Dynamic Range over Signal Strength, Cell, 135:343-354 (2008).

Kang, N. et al., Inhibition of EGFR signaling augments oridonin-induced apoptosis in human laryngeal cancer cells via enhancing oxidative stress conicident with acticiation of both the intrinsic and extrinsic apoptotic pathways, Cancer Letters, 294:147-158 (2010).

Kim, R., Recent Advances in Understanding the Cell Death Pathways Activated by Anticancer Therapy, Cancer, 103(8):1551-1560 (2005).

Lichter, A.S. et al., Recent Advances in Radiation Oncology., New England Journal of Medicine, 332(6):371-379 (1995).

Lopez, J.P. et al., Gefitinib Inhibition of Drug Resistance to Doxorubicin by Inactivating ABCG2 in Thyroid Cancer Cell Lines, Archives of Otolaryngology—Head & Neck Surgery, 133(10):1022-1027 (2007).

MacBeath, G., Protein microarrays and proteomics, Nature Genetics Supplement, 32:526-532 (2002).

Mizushiman, N. et al., Methods in Mammalian Autophagy Research, Cell, 140:313-326 (2010).

Montesano, R. et al., Test for Malignant Transformation of Rat Liver Cells in Culture: Cytology, Growth in Soft Agar, and Production of Plasminogen Activator, Journal of the National Cancer Institute, 59(6):1651-1658 (1977).

Morgillo, F. et al., Antitumor activity of bortezomib in human cancer cells with acquired resistance to anti-epidermal growth factor receptor tyrosine kinase inhibitors, Lung Cancer, 71:283-290 (2011).

Neve, R.M. et al., A collection of breast cancer cell lines or the study of functionally distinct cancer subtypes, Cancer Cell, 10:515-527 (2006).

Pawson, T. et al., Network medicine., FEBS Letters, 582:1266-1270 (2008).

Perou, C.M. et al., Molecular portraits of human breast tumours, Nature, 406:747-752 (2000).

Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).

Sachs, K. et al., Casual Protein-Signaling Networks Derived from Multiparameter Single-Cell Data, Science, 308:523-529 (2005).

Sapi, E. et al., Ets-2 Transdominant Mutant Abolishes Anchorage-independent Growth and Macrophage Colony-stimulating Factor-stimulated Invasion by BT20 Breast Carcinoma Cells, Cancer Research, 58:1027-1033 (1998).

Schechter, A.L. et al., The *neu* oncogene: an *erb-B*-related gene encoding a 185,000-M$_r$ tumour antigen, Nature, 312:513-516 (1984).

Sengupta, S. et al., Temporal targeting of tumor cells and neovasculature with a nanoscale delivery system, Nature, 436:568-572 (2005).

Sevecka, M. et al., State-based discovery: a multidimensional screen for small-molecule modulators of EGF signaling, Nature Methods, 3(10):825-831 (2006).

Slamon, D.J. et al., Human Breast Cancer: Correlation of Relapse and Survival with Amplification of the HER-2/neu Oncogene, Science, 235:177-182 (1987).

Sordella, R. et al., Gefitinib-Sensitizing EGFR Mutations in Lung Cancer Activate Anti-Apoptotic Apoptotic Pathways, Science, 305:1163-1167 (2004).

Subramanian, A. et al., Gene set enrichment analysis: A knowledge-based approach for interpreting genome-wide expression profiles, Proceedings of the National Academy of Sciences of the United State of America, 102(43):15545-15550 (2005).

Sun, T. et al., Activation of Multiple Proto-oncogenic Tyrosine Kinases in Breast Cancer via Loss of the PTPN12 Phosphatase, Cell, 144:703-718 (2011).

Turner, J.G. et al., ABCG2 expression, function, and promoter methylation in human multiple myeloma, Blood, 108(12):3881-3889 (2006).

Winer, E.P. et al., Optimizing Treatment of "Triple-Negative" Breast Cancer. SABCS 2007: Improving Outcomes in Advanced and Meta—static Breast Cancer, http://www.medscape.org/viewarticle/569483 (2007).

Woehlecke, H. et al., Reversal of breast cancer resistance protein-mediated drug resistance by tryprostatin A, International Journal of Cancer, 107:721-728 (2003).

Wood, E.R. et al., A Unique Structure for Epidermal Growth Factor Receptor Bound to GW572016 (Lapatinib): Relationships among Protein Conformation, Inhibitor Off-Rate, and Receptor Activity in Tumor Cells, Cancer Research, 64:6652-6659 (2004).

Yoon, C-H. et al., Activation of p38 Mitogen-Activated Protein Kinase is Required for Death Receptor-Independent Caspase-8 Activation and Cell Death in Response to Sphingosine, Molecular Cancer Research, 7(3):361-370 (2009).

International Search Report for PCT/US13/37868, 3 pages (Sep. 6, 2013).

Milano, G. et al., EGFR-targeting drugs in combination with cytotoxic agents: from bench to bedside, a contrasted reality, British Journal of Cancer, 99:1-5 (2008).

Written Opinion for PCT/US13/37868, 10 pages (Sep. 6, 2013).

\* cited by examiner

A
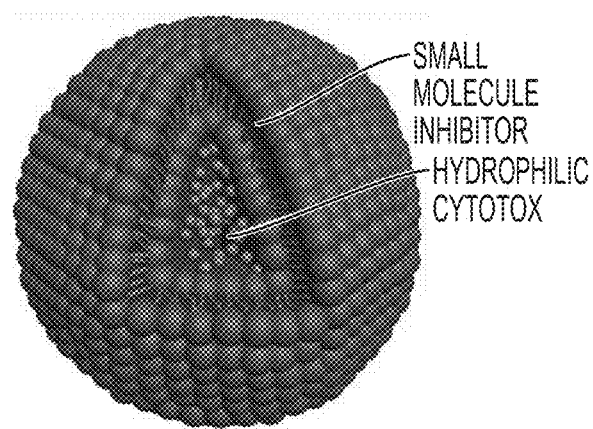
- SMALL MOLECULE INHIBITOR
- HYDROPHILIC CYTOTOX
B
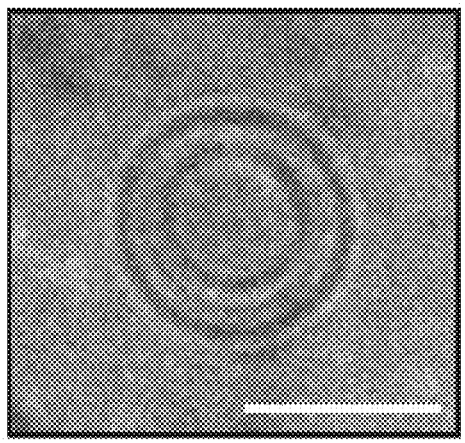
SCALE BARS REPRESENTATIVE OF 100nm
C
| LIPOSOMAL FORMULATION | MEAN z-avg $d_h$ (nm) | PDI | ζ-POTENTIAL (mV) | CYTOTOX:INHIBITOR MASS LOADING RATIO |
|---|---|---|---|---|
| DE | 136 | 0.13 | -29 | 2.5:1 |
| D | 97 | 0.13 | -29 | N/A |
FIG. 22A-22C

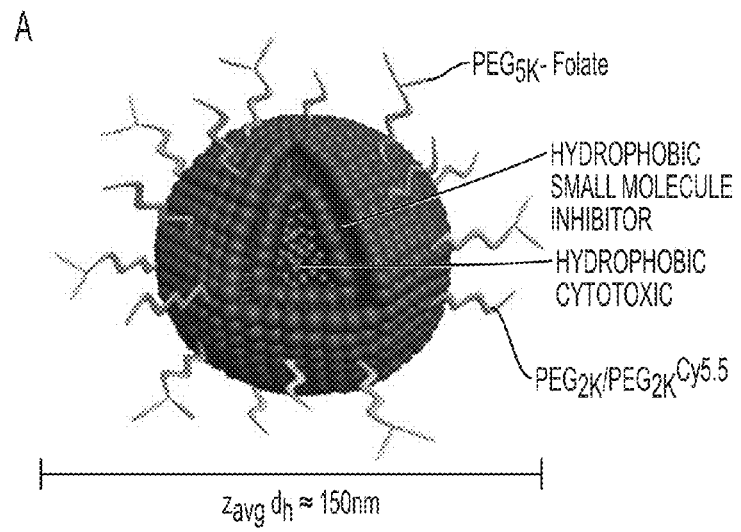
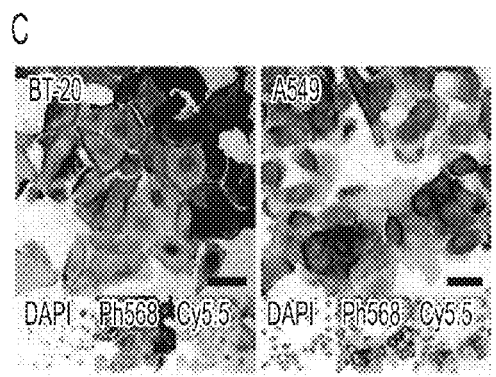
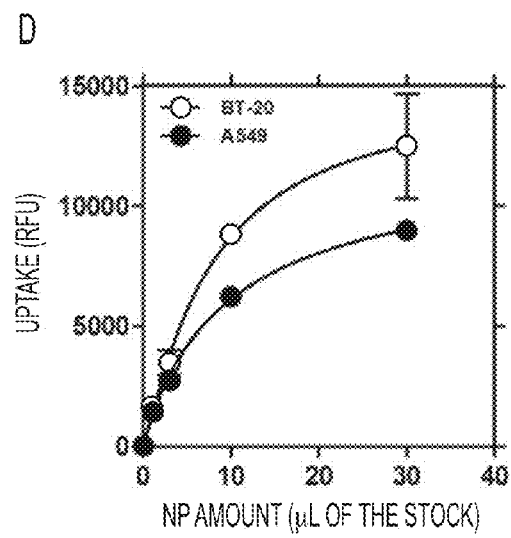
FIG. 24A-24D

A

B

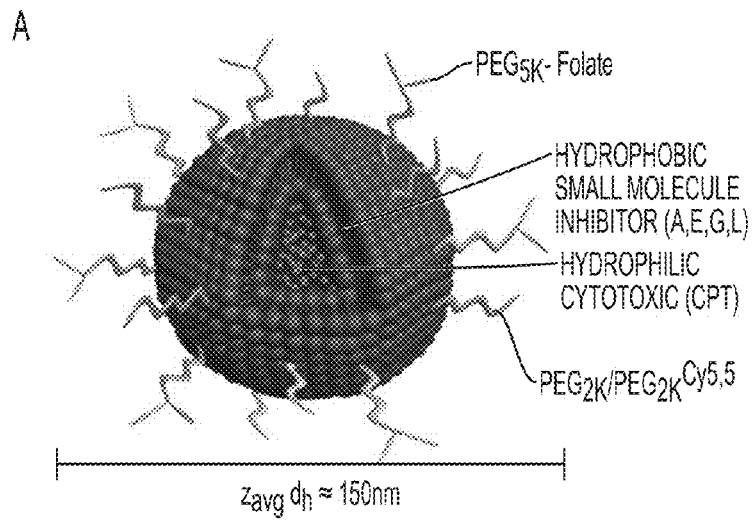
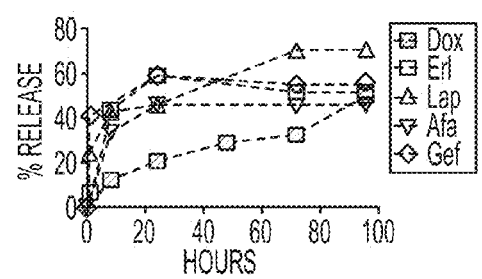
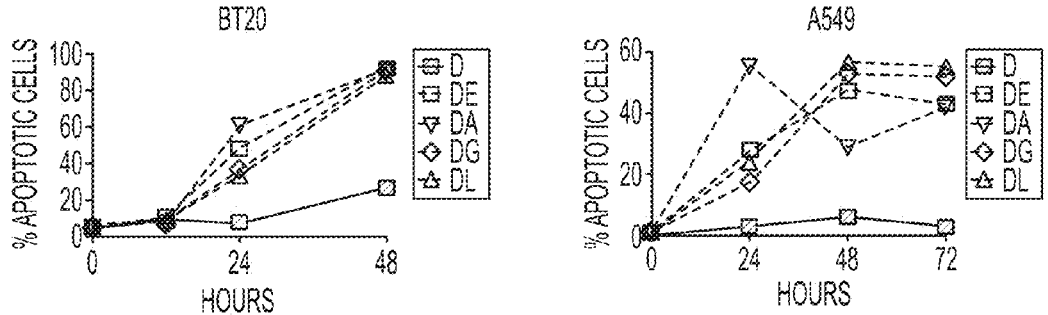
FIG. 27A-27D

COMPOSITIONS AND METHODS OF TREATMENT OF DRUG RESISTANT CANCERS

CROSS-REFERENCE TO RELATED APPLICATION

This application claims priority to and the benefit of, and incorporates herein by reference in its entirety, U.S. Provisional Patent Application No. 61/646,034, filed May 11, 2012.

STATEMENT REGARDING FEDERALLY SPONSORED RESEARCH OR DEVELOPMENT

This invention was made with Government Support under Agreement CA112967, GM68762, and ES015339 awarded to Michael B. Yaffe by the National Institutes of Health and DOD fellowship BC097884 to Michael J. Lee, and Grant No. DGE-1122374 awarded to Stephen W. Morton by the National Science Foundation. The Government has certain rights in the invention.

FIELD OF THE INVENTION

The present invention is generally in the field of methods and compositions talking a specific pathway for the treatment of cancer.

BACKGROUND OF THE INVENTION

Standard therapies for the treatment of human malignancies typically involve the use of chemotherapy or radiation therapy, which function by damaging DNA in both normal and cancerous cells (Lichter, A. S., and Lawrence, T. S. (1995). Recent Advances in Radiation Oncology. N. Engl. J. Med. 332, 371-379). Our growing understanding of this process suggests that the DNA damage response (DDR) functions as part of a complex network controlling many cellular functions, including cell cycle, DNA repair, and various forms of cell death (Harper, J. W., and Elledge, S. J. (2007). The DNA Damage Response: Ten Years After. Mol. Cell 28, 73 745). The DDR is highly interconnected with other pro-growth and prodeath signaling networks, which function together to control cell fate in a nonlinear fashion due to multiple levels of feedback and cross-talk. Thus, it is difficult to predict a priori how multiple, often conflicting, signals will be processed by the cell, particularly by malignant cells in which regulatory networks often exist in atypical forms. Predicting the efficacy of treatment and the optimal design of combination therapy will require a detailed understanding of how the DDR and other molecular signals are integrated and processed, how processing is altered by genetic perturbations commonly found in tumors, and how networks can be "rewired" using drugs individually and in combination (Sachs, K., Perez, 0., Pe'er, D., Lauffenburger, D. A., and Nolan, G. P. (2005). Causal protein-signaling networks derived from multiparameter single-cell data. Science 308, 523-529).

In many forms of breast cancer, aberrant hormonal and/or growth factor signaling play key roles in both tumor induction and resistance to treatment (Hanahan, D., and Weinberg, A. A. (2000). The Hallmarks of Cancer Cell 100, 57-70). Moreover, the identification of molecular drivers in specific breast cancer subtypes has led to the development of more efficacious forms of targeted therapy (Schechter, A. L., Stern, D. F., Vaidyanathan, L., Decker, S. J., Drebin, J. A., Greene, M. I., and Weinberg, A. A. (1984). The Neuoncogene: An Erb-B-Related Gene Encoding a 185,000-Mr Tumour Antigen. Nature 312, 513-516.; Slamon, D. J., Clark, G. M., Wong, S. G., Levin, W. J., Ullrich, A., and McGuire, W. L. (1987). Human Breast Cancer: Correlation of Relapse and Survival with Amplification of the HER-2/neuoncogene. Science 235, 177-182). In spite of these advances, there are currently no targeted therapies and no established molecular etiologies for triple-negative breast cancers (TNBC), which are a heterogeneous mix of breast cancers defined only by the absence of estrogen receptor (ER) or progesterone receptor (PR) expression and lack of amplification of the HER2 oncogene (Perou, C. M., Serlie, T., Eisen, M. S., van de Rijn, M., Jeffrey, S. S., Rees, C. A., Pollack, J. R., Ross, D. T., Johnsen, H., Akslen, L. A., et al. (2000). Molecular Portraits of Human Breast Tumours Nature 406, 747-752). Patients with TNBCs have shorter relapse-free survival and a worse overall prognosis than other breast cancer patients; however, they tend to respond, at least initially, to genotoxic chemotherapy (Dent, A., Trudeau, M., Pritchard, K. l., Hanna, W. M., Kahn, H. K., Sawka, C. A., Lickley, L. A., Rawlinson, E., Sun, P., and Narod, S. A. (2007). Triple-Negative Breast Cancer: Clinical Features and Patterns of Recurrence. Clin. Cancer Res. 13, 4429-4434). Triple-negative patients generally do well if pathologic complete response is achieved following chemotherapy. When residual disease exists, however, the prognosis is typically worse than for other breast cancer subtypes (Abeloff, M., Wolff, A., Weber, B., Zaks, T., Sacchini, V., and McCormick, B. (2008). Cancer of the Breast. In Abeloffs Clinical Oncology, M. Abeloff, J. Armitage, J. Niederhuber. M. Kastan, and W. McKenna, ads. (Maryland Heights, Mo.: Churchill Livingstone), pp. 1875-1944). Thus, identifying new strategies to enhance the initial chemosensitivity of TNBC cells may have substantial therapeutic benefit.

SUMMARY OF THE INVENTION

Time-staggered inhibition of EGFR, in combination with DNA damaging agents, is a useful therapeutic strategy for treating cancers, particularly drug resistant cancers such as a subset of triple-negative tumors, particularly those with high basal levels of phosphorylated EGFR. The staggered therapy was also demonstrated to be applicable to other types of tumors, especially lung cancers, which contain either high levels of phosphorylated wild-type EGFR or mutations within EGFR itself.

EGFR inhibition dramatically sensitizes cancer cells to DNA damage if the drugs are given sequentially, but not simultaneously. The first drug must be administered in a dosage and for a period of time sufficient for the dynamic network rewiring of an oncogenic signature maintained by active EGFR signaling to unmask an apoptotic process that involves activation of caspase-8. The enhanced sensitivity to damaging agents requires sustained inhibition of EGFR from modulation of an oncogene-driven transcriptional network as indicated schematically in the model shown in FIG. 7G. It is activity of the EGFR pathway, rather than EGFR expression per se, that determines whether time-staggered inhibition will result in synergistic killing. These observations also indicate that EGFR phosphorylation is a useful biomarker of response to time-staggered inhibition in at least some tumor types that are EGFR driven, including some TNBCs and lung cancers.

As shown by the examples, by manipulating the interface between growth factor signaling pathways and DNA damage signaling pathways in tumor cells, pretreatment of a subset of TNBCs with Epidermal Growth Factor Receptor (EGFR) inhibitors can markedly synergize their apoptotic response to DNA-damaging chemotherapy through dynamic rewiring of oncogenic signaling networks and unmasking of suppressed proapoptotic pathways.

VIP score>1 indicates important x variables that predict y responses, whereas signals with VIP scores<0.5 indicate unimportant x variables. (8 and C) Model-generated predictions of apoptosis with (blue) or without (red) caspase-8 activation 8 hr after the indicated treatments in BT-20 (B) and 453 (C). (D and E) Western blot verifying caspase-8 knockdown in BT-20 (D) and 453 (E). (F and G) Measured apoptosis 8 hr after the indicated treatment in cells expressing control RNA or caspase-8 siRNA. (F) BT-20. (G) 453. In both (F) and (G), apoptotic values represent mean response±SD from both siRNAs, each in duplicate.

FIGS. 7A-7G. Time-Staggered Inhibition of EGFR Signaling Enhances Apoptotic Response in a Subset of TNBC Cells and Other EGFR-Driven Cells (A) Panel of TNBC cell lines with a wide range of EGFR expression levels. Heatmap for total EGFR expression, p-EGFR(Y1173), percent apoptosis, apoptosis relative to DOX alone, and casp-8 cleavage. Apoptosis measured as in FIG. 1. EGFR and p-EGFR expression are measured by western blotting of untreated cells. Cleaved casp-8 measured by western blot 8 hr after exposure to DOX. (B) EGFR activity, but not total EGFR expression, is correlated with sensitivity to time-staggered ERL→DOX combination. Fold enrichment of cell death observed in E→D relative to DOX alone regressed against total EGFR or p-EGFR (pY1173) as measured in untreated cells for the ten TNBC cell lines shown in FIG. 7A. R2 reports the linear fit for each trend line. (C) BT-20 cells grown as xenograft tumors in nude mice. Arrow indicates intraperitoneal administration of indicated drugs. Mean tumor volume±SEM shown from four animals for each treatment condition. (D-F) Time-staggered inhibition of HER2 in HER2-driven breast cancer cells (D) or EGFR in lung cancer cells (E and F) causes casp-8 activation and sensitization to DOX. Apoptosis measured as in FIG. 1 for cells exposed to a control RNA (left in each panel) or siRNA targeting casp-8 (right in each panel). Caspase-8 activation was monitored 8 hr after doxorubicin treatment (c-casp8. shown beneath the controlRNA plots). Validation of caspase-8 knockdown is shown below the CASP8 siRNA plots. Mean values±SD of three experiments are shown. (D) HER2-overexpressing MDA-MB-453 cells treated with Japatinib. (E and F) lung cancer cells treated with erlotinib. (E) NCI-H1650. (F) A-549. (G) A model for enhanced cell death after DNA damage by chronic EGFR inhibition in triple-negative breast cancer cells.

Figure 8A:
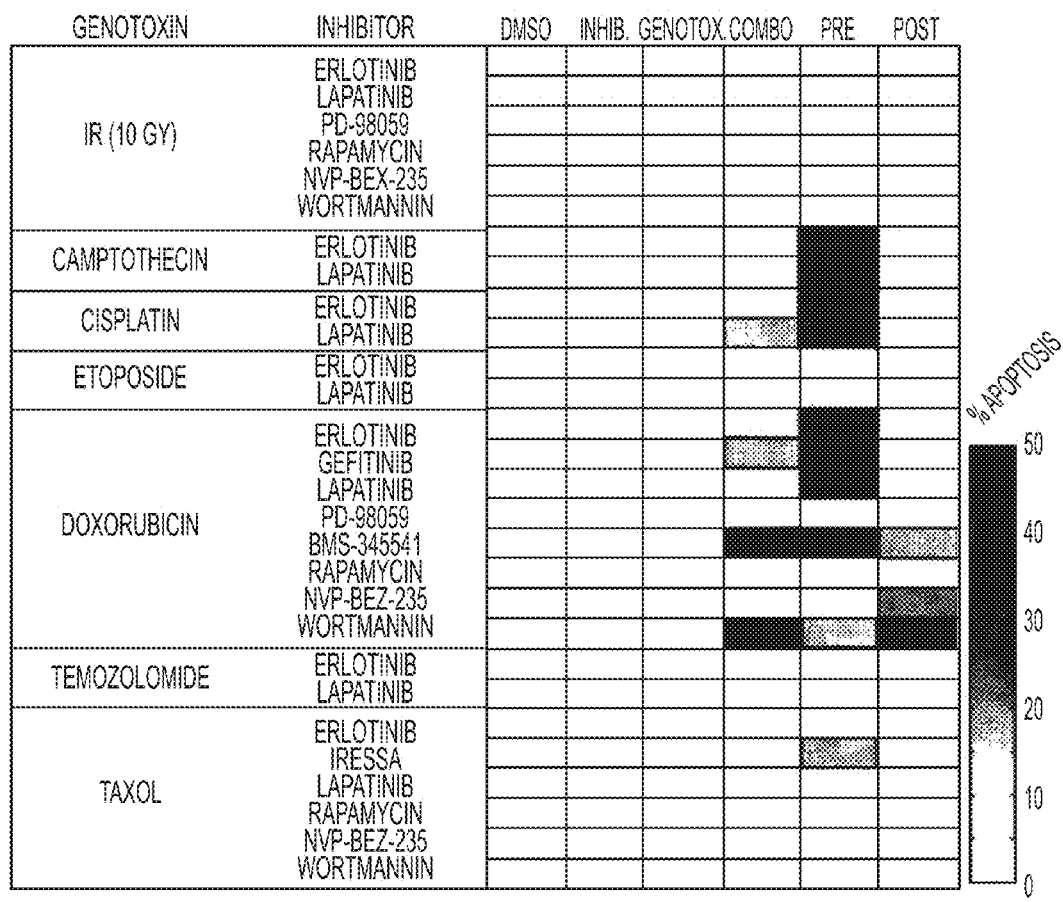
Figures 8B, 8C:
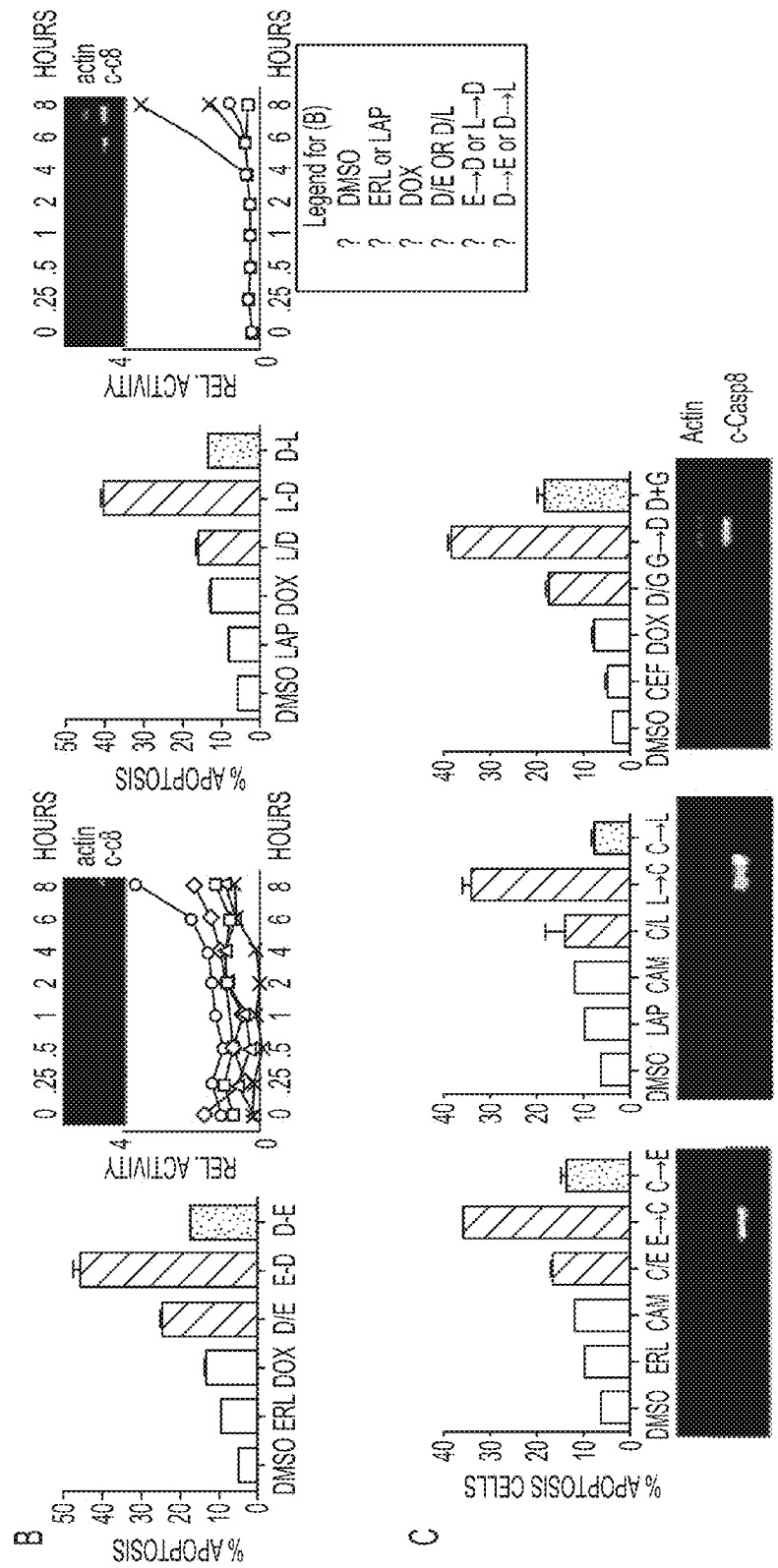

FIGS. 8A-8C. Combination Screen for Synergistic Drug Combinations in Triple-Negative BT-20 Cells, Related to FIG. 1. (A) An initial screen of various genotoxins combined with targeted inhibitors was performed in triple-negative BT-20 cells. Dose, time, and combination timing were first screened using the CellTiterGlo assay (Promega). Shown in heatmap form are apoptotic responses for each combination. For each, "PRE" refers to addition of the inhibitor 24 hr before genotoxin; "POST" refers to addition of the inhibitor 4 hr after the genotoxin; "COMBO" refers to the addition of 2 drugs at the same time. All data were collected 8 hr after genotoxin exposure as described in FIG. 1. (B and C) Apoptotic response of BT-20 cells 8 hr after exposure to genotoxin (as in FIG. 1) shown in detail for synergistic combinations. Mean values±SD of 3 independent experiments, each performed in duplicate, are shown. (B) Apoptotic response and cleaved caspase-8 time course for doxorubicin combined with erlotinib (left) or doxorubicin combined with lapatinib (right). Caspase-8 cleavage was measured by western blot at indicated times after drug exposure (blot for "ED" or "L_,D" shown). Caspase-8 activity was quantified relative to baseline activation for each treatment at 8 time points, as indicated in the legend. The quantification strategy is described in the supplementary methods section. (C) Apoptotic response for additional synergistic combinations. (left) Camptothecin (CAM)±erlotinib (ERL); (middle) CAM±lapatinib (LAP); (right) doxorubicin (DOX)±gefitinib (GEF). Caspase-8 cleavage 8 hr after genotoxin exposure as monitored by western blot is shown below for each treatment. Detailed analysis of other synergistic combinations are shown in FIG. 1 (DOX/ERL) and Figure S7 (DOX/LAP).

FIGS. 9A-9D. Efficacy of Erlotinib-Doxorubicin Combination Requires Time-Staggered Doxing, Related to FIG. 2(A and B) Lysates made from BT-20 cells treated with erlotinib for the indicated times were probed for EGFR activity (p-EGFR Y1173) (A) or activity of signals downstream of EGFR, like ERK (B). Sample blots shown and quantified from 3 independent experiments (data are mean±SO). (C) Increased erlotinib concentration, rather than time-staggered dosing, does not enhance sensitivity to doxorubicin in triple-negative BT-20 cells. Apoptotic response was measured 8 hr after drug exposure by flow cytometry, as described in FIG. 1. In all cases, 10 11M doxorubicin was co-administered with the indicated amount of erlotinib. These data further support the hypothesis that specific timing/network rewiring is necessary for enhanced sensitivity to doxo-rubicin. See also FIG. 2. (D) Detailed analysis of cell cycle 24 hr following drug treatment. Timing of drug combination does not significantly alter cell cycle profile. Cells were treated as in FIG. 1, and cell cycle progress monitored using flow cytometry. Data are mean values±SD of three independent experiments.

FIGS. 10A-10E. Differentially Expressed Genes following Erlotinib Treatment in BT-20, MDA-MB-453, and MCF7 Cells, Related to FIG. 3. Differentially expressed genes (DEGs) following erlotinib treatment for various amounts of time as indicated. Cells were treated with 1-DiiM erlotinib and RNA extracted for microarray analysis. The cut-off for differential gene expression was greater than a 2-fold change and a p-value less than 0.05 (genes that meet both criteria are colored red). P-values were calculated using LIMMA (Smyth, 2004). B score (a measure of significance) is the log of the odds (lads) of differential expression. Data are from three biological replicates. (A-C) Time course of erlotinib treatment in BT-20 cells. (D) 24 hr erlotinib treatment in MDA-MB-453 cells. (E) 24 hr ertotinib treatment in MCF7 cells. Expression data can be found in the GEO repository under the accession number GSE30516. See also FIG. 3.

FIGS. 11A-11F A Conceptual Overview of PLS Modeling for the EGFR Inhibition/DNA Damage Data Set, Related to FIG. 4. (A) An expanded signaling-response network. This network includes canonical components of the DNA damage response, together with components in general stress response pathways, and growth factor, cytokine and cell death pathways. Specific targets selected for measurement were based on prior knowledge of the pathway, or by identification of the target protein as a differentially expressed gene in our microarray studies (see also FIGS. 3 and 10). Briefly, from the identified list of approximately 2000 DEGs, GSEA and GeneGO were used to identify pathways, molecular signatures, or processes that were significantly altered by long-term erlotinib exposure. Within each pathway, proteins were chosen for study that either 1) function as critical signaling nodes in that particular pathway, or 2) are thought to regulate DNA damage responses or cell death. 1000 antibodies to over 200 targets of interest were tested in both reverse phase protein lysate array format and quantitative western blot format using a panel of 90 control lysates generated from 30 treatment conditions in 3 different cell lines. Antibodies to targets of interest that were validated to be high fidelity (band at appropriate size; report predicted changes in expression across control lysate panel) were included for computational analysis if treatment-dependent or cell line dependent differences were observed. Proteins whose activity and/or expression were directly measured are boxed in white. BCL2 FAM denotes the BCL2 family members BIM, and BID. (B) Simplified explanation of PLS modeling. In this hypothetical example, "signaling space" is comprised of 3 signaling components. Experimental observations (blue) could be plotted with respect to time (as traditionally done and shown in top panel) or plotted in signaling space (as shown below). Dimensionality reduction can be further achieved by identification of principal components, which are defined as latent axes that maximally capture the variance in the dataset Projection of the original signaling metrics into principal component space is a useful tool for identifying the contribution of each signal to the variance in the dataset. A similar process can be performed on the quantitative measurements of cellular response, and signaling vectors can be regressed against response vectors to identify co-variation between signals and responses. The organization of signaling vectors in signaling space is determined by methods analogous to those used to cluster gene microarray data. In more complex examples, individual signaling metrics may first be concatenated into a single signaling vectors based on co-linearity. This concatenated signaling space can be further dimensionally reduced as described above. The data space was comprised of 7,560 signaling vectors and 630 response vectors, which were derived from over 47,000 independent measurements. See also FIG. 4. (C-F) Examples of raw cell response data. (Autophagy was monitored using automated fluorescence microscopy of cells expressing mCherry-EGFP-LC3B, and quantified using the CeiiProfiler image analysis software (G) Cell viability was quantified using CellTiterGlo. (H and I) Cell cycle and apoptosis were quantified by flow cytometry as described in FIGS. 1 and 2.

FIGS. 12A-12L PCA and PLS Models Resolve Cell Type-Specific and Treatment-Specific Variance in Molecular Signals, Related to FIG. 5 (A) Principal component analysis on signaling measurements from BT-20, MDA-MB-453, and MCF7 cells. Color scheme from FIG. 5 is simplified to highlight different cell lines (BT-20 in red, MDA-MB-453 in black, and MCF7 in blue) and treatment-specific responses. Rather than highlighting all six different treatments, those that received doxorubicin in any combination are labeled "+DOX" (open squares) and those treatments that did not receive doxorubicin are labeled "−DOX" (closed circles). "−DOX" treatments include erlotinib, DMSO, and all 0 hr treatment time points. These data highlight that cell line specific information was captured in PC1, while treatment specific information was captured in PC2. NOTE: PC3 did not capture a statistically significant level of variance. (B-E) Partial least-squares regression analysis of covariance between signaling measurements and cellular fates from BT-20, MDA-MB-453, and MCF7 cells. Simplified color scheme used as described in panels A (8) Principal Component 1 (PC1) versus PC2. (C) PC1 versus PC3 (D) PC2 versus PC3. (E) Three-dimensional plot highlighting cell-line specific and response specific clusters. These PLS generated data highlight that the co-variance between signals and responses is largely cell type dependent. See also FIG. 5. (F-L) Measured versus predicted responses for each of the seven cellular responses monitored in the BT-20 cell line model.

FIGS. 13A-13F Validation of PL5 Model-Generated Predictions, Related to FIG. 6 (A-.C) Additional validation of model-generated predictions for targets predicted to have strong, moderate, or negligible influence on apoptosis. Apoptosis was measured 8 hr after the indicated treatment in cells expressing either control RNA (scrambled RNA) or siRNA against indicated target. Data shown are the mean values±SD from two separate siRNAs against the indicated target, each performed in duplicate. (A) siRNA targeted against caspase-S (strong positive covariance with apoptosis in BT-20 and MDA-MB-453 cells; no predicted role in MCF7 cells). (B) siRNA targeted against Beclin-1 (moderate negative covariance with apoptosis in BT-20 cells, but no predicted role in MDA-MB-453 or MCF7 cells). (C) siRNA targeted against RIP! (no predicted role in BT-20 or MDA-MB-453 cells. strong negative co-variance in MCF7 cells). (D-F) Validation of knockdown for caspase-6 (D), Beclin-1 (E), and RIP1 (F). Shown for each are control RNA (C) and two different siRNAs (1 and 2). Percent knockdown (% k.d.) is calculated relative to control RNA. Actin shown as a loading control (red band in all cases).

Figures 1A, 1B, 1C, 1D:
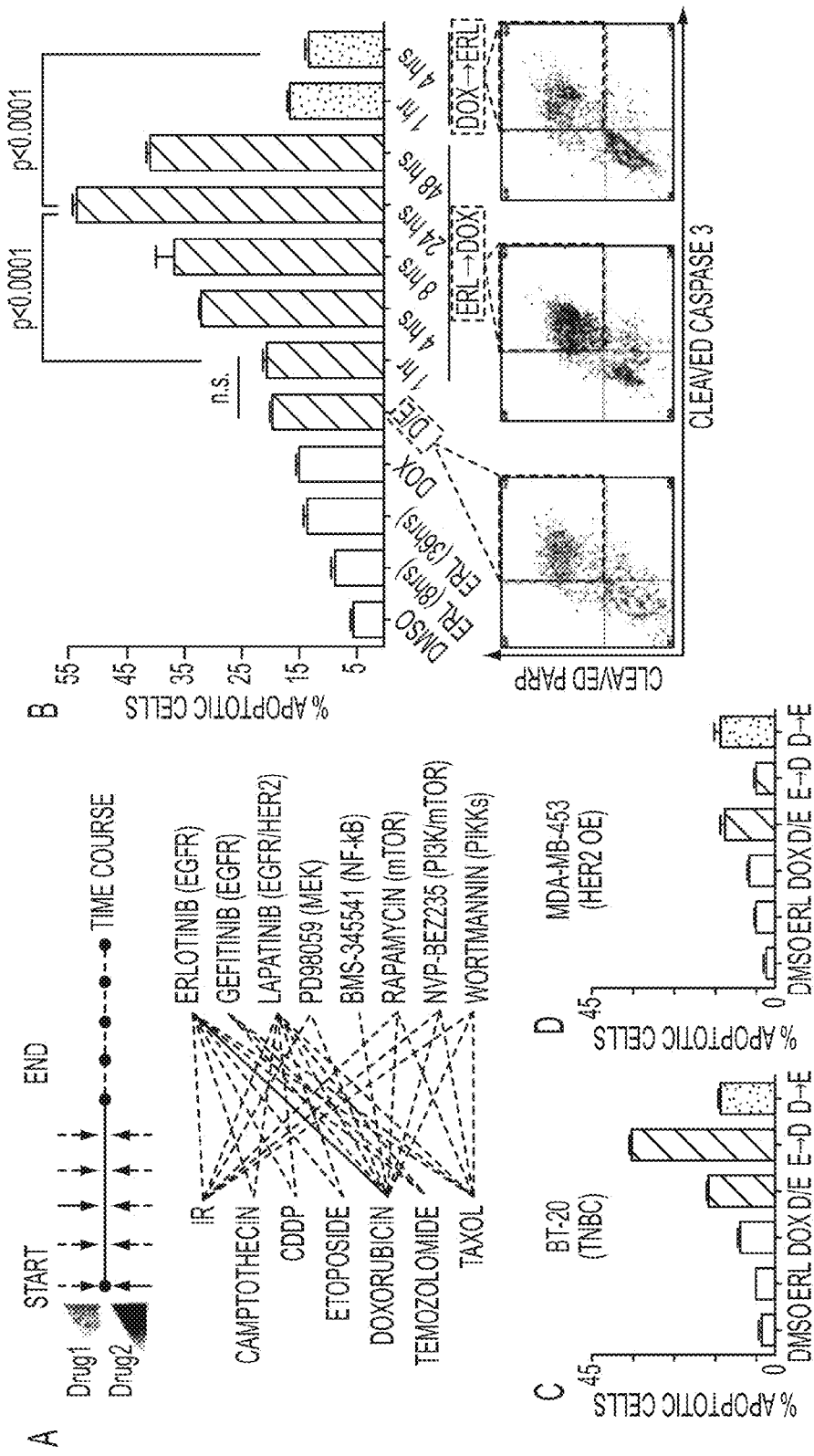
FIGS. 1A-1I. A Screen for Novel Combination Treatment Reveals Dosing Schedule-Dependent Efficacy for Killing TNBC Cells (A) Schematic of combinations tested. Seven genotoxic drugs and eight targeted signaling inhibitors were tested in pair-wise combinations, varying dose, order of presentation, dose duration, and dosing schedule. (B) Apoptosis in BT-20 cells. Cleaved-caspase 3/cleaved-PARP double-positive cells were quantified using flow cytometry (bottom). In cells treated with DMSO, erlotinib (ERL), or doxorubicin (DOX), apoptosis measurements were performed 8 hr after drug exposure or at the indicated times. D/E, ERL-.DOX, and DOX-ERL refer to DOX and ERL added at the same time, ERL given at the indicated times before DOX, and DOX given at the indicated times before ERL, respectively. For each, apoptotic measurements were made 8 hr after the addition of DOX. Erlotinib and doxorubicin were used at 10 μM. Mean values±SD of three independent experiments, each performed in duplicate, are shown (top). (C-F) Apoptosis in different subtypes of breast cancer. Apoptosis was measured as in (B). (D and E) E-.D and D-.E refer to DOX and ERL added at the same time, ERL given 24 hr before DOX, and DOX given 4 hr before ERL, respectively. Data are mean values±SD of three independent experiments. (G) Dose-response profiles of erlotinib/doxorubicin drug combinations. Apoptosis was measured as in (B). Drugs were added at a 1:1 ratio, and combination index (CI) was calculated according to the Chou-Talalay method. (H) Knockdown of EGFR in BT-20 cells measured 48 hr after addition of the indicated siRNA by immunoblotting (left). EGFR expression relative to "no RNA" control is quantified on right. (I) Apoptosis in BT-20 cells±EGFR knockdown measured as in (B). Scrambled RNAi shown as control. Data shown are the mean±SD of both siRNAs, each, performed in biological duplicate.
Figures 1E, 1F, 1G, 1H, 1I:
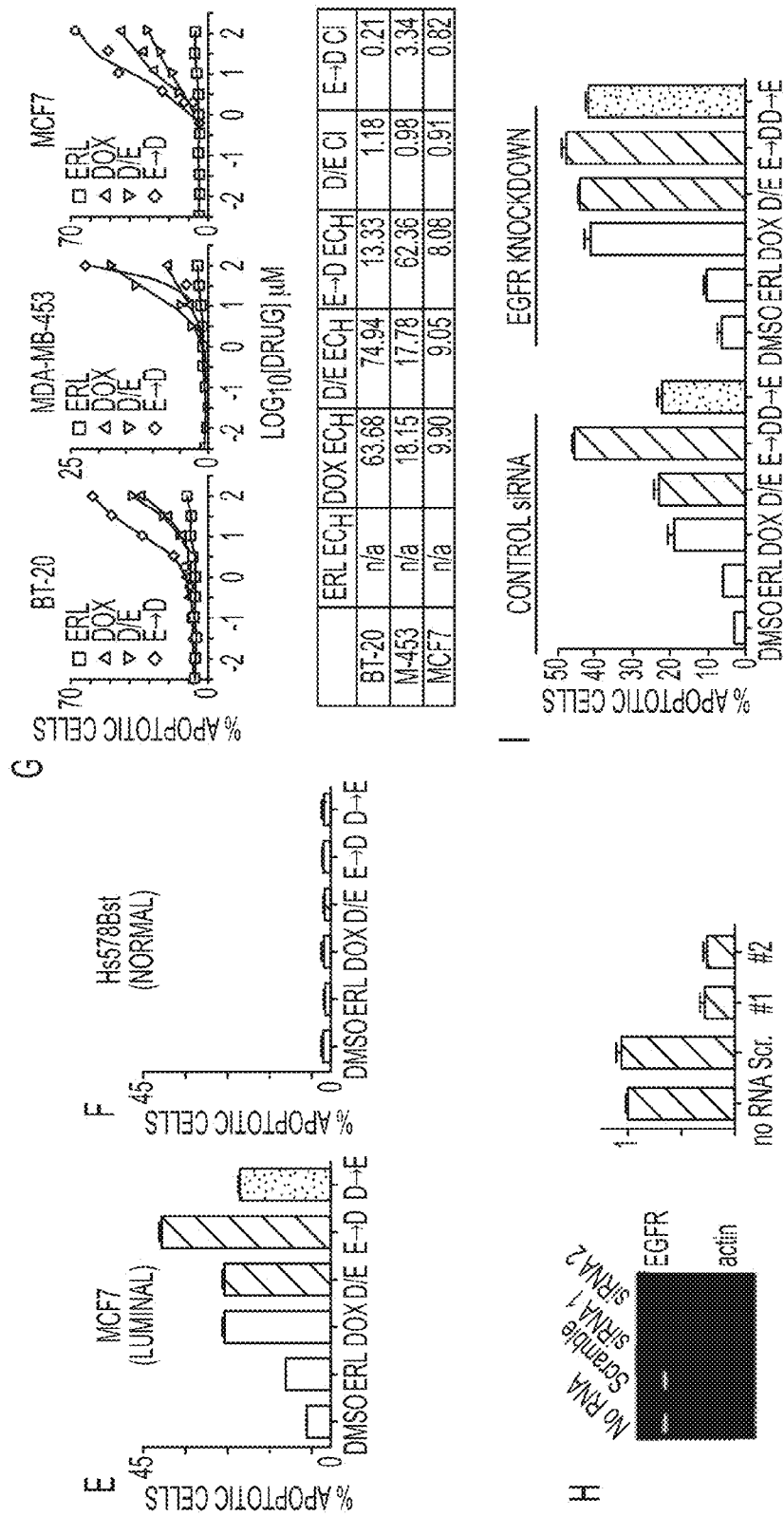

FIGS. 14A-14D—Apoptotic Response across a Panel of Breast Cancer Cell Lines Reveals a Correlation between EGFR Activity and Sensitivity to Erlotinib-Ooxorubicin Combinations in Triple-Negative Cells, Related to FIG. 7 (A) Apoptosis was measured by flow cytometry 8 hr after treatment as described in FIG. 1. For each protein, basalsubtype (A or B) and p53 status are reported (according to Neve, R. M., Chin, K., Fridlyand, J., Yeh, J., Baehner, F. L., Fevr, T., Clark, L., Bayani, N., Coppa, J. P., Tong, F., et al. (2006). A collection of breast cancer cell lines for the study of functionally distinct cancer subtypes. Cancer Cell 10, 515-527). For p53, protein status is shown in parentheses. EGFR protein levels and EGFR activity (p-EGFR) were determined by quantitative western blot with an antibodies directed against EGFR or phospho-EGFR (pY1173). EGFR or p-EGFR values reported are relative to maximum in the cell line panel. For EGFR, shown in parentheses are data reported in Neve et al. (2006) when applicable. Chou-Talalay combination index (CI) was used to assess synergy. Mean±SO are shown for three independent experiments. (B) Dose response profiles for cell lines in which synergistic interactions were found. Data were collected as described in FIG. 1G. Mean values shown from three independent experiments. (C) Time-staggered inhibition of HER2 in HER2 driven breast cancer cells in the presence or absence of caspase-8. Apoptosis was measured in HER2 over-expressing BT-474 cells 8 hr after doxorubicin exposure as described in FIG. 1. Caspase-8 cleavage was measured by western blot following the indicated treatments (shown beneath the Control RNA histogram), and caspase-8 knockdown was confirmed using a total caspase-8 antibody (shown beneath the GASPS siRNA histogram). Percent knockdown (% k.d.) was calculated relative to expression in cells exposed to a control RNA. Lapatinib (LAP; a duel specificity EGFR/HER2 inhibitor.) was used to inhibit HER2. Although synergy was observed for all LAP/DOX combinations in HER2 overexpressing cells, the enhanced sensitivity observed in the time-staggered condition (L→D) relative to the other combinations (D/L or D→L) was mediated by caspase-8 activation as validated by siRNA knockdown. Mean±50 are shown for three independent experiments. (D) Time-staggered EGFR inhibition in lung cancer cells with high EGFR activity in the presence or absence of caspase-8. Apoptosis was measured in NCI-H358 cells, and data were collected and are presented as in (C).

Figure 15:
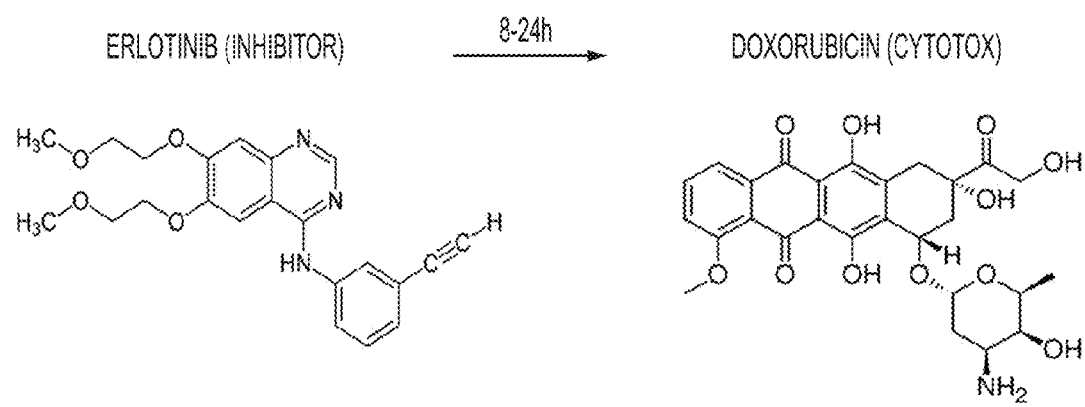

FIG. 15 Structures of two exemplary drugs, Erlotinib and Doxorubicin.

Figure 16:
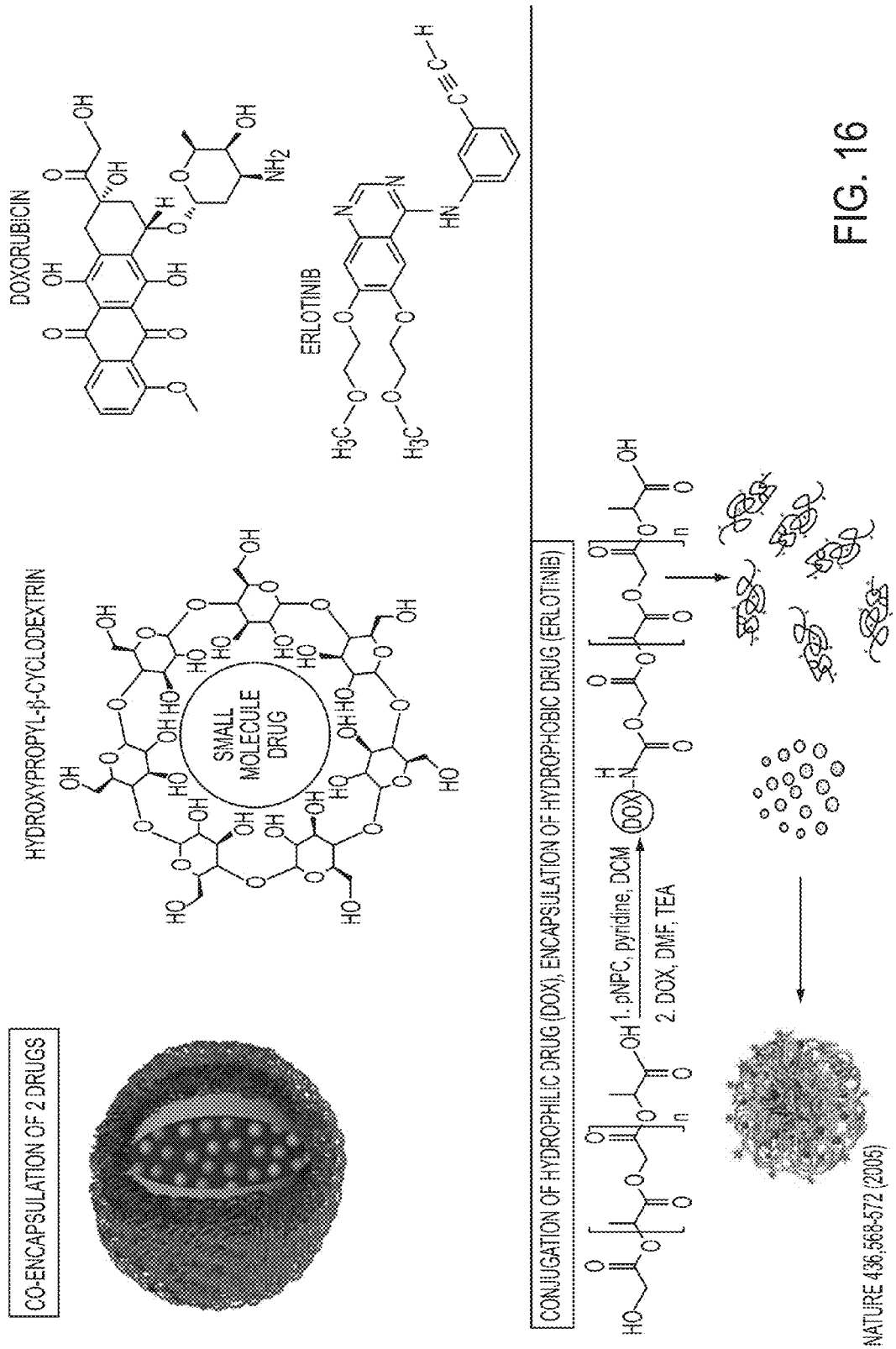

FIG. 16 illustrates 1) co-encapsulation of two drugs (top); and b) conjugation of hydrophilic (Dox) and encapsulation of hydrophobic drug (erlotinib) (bottom). See details in "Temporal targeting of tumor cells and neovasculature with a nanoscale delivery system" by Sengupta et al., Nature 436, 568-572 (2005), the contents of which are incorporated here by reference.

Figure 17:
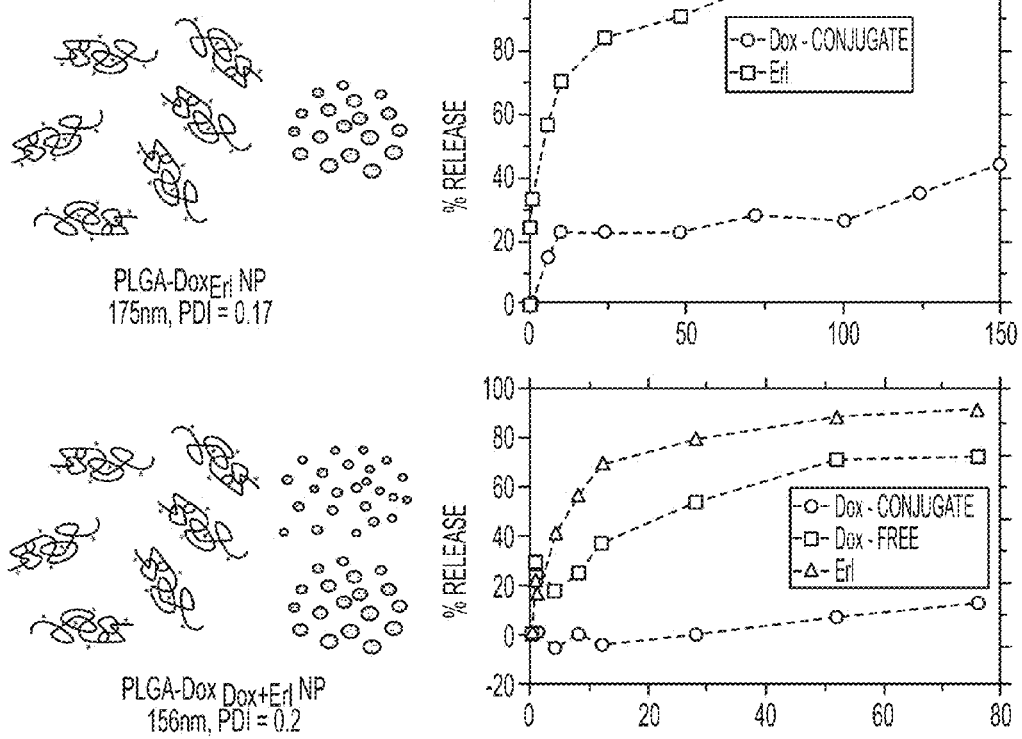

FIG. 17 Drug release characteristics of two exemplary particles.

Figure 18:
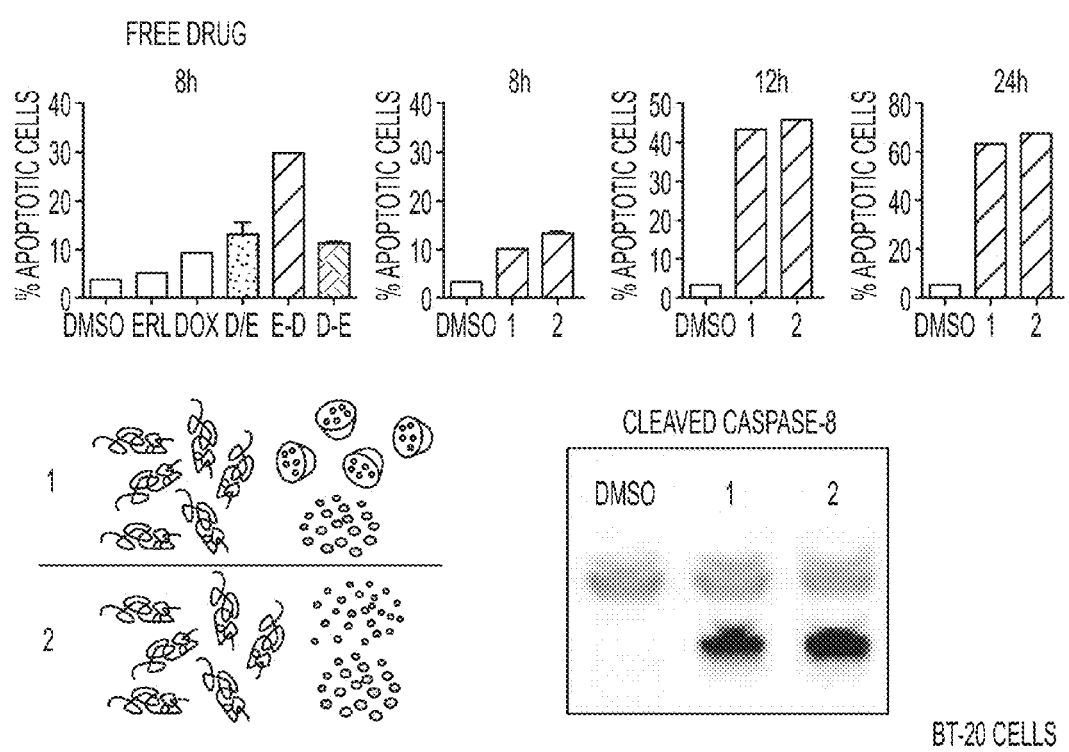

FIG. 18 Cell apoptotic response showing 1) loading issue with erlotinib (consistent theme with PLGA); 2) variability in loading efficiency; and 3) size of particles.

Figure 19:
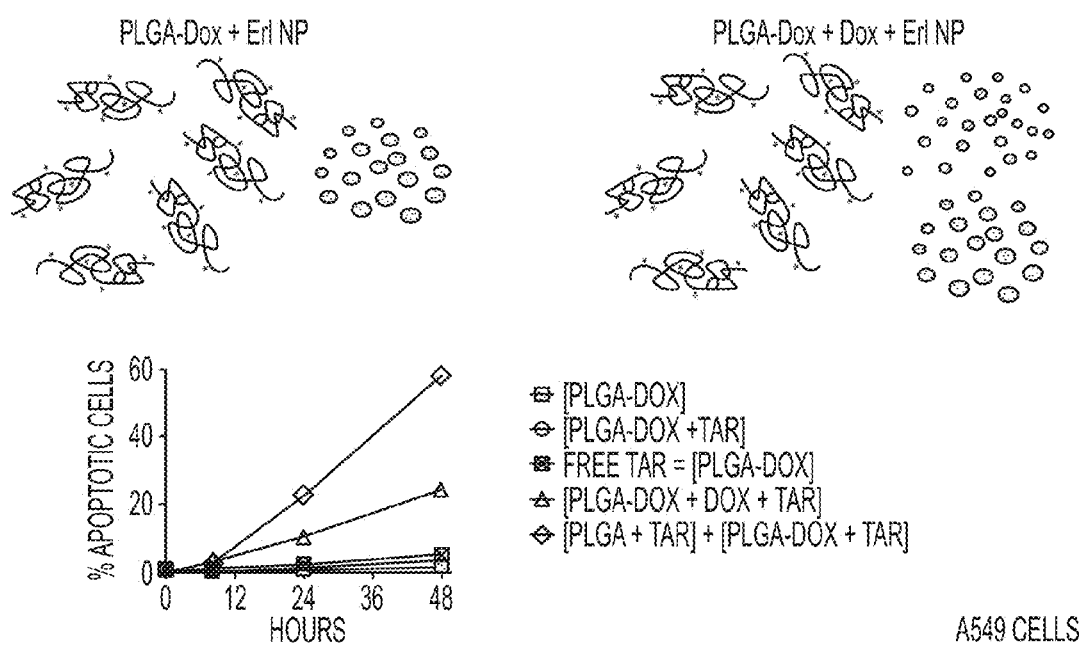

FIG. 19 Cell apoptotic response showing 1) Dox-conjugate release being too slow to be therapeutic alone; 2) one vs. two particles; and 3) inhibitor loading issue (1:5-10 ratio of Erl: Dox).

Figure 20:
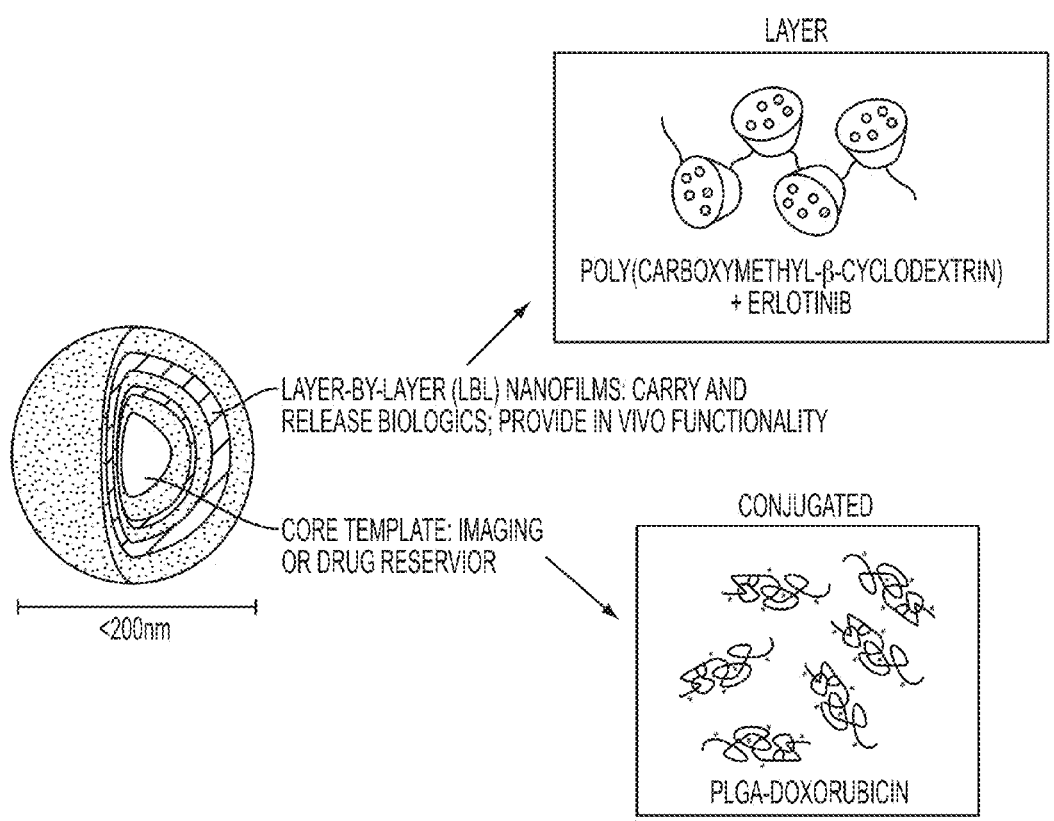

FIG. 20 schematic of using LBL films for enhanced loadings and staged release of drugs.

Figure 21:
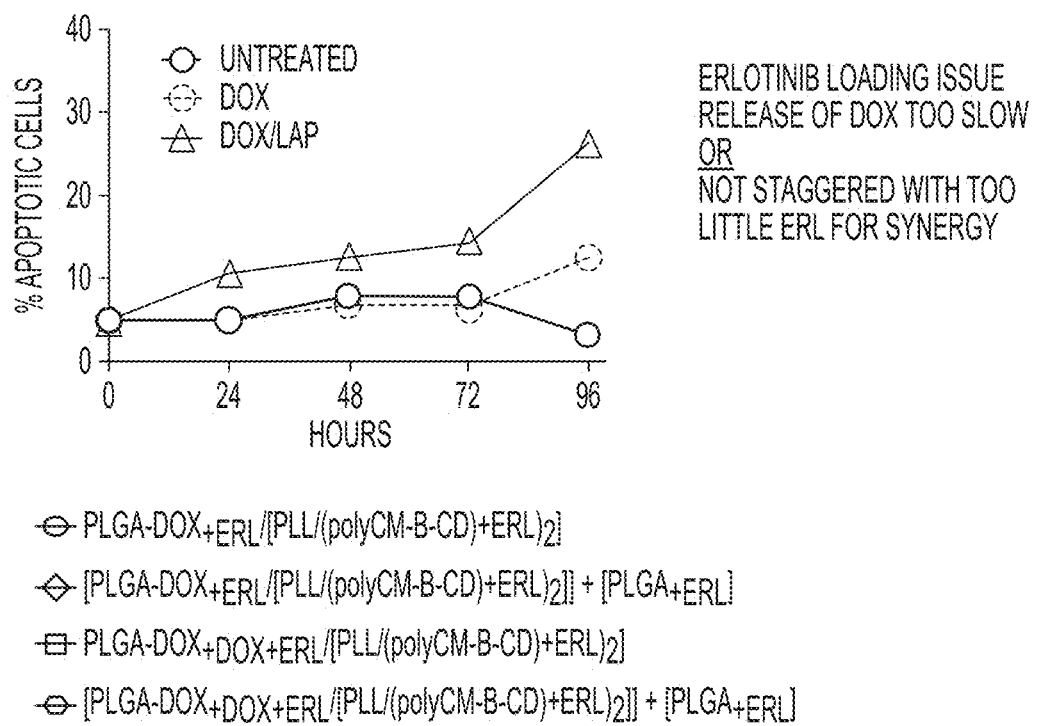

FIG. 21 Cell apoptotic response showing 1) Erlotinib causing issues; 2) use of sister inhibitor (lapatinib).

FIGS. 22A-22C Characterization of combination therapeutic-loaded liposomal system. (A) Schematic of dual loading of small molecule inhibitor (erlotinib) into the hydrophobic, vesicular wall compartment, with cytotoxic agent (doxorubicin) loading in the aqueous, hydrophilic interior. (B) Cryogenic-TEM of multi-drug loaded liposome. (C) Dynamic light scattering, polydispersity index, and zeta-potential measurements for the multi-drug (DE=doxorubicin-erlotinib) and single-drug (D=doxorubicin) liposomal systems, as measured in 10 mM NaCl at 25° C. Mass loading ratio, determined by high-performance liquid chromatography, of the drugs based on an equi-mass feed during fabrication.

Figures 23A, 23B, 23C:
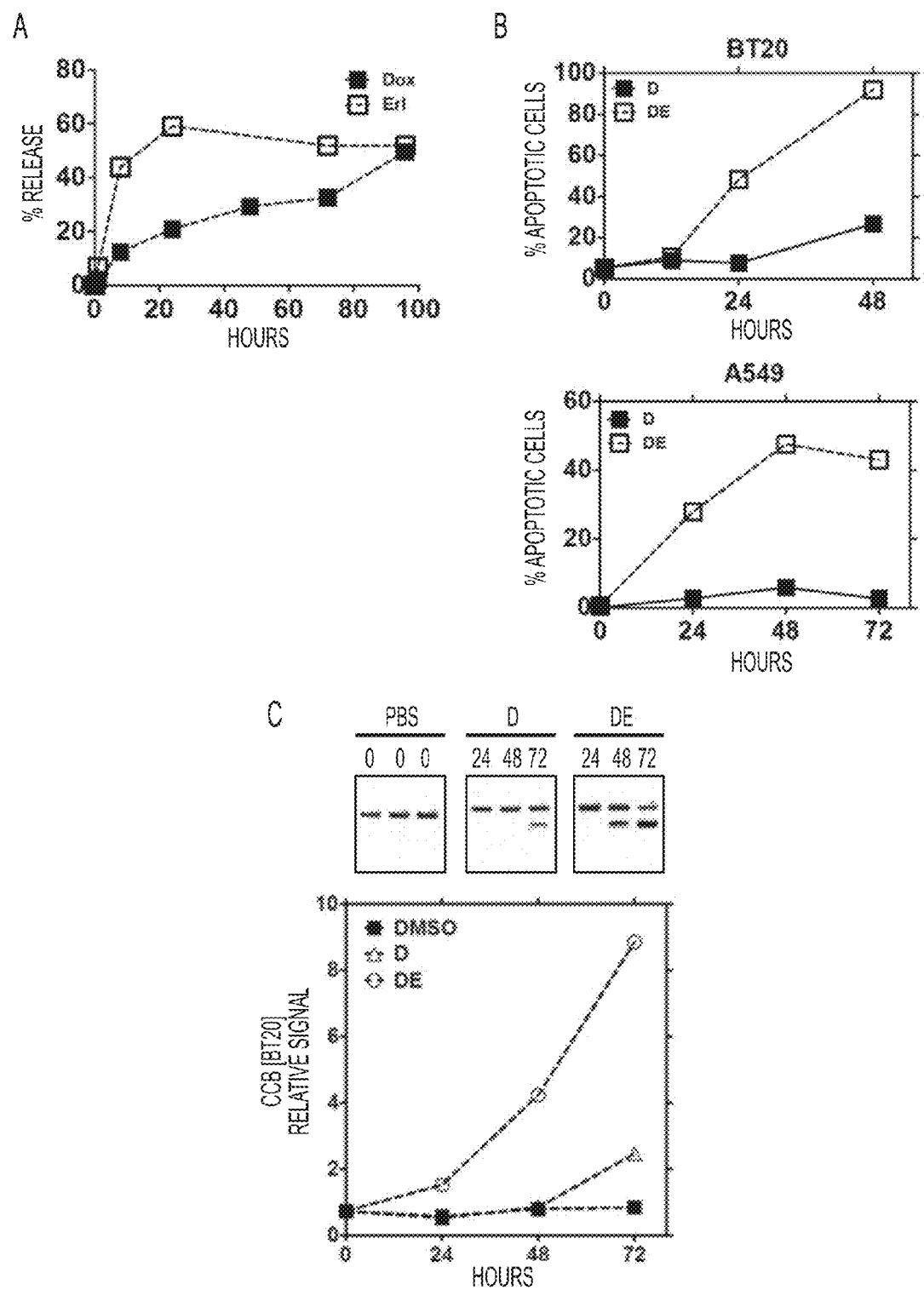

FIGS. 23A-23C Evaluation of combination-therapeutic loaded liposomal system in vitro. (A) Drug release from multi-drug (DE)-loaded liposomes in pH 7.4 PBS at 37° C. under agitation in sink conditions. (B) Comparative cytotoxicity of multi-drug loaded liposome (DE) relative to the single-drug loaded liposome (D) in BT20 (triple negative breast cancer) and A549 (non-small cell lung cancer) cell lines. (C) Cleaved caspase-8 following treatment with multi-drug and single-drug loaded liposome in BT20 cells. Quantification shown below stained gel images corresponds to relative signal of cleaved caspase-8 to actin baseline reporter.

FIGS. 24A-24D Decoration of combination therapeutic-loaded liposomes for targeted delivery. (A) Schematic of addition of $PEG_{2K}$, $PEG_{2K}^{Cy5.5}$ for fluorescent tracking, and $PEG_{5K}$-Folate for targeted delivery. (B) Dynamic light scattering, polydispersity index, and zeta-potential measurements conducted at 25° C. in 10 mM NaCl for the single-drug and multi-drug loaded targeted liposomal systems. Mass loading ratio, determined by high-performance liquid chromatography, of the drugs based on an equi-mass feed during fabrication. (C) Cell uptake of the folate-targeted liposomes in BT20 and A549 cells, and corresponding (D) cell-associated fluorescence (as measured by flow cytometry) in both cell lines. Doses normalized against Cy5.5 fluorescence intensity of NPs administered.

Figure 25A:
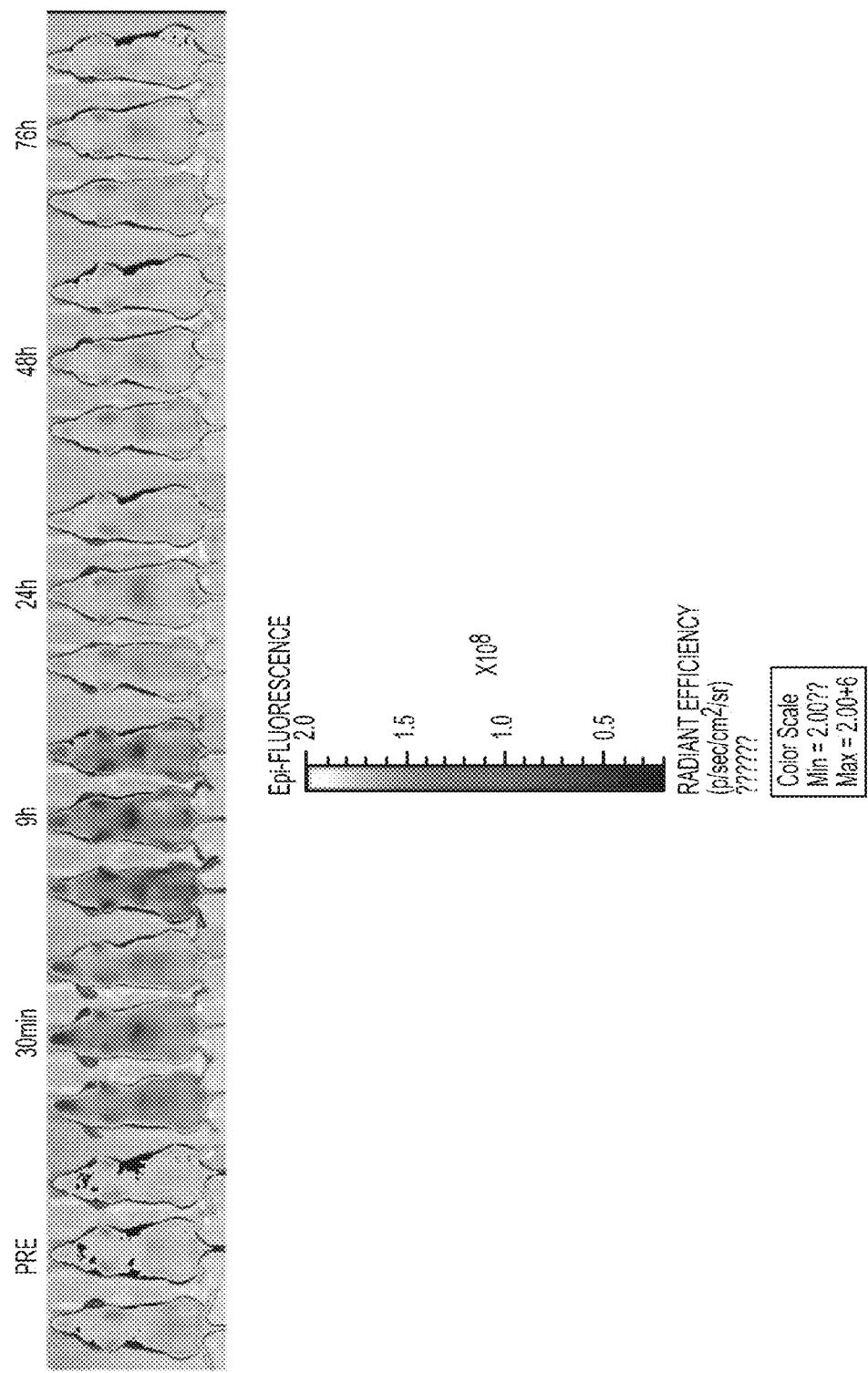
Figure 25B:
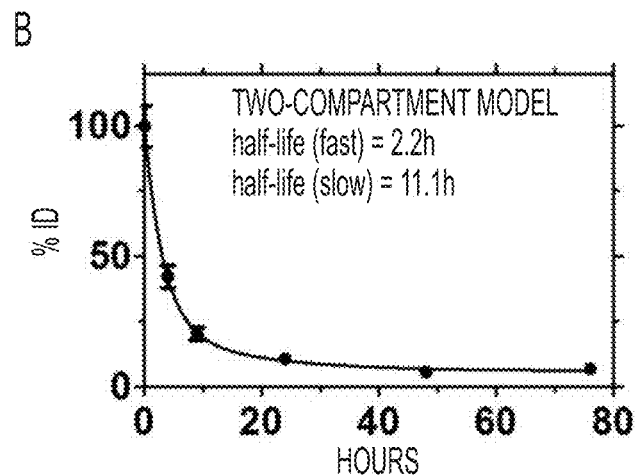
Figure 25C:
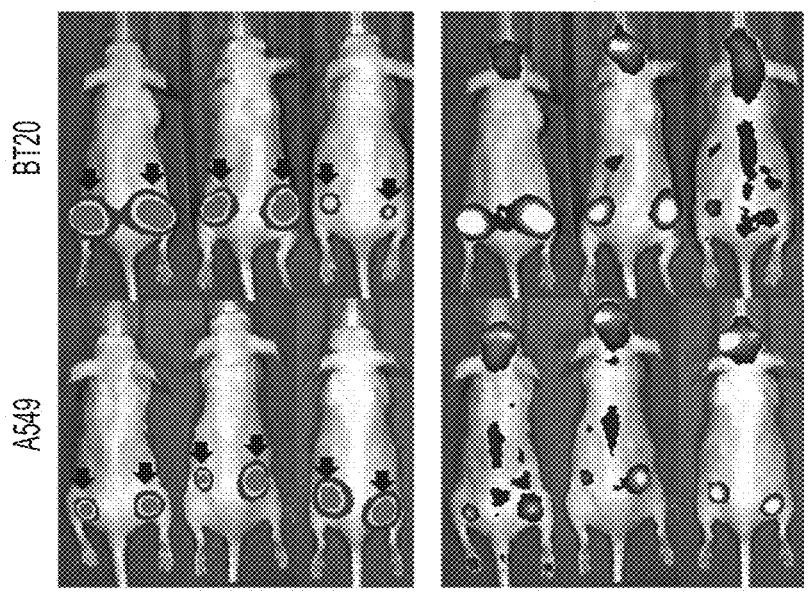

FIGS. 25A-25C Biological performance of folate-targeted liposomal system in vivo. (A) Biodistribution panel of folate-targeted liposomes (tracked via Cy5.5 fluorescence, $\lambda_{ex}$=675 nm|$\lambda_{em}$=720 nm) in BALB/c mice, corresponding to (B) circulation data (displayed as percent injected dose, based on nanoparticle fluorescence via Cy5.5 recovery in blood samples, $\lambda_{ex}$=675 nm|$\lambda_{em}$=720 nm). Half-life calculated based on a two-compartment model. (C) Tumor-targeting (right, visualized by Cy5.5 fluorescence, $\lambda_{ex}$=675 nm|$\lambda_{em}$=720 nm), after 30d post-injection of single 0.1 mL administration folate-targeted liposomes to both BT20- and A549-xenograft bearing NCR nude mice. Simultaneous bioluminescence visualization of xenografts displayed on left.

Figure 26A:
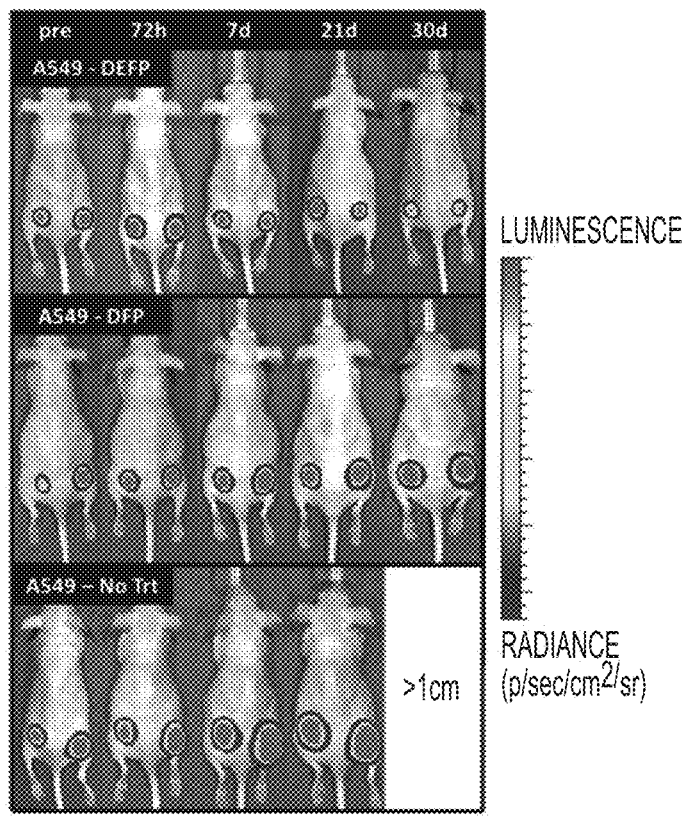
Figure 26A:
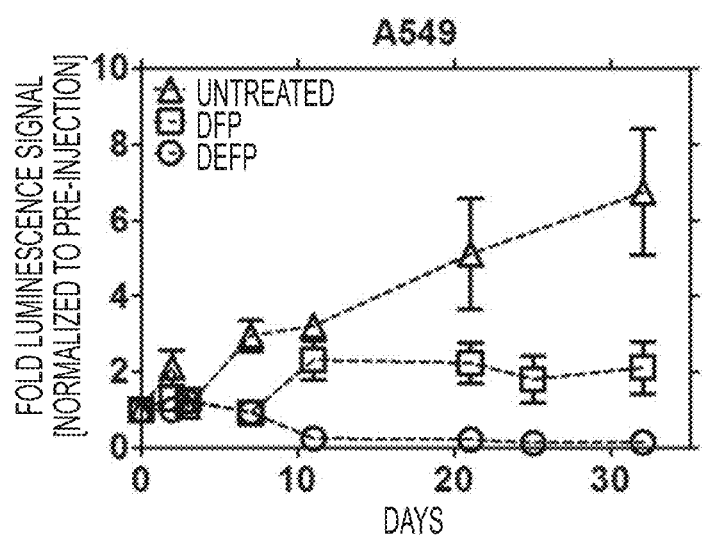
Figure 26B:
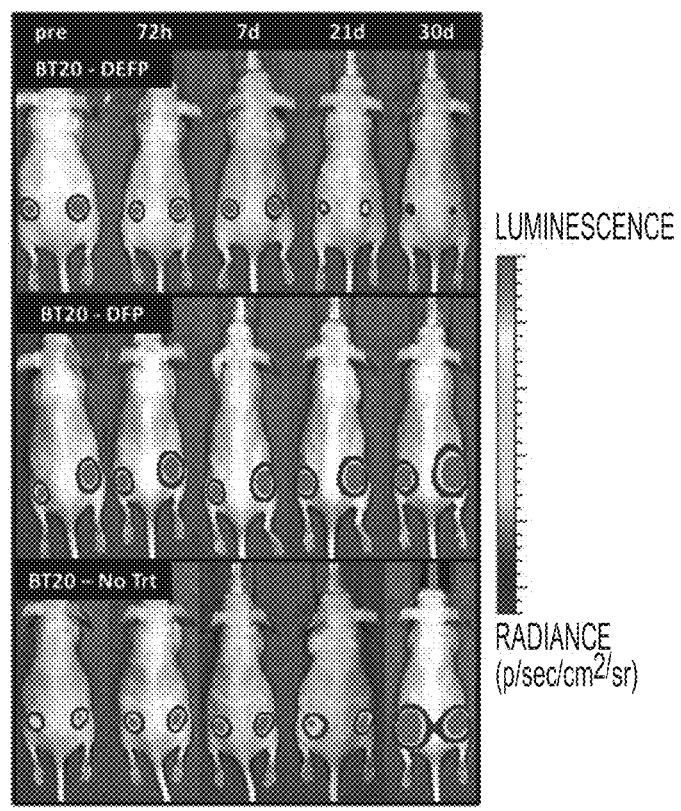
Figure 26B:
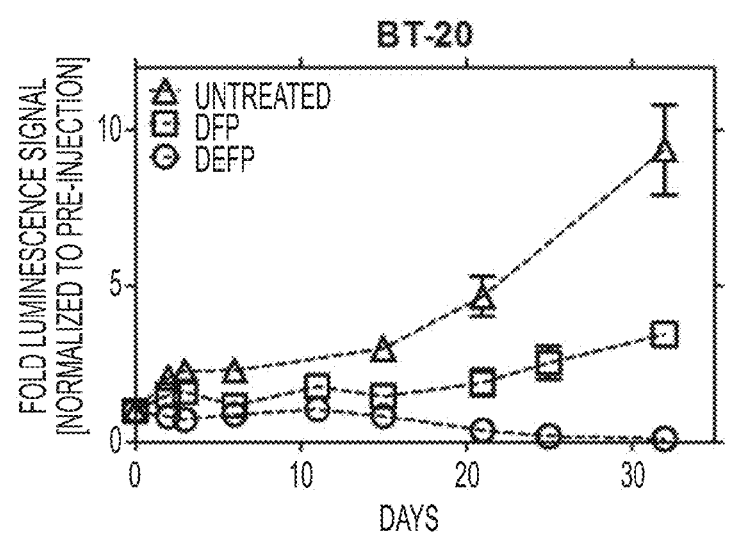
Figure 27E:
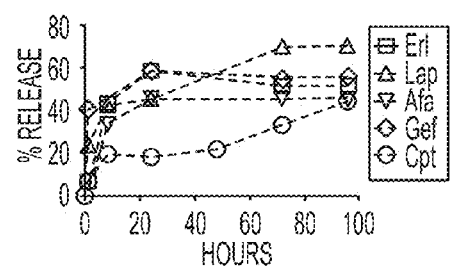
Figure 27F:
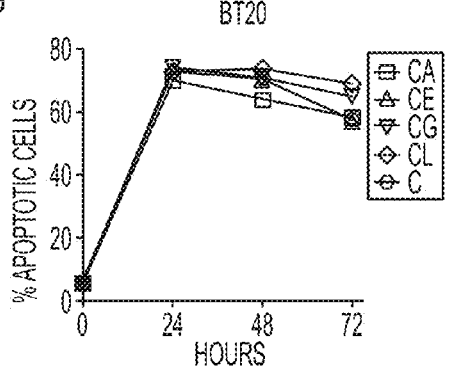
Figure 27G:
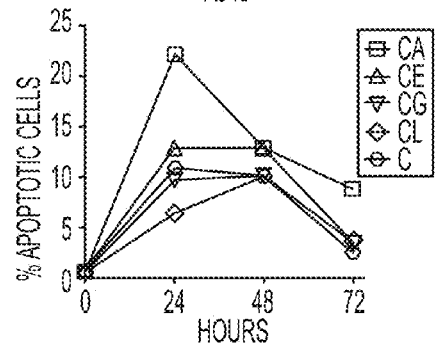

FIGS. 26A-26B Tumor remediation data for multi-drug and single-drug folate-targeted liposomes, along with untreated control. (A) Remediation data for multi-drug (DEFP, top), single-drug (DFP, middle), and untreated control, along with luminescence quantification (reported as fold initial tumor luminescence) corresponding to tumor size as a function of time, following a single administration of 1 mg/kg drug-loaded liposomal formulations in A549-luciferase expressing xenograft-bearing NCR nude mice; n=5, quantification representative of mean+/−SEM. (B) Remediation data for same treatments (1 mg/kg) and control as in (A) for BT20-luciferase expressing xenograft-bearing NCR nude mice; n=5, quantification representative of mean+/−SEM.

FIGS. 27A-27G Developing the inhibito6r-cytotoxic combination liposomal systems as a platform for multi-drug delivery. (A) Schematic of liposomal system, capable of varying the combination of small molecule inhibitor and cytotoxic, for staged delivery. (B) Dynamic light scattering, polydispersity index, and zeta-potential measurements conducted in 10 mM NaCl at 25° C. for the various multi-drug liposomal formulations (D=doxorubicin; A=afatinib; E=erlotinib; G=gefitinib; L=lapatinib; F=folate; P=PEG). Mass loading ratio, determined by high-performance liquid chromatography, of the drugs based on an equi-mass feed during fabrication. (C) Corresponding in vitro drug release from multi-drug loaded liposomal formulations in pH 7.4 PBS at 37° C. under agitation in sink conditions. (D) Comparative cytotoxicity of multi-drug loaded liposomal systems relative to the single-drug loaded liposome (D) in BT20 (triple negative breast cancer) and A549 (non-small cell lung cancer) cell lines. (E) Dynamic light scattering, polydispersity index, and zeta-potential measurements conducted in 10 mM NaCl at 25° C. for the various multi-drug liposomal formulations (C=cisplatin; A=afatinib; E=erlotinib; G=gefitinib; L=lapatinib; F=folate; P=PEG). Mass loading ratio, determined by high-performance liquid chromatography, of the drugs based on an equi-mass feed during fabrication. (F) Corresponding in vitro drug release from multi-drug loaded liposomal formulations in pH 7.4 PBS at 37° C. under agitation in sink conditions. (G) Comparative cytotoxicity of multi-drug loaded liposomal systems relative to the single-drug loaded liposome (C) in BT20 (triple negative breast cancer) and A549 (non-small cell lung cancer) cell lines.

DETAILED DESCRIPTION OF THE INVENTION

I. Compositions

A. Therapeutic Agents

1. EGFR Inhibitors

Compounds that inhibit the EGFR pathway may be useful.

Erlotinib, gefitinbib, herceptin, and tarceva target EGFR family members.

Sunitinib targets multiple receptor tyrosoine kinase inhibitors.

Imatinib targets Abl kinase and PDGF receptors.

Bevacizumab targets VEGF receptors.

Sorafenib targets B-Raf.

BEZ-235 targets PI 3-kinase and mTor.

Torin and rapamycin target mTor.

PD98059 and related compounds target MEK kinase.

SB203580 targets p38 MAPK.

Wortmannin and LY294002 target PI 3-kinase.

PF-3758309 targets p21-activated kinases.

BIBF1120 and Ponatinib inhibits FGF receptor.

SP600125 inhibits JNK kinases.

Preferred compounds are described in the studies below.

Erlotinib hydrochloride (trade name Tarceva) is a drug used to treat non-small cell lung cancer, pancreatic cancer and several other types of cancer. It is a reversible tyrosine kinase inhibitor, which acts on the epidermal growth factor receptor (EGFR). Erlotinib is an EGFR inhibitor. The drug follows Iressa (gefitinib), which was the first drug of this type. Erlotinib specifically targets the epidermal growth factor receptor (EGFR) tyrosine kinase, which is highly expressed and occasionally mutated in various forms of cancer. It binds in a reversible fashion to theadenosine triphosphate (ATP) binding site of the receptor. For the signal to be transmitted, two members of the EGFR family need to come together to form a homodimer. The homodimer uses ATP to autophosphorylate each other, which causes a conformational change in their intracellular structure, exposing a further binding site for binding proteins that cause a signal cascade to the nucleus. By inhibiting the ATP, autophosphorylation is not possible and the signal is stopped.

Sunitinib is an oral tyrosine kinase inhibitor that acts upon vascular endothelial growth factor receptor (VEGFR), platelet-derived growth factor receptor (PDGFR), stem cell factor receptor, and colony-stimulating factor-1 receptor. Gefitinib and erlotinib inhibit the tyrosine kinase domain of epidermal growth factor receptor (EGRF), and can be used to treat lung and pancreatic cancer where there is often over-expression of this cell-surface receptor tyrosine kinase. Kinase inhibitors can also be mediated. Other related compounds include imatinib and nilotinib.

2. DNA Damaging Agents

Doxorubicin (tradename Adriamycin), also known as hydroxydaunorubicin, is used in cancer chemotherapy. Doxorubicin is commonly used in the treatment of a wide range of cancers, including hematological malignancies, many types of carcinomas, and soft tissue sarcomas. Doxorubicin is commonly used to treat some leukemias and Hodgkin's lymphoma, as well as cancers of the bladder, breast, stomach, lung, ovaries, thyroid, soft tissue sarcoma, multiple myeloma, and others. Commonly used doxorubicin-containing regimens are AC (Adriamycin, cyclophosphamide), TAC (Taxotere, CA), ABVD (Adriamycin, bleomycin, vinblastine, dacarbazine), BEACOPP, CHOP (cyclophosphamide, Adriamycin, vincristine, prednisone), FAC (5-fluorouracil, adriamycin, cyclophosphamide), inhibitors of DNA enzyme topoisomerase I, such as cytotoxic quinoline alkaloids (camptothecin, topotecan, and irinotecan), and DNA-crosslinking agents, such as Alkylating agents (BCNU, carmustine) and cis-platin.

Doxorubicin is an anthracycline antibiotic, closely related to the natural product daunomycin. Like all anthracyclines, it works by intercalating DNA. Doxorubicin interacts with DNA by intercalation and inhibition of macromolecular biosynthesis. This inhibits the progression of the enzyme topoisomerase II, which relaxes supercoils in DNA for transcription. Doxorubicin stabilizes the topoisomerase II complex after it has broken the DNA chain for replication, preventing the DNA double helix from being resealed and thereby stopping the process of replication. The planar aromatic chromophore portion of the molecule intercalates between two base pairs of the DNA, while the six-membered daunosamine sugar sits in the minor groove and interacts with flanking base pairs immediately adjacent to the intercalation site, as evidenced by several crystal structures.

Other anthracycline DNA intercalators include daunomycin, arugamycin, epirubicin (an epimer of doxorubicin and differs only in the orientation of the C-4 hydroxyl group on the sugar), idarubicin (an analog of daunorubicin, It lacks the C-4 methoxy group), and valrubicin (N-trifluoroacetyl, 1-4-valerate derivative of doxorubicin).

Other classes of compound include antitumour ene-diyne antibiotics such as Dynemycin.

B. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

i. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug containing microparticles. In this case drug and carrier material are codissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Injectable/Implantable Solid Implants

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

Methods of Making Micro- and Nanoparticles

Spray Drying

In spray drying, the core material to be encapsulated is dispersed or dissolved in a solution. Typically, the solution is aqueous and preferably the solution includes a polymer. The solution or dispersion is pumped through a micronizing nozzle driven by a flow of compressed gas, and the resulting aerosol is suspended in a heated cyclone of air, allowing the solvent to evaporate from the microdroplets. The solidified microparticles pass into a second chamber and are trapped in a collection flask.

Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Hot Melt Encapsulation

In hot melt microencapsulation, the core material (to be encapsulated) is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble drug particles in a polymeric solution for a period of time ranging from 0.5 hours to several months. Stabilizing an insoluble drug and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble drug particles within the polymeric solution could be critical during scale-up. By stabilizing suspended drug particles within the dispersed phase, said particles can remain homogeneously dispersed throughout the polymeric solution as well as the resulting polymer matrix that forms during the process of microencapsulation. The homogeneous distribution of drug particles can be achieved in any kind of device, including microparticles, nanoparticles, rods, films, and other device.

Solvent evaporation microencapsulation (SEM) has several advantages. SEM allows for the determination of the best polymer-solvent-insoluble particle mixture that will aid in the formation of a homogeneous suspension that can be used to encapsulate the particles. SEM stabilizes the insoluble particles s within the polymeric solution, which will help during scale-up because one will be able to let suspensions of insoluble particles sit for long periods of time, making the process less time-dependent and less labor intensive. SEM allows for the encapsulated particles to remain suspended within a polymeric solution for up to 30 days, which may increase the amount of insoluble material entrapped within the polymeric matrix, potentially improving the physical properties of the drug delivery vehicle. SEM allows for the creation of microparticles or nanoparticles that have a more optimized release of the encapsulated material. For example, if the insoluble particle is localized to the surface of the microparticle or nanoparticle, the system will have a large 'burst' effect. In contrast, creating a homogeneous dispersion of the insoluble particle within the polymeric matrix will help to create a system with release kinetics that begin to approach the classical 'zero-ordered' release kinetics that are often perceived as being ideal in the field of drug delivery). Finally, SEM allows for a higher loading of unencapsulated drug, helping to create microparticles or nanoparticles for drug delivery.

Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Phase Inversion Nanoencapsulation ("PIN")

A preferred process is PIN. In PIN, a polymer is dissolved in an effective amount of a solvent. The agent to be encapsulated is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible. PIN has been described by Mathiowitz et al. in U.S. Pat. Nos. 6,131,211 and 6,235,224. A hydrophobic agent is dissolved in an effective amount of a first solvent that is free of polymer. The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less.

An improved process is demonstrated in the examples. The process uses a mixed solvent including at least one water-insoluble solvent and water that contains a surfactant, such as PVA. The drug is either dissolved or dispersed together with a substance that has a high molecular weight (such as a polymer) into an organic solvent composition, optionally containing non-ionic surfactants of various hydrophilic-lipophilic ratios. The composition is then introduced into an aqueous solution that contains a surfactant like PVA. The water-insoluble solvent forms an oil phase (inner phase) and is stirred into the aqueous solution as a water phase (outer phase). The O/W emulsion is combined with fresh water that contains surfactant such as PVA and is stirred to help aid the solvent evaporation. The aqueous solution contains an activator such as polyvinyl alcohol, whereby the oil phase is enclosed as small droplets within the aqueous solution as shells. The proportion of the water-miscible solvent in the oil phase is from 5% to 95%. An important aspect of this improved method is the use of high shear during the initial mixing phase, which is achievable, for example, using sonication for a period of one hour, with stirring, to uniformly mix in high amounts of drug particles in the polymer liquefied by dissolution or by melting.

Melt-Solvent Evaporation Method

In the melt-solvent evaporation method, the polymer is heated to a point of sufficient fluidity to allow ease of manipulation (for example, stirring with a spatula). The temperature required to do this is dependent on the intrinsic properties of the polymer. For example, for crystalline polymers, the temperature will be above the melting point of the polymer. After reaching the desired temperature, the agent is added to the molten polymer and physically mixed while maintaining the temperature. The molten polymer and agent are mixed until the mixture reaches the maximum level of homogeneity for that particular system. The mixture is allowed to cool to room temperature and harden. This may result in melting of the agent in the polymer and/or dispersion of the agent in the polymer. This can result in an increase in solubility of the agent when the mixture is dissolved in organic solvent. The process is easy to scale up since it occurs prior to encapsulation. High shear turbines may be used to stir the dispersion, complemented by gradual addition of drug into the polymer solution until the desired high loading is achieved. Alternatively the density of the polymer solution may be adjusted to prevent drug settling during stirring.

This method increases microparticle loading as well as uniformity of the resulting microparticles and of the drug within the microparticles. When a drug is formed into microspheres by double-emulsion solvent evaporation, transfer of the drug from the inner phase to the outer water phase can be prevented. This makes it possible to increase the percentage of drug entrapped within the microspheres, resulting in an increased amount of the drug in the microspheres.

The distribution of the drug in particles can also be made more uniform. This can improve the release kinetics of the drug. Generally, the drug is dissolved or dispersed together with a substance that has a high molecular weight in an organic solvent composition; with or without non-ionic surfactants of various hydrophilic-lipophilic ratios. The composition is introduced into an aqueous solution that contains a surfactant like PVA. The water-insoluble solvent forms an oil phase (inner phase) and is stirred into the aqueous solution as a water phase (outer phase). The O/W emulsion is combined with fresh water that contains PVA and is stirred to help aid the solvent evaporation. The aqueous solution contains an activator such as polyvinyl alcohol, whereby the oil phase is enclosed as small droplets within the aqueous solution as shells.

II. Methods of Treatment

A. Disorders to be Treated

The results described below demonstrate that time-staggered inhibition of EGFR, in combination with DNA damaging agents, is a useful therapeutic strategy for treating cancers, especially a subset of triple-negative tumors, particularly those with high basal levels of phosphorylated EGFR.

The staggered therapy was also demonstrated to be applicable to other types of tumors, especially lung cancers, which contain either high levels of phosphorylated wild-type EGFR or mutations within EGFR itself.

B. Administration of Drugs

EGFR inhibition dramatically sensitizes a subset of TNBCs to DNA damage if the drugs are given sequentially, but not simultaneously. The first drug must be administered in a dosage and for a period of time sufficient for the dynamic network rewiring of an oncogenic signature maintained by active EGFR signaling to unmask an apoptotic process that involves activation of caspase-8. The enhanced sensitivity to damaging agents requires sustained inhibition of EGFR from modulation of an oncogene-driven transcriptional network as indicated schematically in the model shown in FIG. 7G. It is activity of the EGFR pathway, rather than EGFR expression per se, that determines whether time-staggered inhibition will result in synergistic killing. These observations indicate that EGFR phosphorylation is a useful biomarker of response to time-staggered inhibition in at least some tumor types that are EGFR driven, including some TNBCs and lung cancers.

The results demonstrate the EGFR pathway inhibitor must be administered about eight hours or more, such as one day before, administration of the chemotherapeutic.

The present invention will be further understood by reference to the following non-limiting examples.

Materials and Methods

Cell Culture

All cell lines were obtained from American Type Culture Collection (ATCC) and maintained at low passage (less than 20 passages). Basal media for BT-20 cells was in MEMa+ Earle's Salts. A549, MDA-MB-453, MCF7, MDA-MB-231, MDA-MB-468, MDA-MB-436, MDA-MB-157, Hs578T, and Hs578BST were grown in Dulbecco's modified eagles medium (DMEM). Hs578T and Hs578Bst were further supplemented with 1 µg/ml insulin and 30 ng/ml EGF, respectively. HCC-1143, HCC-38, HCC-1500, NCI-1650, NCI-358, BT-474, and BT-549 were grown in RPMI1640 media, and BT-549 cells were supplemented with 1 µg/ml insulin.

Growth media for each line was supplemented with 10% fetal bovine serum (FBS), 2 mm Glutamine, and penicillin/streptomycin. All cells were cultured at 37° C. in a humidified incubator supplied with 5% $CO_2$.

SiRNA Knockdown

Silencer Select Validated siRNAs were purchased through Invitrogen.

```
For EGFR, sioligos used were:
GAUCUUUCCUUCUUAAAGAtt (sense)      (SEQ ID. NO. 1)
and UCUUUAAGAAGGAAAGAUCat (antisense); (SEQ ID. NO. 2)
and CCAUAAAUGCUACGAAUAUtt (sense)      (SEQ ID. NO. 3)
and AUAUUCGUAGCAUUUAUGGag (antisense). (SEQ ID. NO. 4)

Oligos for caspase-8 were:
GAUACUGUCUGAUCAUCAAtt (sense)      (SEQ ID. NO. 5)
and UUGAUGAUCAGACAGUAUCcc (antisense); (SEQ ID. NO. 6)
and GAUCAGAAUUGAGGUCUUUtt (sense)      (SEQ ID. NO. 7)
and AAAGACCUCAAUUCUGAUCtg (antisense). (SEQ ID. NO. 8)

Oligos for caspase-6 were:
GGCUCCUCCUUAGAGUUGAtt (sense)      (SEQ ID. NO. 9)
and UGAACUCUAAGGAGGAGCCat (antisense); (SEQ ID. NO. 10)
and GCAUCACAUUUAUGCAUAtt (sense)       (SEQ ID. NO. 11)
and UAUGCAUAAAUGUGAUUGCct (antisense). (SEQ ID. NO. 12)

Oligos for Beclin1 were:
CAGUUACAGAUGGAGCUAAtt (sense)      (SEQ ID. NO. 13)
and UUAGCUCCAUCUGUAACUGtt (antisense), (SEQ ID. NO. 14)
and GCAGUUGAAAGAAGAGGUUtt (sense)      (SEQ ID. NO. 15)
and AACCUCUUCUUUGAACUGCtg (antisense). (SEQ ID. NO. 16)

Oligos for RIP1 were:
CCACUAGUCUGACGGAUAAtt (sense)      (SEQ ID. NO. 17)
and

UUAUCCGUCAGACUAGUGGta (antisense), (SEQ ID. NO. 18)
and

GCAAAGACCUUACGAGAAUUtt (sense)     (SEQ ID. NO. 19)
and

AUUCUCGUAAGGUCUUUGCtg (antisense). (SEQ ID. NO. 20)
```

For transfection in human cell lines, Lipofectamine RNAiMAX was used according to manufacturer's instructions. Dose titration and time course experiments were performed to determine that optimal knockdown efficiency, which in all experiments was 5 nM siRNA for 48 hrs.

Cellular Response Assays

Apoptosis

1×106 cells were seeded in a 10 cm dish 24 hr prior to the experiment. For treatments involving doxorubicin and/or erlotinib, both drugs were used at a final concentration of 10 µM unless otherwise noted. Following the treatment time course, cells were washed in PBS, trypsinized, and fixed in 4% paraformaldehyde (PFA) in PBS for 15 min at room temperature (RT), then resuspended in ice cold methanol and incubated overnight at −20° C. Cells were then washed twice in PBS+0.1% Tween and stained with antibodies directed against cleaved forms of caspase-3 and PARP (BD PharMingen). Secondary antibodies conjugated to Alexa dyes (488 and 647) were used for visualization in a BD FacsCaliber flow cytometer (Molecular Probes). Data reported are always percent cleaved-caspase-3/cleaved-PARP double positive cells.

Cell-Cycle Analysis

Cells were plated and treated as above, but fixed in 70% ethanol in PBS overnight at −20° C., permeabilized with PBS containing 0.25% Triton X-100 for 20 min at 4° C., blocked with 1% bovine serum albumin in PBS, and incubated with anti-phospho-Histone H3 antibody for 1 hr (Millipore). Following washing, cells were incubated with Alexa488-conjugated secondary antibody for 1 hr on ice, washed, and resuspended in PBS containing 50 µg/ml propidium iodide (PI) prior to analysis on a BD FACScaliber flow cytometer. Data were analyzed using the FloJo software, and the Dean-Jett-Fox algorithm for cell cycle analysis.

Cell Viability/Proliferation

Cells were plated at 5,000 cells per well in 96-well optical bottom plates. Metabolic viability was determined using CellTiterGlo (Promega) according to the manufacturer's protocol. Linearity of the luminescent signal was validated for each cell line used, and data were validated by comparison to total cell count as determined by a Coulter counter.

Autophagy

Cells were stably transfected with pBABE-mCherry-EGFP-LC3B (Addgene Plasmid 22418), which reports activation of autophagy and maturation of autophagic particles to autolysosomes. Expression of this plasmid was determined to have no effect on cell growth rate, apoptosis, or chemosensitivity (data not shown). Cells were seeded onto 18 mm2 coverslips and treated with erlotinib or doxorubicin or both for the indicated times. Cells were then fixed in 3% PFA and 2% sucrose for 15 min at AT, and stained for 10 min with whole cell blue stain according to manufacturer's protocol (Thermo Scientific). Images were collected on an Applied Precision DeltaVision Spectris automated microscope and deconvolved using Applied Precision SoftWoRx software. Deconvolved image projections were analyzed using Cei-iProfiler to identify total cells as well as autophagic cells. A modified "speckle counter" pipeline was used as described by Carpenter, A. E., Jones, T. R., Lamprecht, M. R., Clarke, C., Kang, I. H., Friman, O., Guertin, D. A., Chang, J. H., Lindquist, R. A., Moffat, J., et al. (2006). CellProfiler: Image Analysis Software for Identifying and Quantifying Cell Phenotypes. Genome Bioi. 7, R100). Briefly, whole cell blue signal was used to segment each image into individual cells. Number of GFP or mCherry LC3 puncta were counted per cell, and cells were counted as "autophagic" if the number of GFP and mCHERRY puncta significantly increased relative to untreated cells (Mizushima, N., Yoshimori, T., and Levine, B. (2010). Methods in Mammalian Autophagy Research. Cell 140, 313-326). Approximately 100 cells were counted in a double blind fashion per condition, and percent autophagic cells reported from 3 independent experiments.

Apoptosis

Following the treatment time course, cells were washed, trypsinized, fixed in 4% paraformaldehyde for 15 min at room temperature, resuspended in ice-cold methanol, and incubated overnight at −20° C. Cells were then washed twice in PBS-Tween and stained with antibodies against cleaved caspase-3 and poly(ADP-ribose) polymerase (PARP). Secondary Alexa-conjugated anti-bodies were used for visualization in a BD FacsCaliber flow cytometer.

Cell-Cycle Analysis

Cells were fixed in 70% ethanol overnight at −20° C., permeabilized with 0.25% Triton X-100 for 20 min at 4° C., blocked with 1% BSA, and incubated with anti-phospho-histone H3. Following washing, cells were incubated with Alexa488-conjugated secondary antibody on ice, washed, and stained with propidium iodide (PI) prior to analysis. Data were analyzed using the Dean-Jell-Fox algorithm.

Cell Viability/Proliferation

Cells were plated at 5,000 cells per well in 96-well plates. Metabolic viability was determined using CellTiterGlo (Promega) according to the manufacturer's protocol.

Western Blotting and Antibodies

Cells were lysed in a manner that would allow samples to be used for both western blot analysis and reverse-phase protein microarray. Data generated by quantitative western blot were preprocessed prior to use in computational modeling. Raw signals for each protein target of interest were quantified and background subtracted using the Li-COR Odyssey software and divided by P-actin signals to normalize for loading differences, and then each normalized signal was divided by a reference sample contained on each gel for gel-to-gel normalization.

Reverse-Phase Protein Microarray

Reverse-phase protein microarrays were printed on a fee-for-service basis through Aushon Biosystems. Validation of antibodies, staining, and analysis of array data was performed as described by Sevecka, M., and MacBeath, G. (2006). State-Based Discovery: A Multidimensional Screen for Small-Molecule Modulators of EGF Signaling. Nat. Methods 3, 825-831.

Immunofluorescence Microscopy

Cells were seeded onto coverslips and treated for the indicated times. For autophagy analysis, cells were stably transfected with an mCHERRY-GFP-LC3 reporter construct. Cells were fixed and stained with primary antibody targeting either p-H2AX or 53BP1 and DAPI. Data reported are integrated intensity of pH2AX or 53BP1 foci per nucleus. For autophagy measurements, cells were scored positive if the number of GFP and mCHERRY puncta significantly increased relative to untreated cells. Approximately 100 cells were counted in a double-blind fashion per condition. Each experiment was performed in experimental triplicate.

RNA Expression Analysis by Microarray

RNA was extracted from cells using the RNAeasy Kit (QIAGEN). Affymetrix Human U133 Plus 2.0 microarrays were hybridized, labeled, and processed on a fee-for-service basis through the MIT BioMicro Center. Microarray data were obtained from three independent biological replicates per time point and analyzed using linear model for microarray (LIMMA).

Computational Modeling and Statistics

Unless otherwise noted, all statistical analyses were performed using Graph-pad Prism, and graphs were created using Microsoft Excel, Spotfire, Matlab, DataRail, or SIMCA-P. Analysis of flow cytometry data was performed using FloJo. Analysis of RNA expression microarray data was performed using either GSEA or GeneGO.

Data-Driven Modeling

Data-driven modeling and the application of partial least-squares to biological data have been described by Janes, K. A., Albeck, J. G., Gaudet, S., Sorger, P. K., Lauffenburger, D. A., and Yaffe, M. B. (2005). A systems model of signaling identifies a molecular basis set for cytokine-induced apoptosis. Science 310, 1646-1653. All data were variance scaled to nondimensionalize the different measurements. Model predictions were made via cross-validation. Model fitness was calculated using R2, O2, and RMSE, as described by Gaudet, S., Janes, K. A., Albeck, J. G., Pace, E. A., Lauffenburger, D. A., and Sorger, P. K. (2005). A Compendium of Signals and Responses Triggered by Pro-death and Prosurvival Cytokines Mol. Cell. Proteomics 4, 1569-1590. VIP was calculated following Janes, K. A., Reinhardt, H. C., and Yaffe, M. B. (2008). Cytokine-Induced Signaling Networks Prioritize Dynamic Range Over Signal Strength. Cell 135, 343-354.

Doxorubicin Influx Measurements

Doxorubicin is a naturally fluorescent molecule. Measurement of doxorubicin retention was performed as described by Turner, J. G., Gump, J. L., Zhang, C., Cook, J. M., Marchion, D., Hazlehurst, L., Munster, P., Schell, M. J., Dalton, W. S., and Sullivan, D. M. (2006). ABCG2 Expression, Function, and Promoter Methylation in Human Multiple Myeloma. Blood 108, 3881-3889. Doxorubicin and erlotinib were both added to a final concentration of 10 µM.

RNA Expression Analysis by Microarray Analysis

RNA was extracted from cells using the RNAeasy Kit (QIAGEN). Affymetrix Human U133 Plus 2.0 microarrays were hybridized, labeled and processed on a fee-for-service basis through the BioMicro Center at MIT. Microarray data were obtained from 3 independent biological replicates per time point. Detailed analysis of microarray data was performed with help from the Bioinformatics Core Facility at the Koch Institute at MIT. Expression data can be found in the GEO repository under the accession number GSE30516.

Soft Agar Growth Assay

Soft agar growth assays were performed as described by Sapi, E., Flick, M. B., Rodov, S, and Kacinski, B. M. (1998). Ets-2 Transdominant Mutant Abolishes Anchorage-Independent Growth and Macrophage Colony Stimulating Factor-Stimulated Invasion by BT20 Breast Carcinoma Cells. Cancer Res. 58, 1027-1033.

Chemicals

Doxorubicin hydrochloride (doxorubicin), PD98059, BMS-345541, rapamycin, wortmannin, taxol, cisplatin, etoposide, camptothe-cin, and temezolomide were purchased through Sigma; Erlotinib, Gefitinib, and lapatinib were purchased through 1C laboratories; NVP-BEZ235 was a generous gift from Dr. Lewis Cantley (Harvard Medical School).

Xenograft Tumor Model

For in vivo tumor regression assays, 107 BT-20 cells in PBS were mixed 1:1 with Matrigel on ice and injected subcutaneously into the hindflanks of nude mice (NCR nu/nu, Taconic). Tumors were allowed to form for 7 days. Mice were then treated intraperitoneally with doxorubicin (4 mg/kg) or a combination of doxorubicin and erlotinib (25 mg/kg), with erlotinib either given at the same time as doxorubicin (D/E) or given 8 hr prior to doxorubicin (E→D). Tumors were monitored for 14 days after the treatment phase, and volume was estimated using the ½L×W2 formula. These experiments were approved by the Massachusetts Institute of Technology Committee on Animal Care (CAC).

Accession Numbers

Expression data can be found in the GEO repository under the accession number GSE30516.

Results

A Critical Order and Time Dependency for Enhanced EGFR Inhibition/DNA Damage-Mediated Cell Death Signaling networks can respond to, and can be functionally rewired by, exposure to specific ligands or drugs (Janes et al., 2005, 2008). It is increasingly clear that these responses are time dependent. It was reasoned that it should, in principle, be possible to dynamically rewire the DDR network in an insensitive cell through prior exposure to a drug that modulates the network, thereby rendering the cell sensitive to DNA-damaging agents. To test this hypothesis, a series of drug combinations was tested for synergism or antagonism in breast cancer cells using protocols that changed both the order and timing of drug addition.

Genotoxic agents were combined with small molecule inhibitors targeting common oncogenic signaling pathways (FIG. 1A). Drugs that are known to be clinically useful in other cancers but are known to lack efficacy in TNBC individually or in combination (Bosch, A., Eroles, P., Zaragoza, A., Viiia, J. R., and Lluch, A. (2010) were included. Triple-negative breast cancer: molecular features, pathogenesis, treatment and current lines of research. Cancer Treat. Rev. 36, 206-215; Winer, E. P., and Mayer, E. L. (2007). Optimizing Treatment of "Triple-Negative" Breast Cancer. SABCS 2007: Improving Outcomes in Advanced and Meta-static Breast Cancer. http://www.medscape.org/viewarticle/569483). Previous studies using cell culture models of TNBC, for example, reported that EGFR inhibitors in combination with genotoxic compounds such as cisplatin resulted in less than a 10% survival benefit (Corkery, B., Crown, J., Clynes, M., and O'Donovan, N. (2009). Epidermal growth factor receptor as a potential therapeutic target in triple-negative breast cancer. Ann. Oneal. 20, 862-867), whereas a randomized phase II trial in TNBC patients reported that addition of cetuximab to carboplatin did not improve outcome (Carey, L., Ruga, H., Marcom, P., Irvin, W.•Ferraro, M., Burrows, E., He, X., Perou, C., and Winer, E. (2008). TBCRC 001: EGFA inhibition with cetuximab added to carboplatin in metastatic triple-negative (basal-like) breast cancer. J. Clin. Oneal. 26, 26-31). However, emerging understanding of the complex nonlinear and time-dependent interplay between signaling networks argues that a more systematic assessment exploring not only dosage, but also the order of drug presentation, scheduling, and dose duration might uncover cross-pathway effects and efficacious interactions that were missed previously (Fitzgerald, J. B., Schoeberl, B., Nielsen, U. B. and Sorger, P. K. (2006). Systems Biology and Combination Therapy in the Quest for Clinical Efficacy. Nat. Chem. Bioi. 2, 458-466). An initial combination screen was therefore performed in a panel of canonical breast cancer cell lines representing those that are hormone sensitive (MCF7), HER2 overexpressing (MDA-MB-453), or triple negative (BT-20) (Neve, A. M. Chin, K., Fridlyand, J., Yeh, J., Baehner, F. L., Fevr, T., Clark, L., Bayani, N., Coppa, J. P., Tong. F., et al. (2006). A collection of breast cancer cell lines or the study of functionally distinct cancer subtypes. Cancer Cell 10, 515-527). A first pass of the screen, scoring for viability, was performed in BT-20 cells, and a subset of combinations was then explored more thoroughly, scoring for viability, proliferation, and apoptotic responses in the panel of three cell lines (FIGS. 1B-1E).

Inhibition of EGFR using the compound erlotinib (ERL) was not a potent apoptotic stimulus in TNBC cells when used alone or when added at the same time as or shortly before doxorubicin (DOX) (FIG. 1B, left bars 1-6). Surprisingly, however, combinations in which erlotinib was added at least 4 hr prior to doxorubicin showed a markedly enhanced apoptotic response, with cell killing increasing by as much as 500% (FIG. 1B, middle bars 7-10). When the order of drug presentation was reversed, doxorubicin given before erlotinib, cell killing was not enhanced relative to treatment with doxorubicin or erlotinib alone (FIG. 1B, right bars 11 and 12).

The efficacy of the time-sequenced erlotinib-doxorubicin treatment was analyzed for doxorubicin dose-effect relationships using the Chou-Talalay method (Chou, T. C., and Talalay, P. (1984). Quantitative analysis of dose-effect relationships: the combined effects of multiple drugs or enzyme inhibitors. Adv. Enzyme Regul. 22, 27-55) and was found to vary significantly across breast cancer subtypes (FIGS. 1C-1E and 1G). Whereas chronic EGFR inhibition was synergistic with doxorubicin in killing TNBC breast tumor (B1)-20 cells, the same treatment regimen antagonized doxorubicin sensitivity in HER2-overexpressing MDA-MB-453 cells. All temporal erlotinib-doxorubicin combinations tested were merely additive in luminal MCF7 cells. The order and timing of drug addition had little effect in Hs578Bst, a cell line derived from normal peripheral breast tissue, which was generally drug resistant (FIG. 1F).

Furthermore, this enhanced treatment effect in BT-20 cells was not limited to combinations of doxorubicin and erlotinib. Synergistic killing was also observed following time-staggered pretreatment of BT-20 cells with either erlotinib, gefitinib, or lapatinib (all EGFR inhibitors) in combination with the DNA-damaging agent camptothecin, as well as with doxorubicin (FIGS. 8A-8C) (Wood, E. A., Truesdale, A. T., McDonald, O. B., Yuan, D., Hassell, A., Dickerson, S. H., Ellis, 8., Pennisi, C., Horne, E. Lackey, K., et al. (2004). A unique structure for epidermal growth factor receptor bound to GW572016 (Lapatinib): relationships among protein conformation, inhibitor off-rate, and receptor activity in tumor cells. Cancer Res. 64, 6652-6659)

Figures 9A, 9B, 9C:
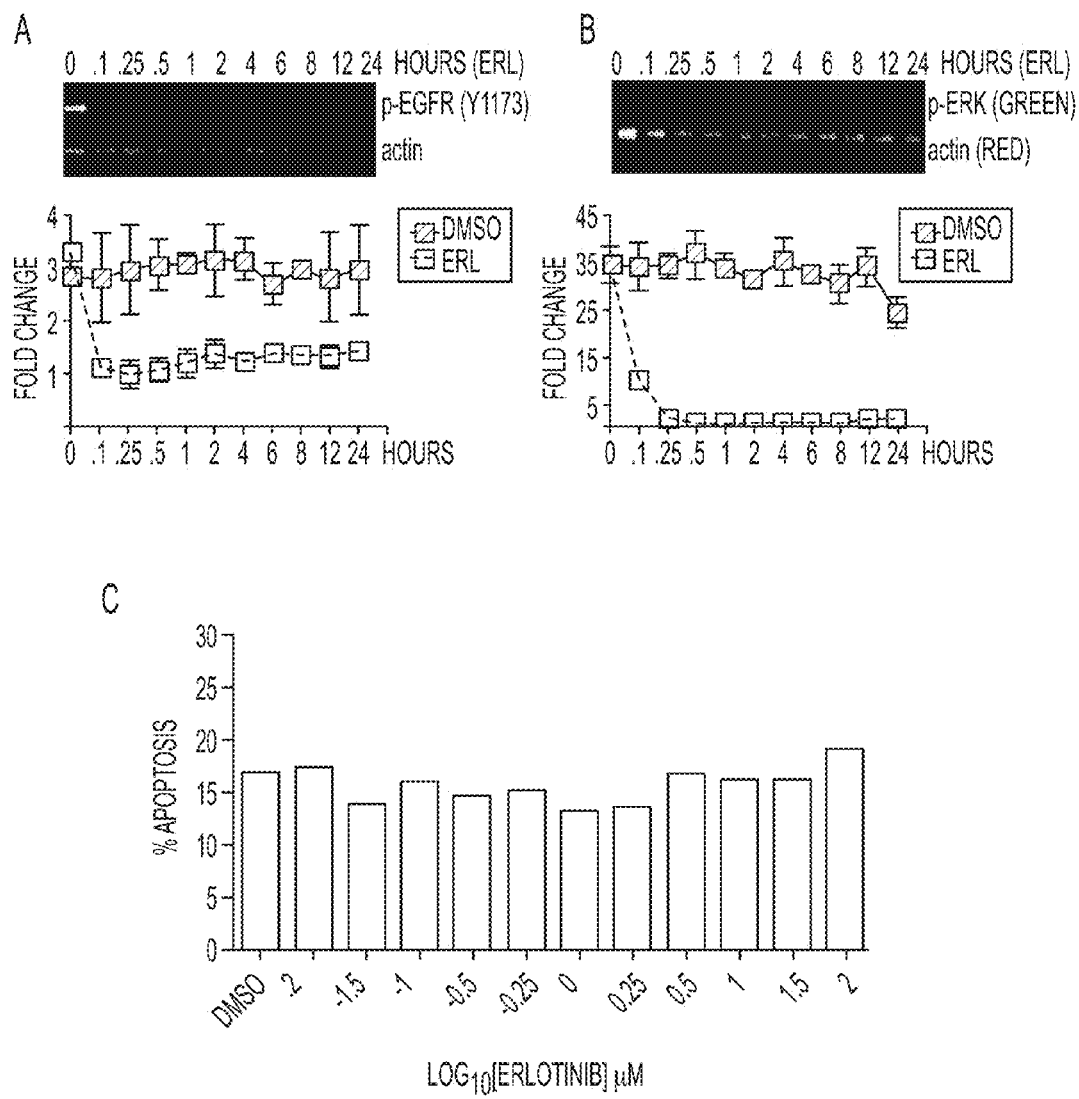
Figure 9D:
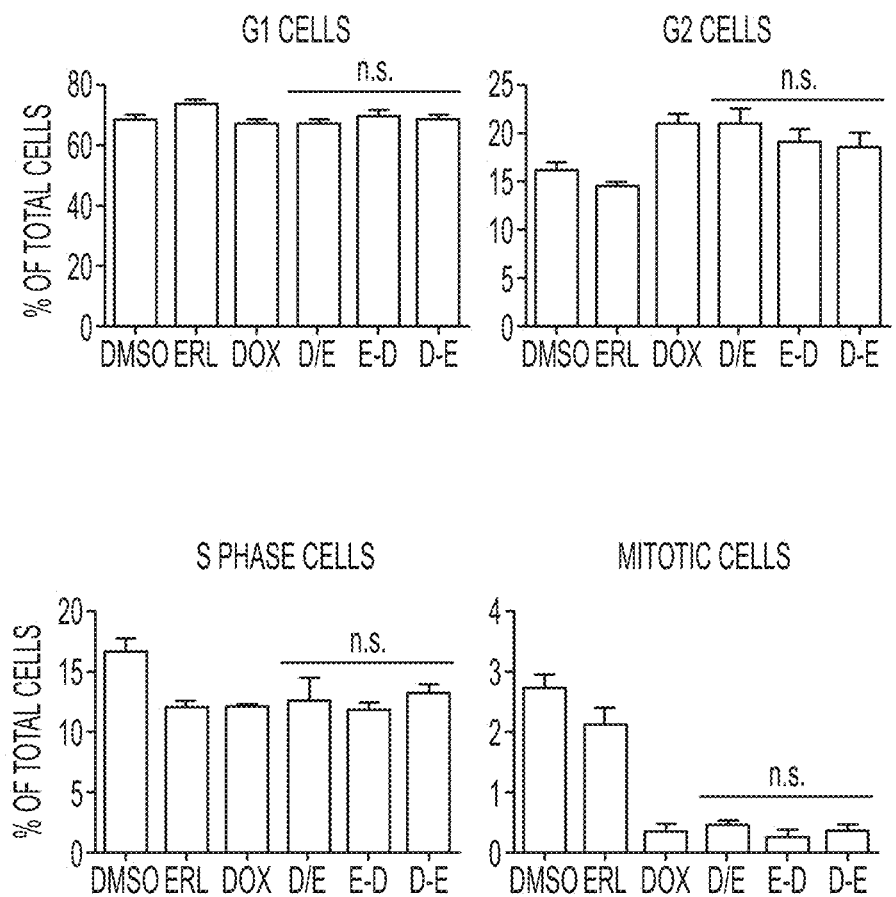

Although erlotinib inhibits EGFR and downstream signaling within minutes (FIGS. 9A and 9B), enhanced cell death in response to DNA-damaging agents required pretreatment with erlotinib for several hours. To verify that this was indeed due to on-target inhibition of EGFR, in addition to testing other EGFR inhibitors (above), EGFR was knocked down using two different small interfering RNAs (siRNAs). Like the time-staggered erlotinib-doxorubicin treatment, strong proapoptotic responses were observed in BT-20 cells following EGFR knockdown with delayed doxorubicin treatment (FIGS. 1H and 1I). Importantly, the addition of erlotinib to EGFR knockdown cells had no additional effect, arguing against an off-target effect of the drug. As a further test, coadministration of higher concentrations of erlotinib instead of time-staggered doses was also tested, without observing increased apoptosis (FIG. 9C). Taken together, these data indicate that enhanced cell death observed using time-staggered erlotinib-doxorubicin combinations is directly mediated by sustained EGFR inhibition.

Figures 2A, 2B, 2C, 2D, 2E, 2F, 2G, 2H, 2I, 2J, 2K:
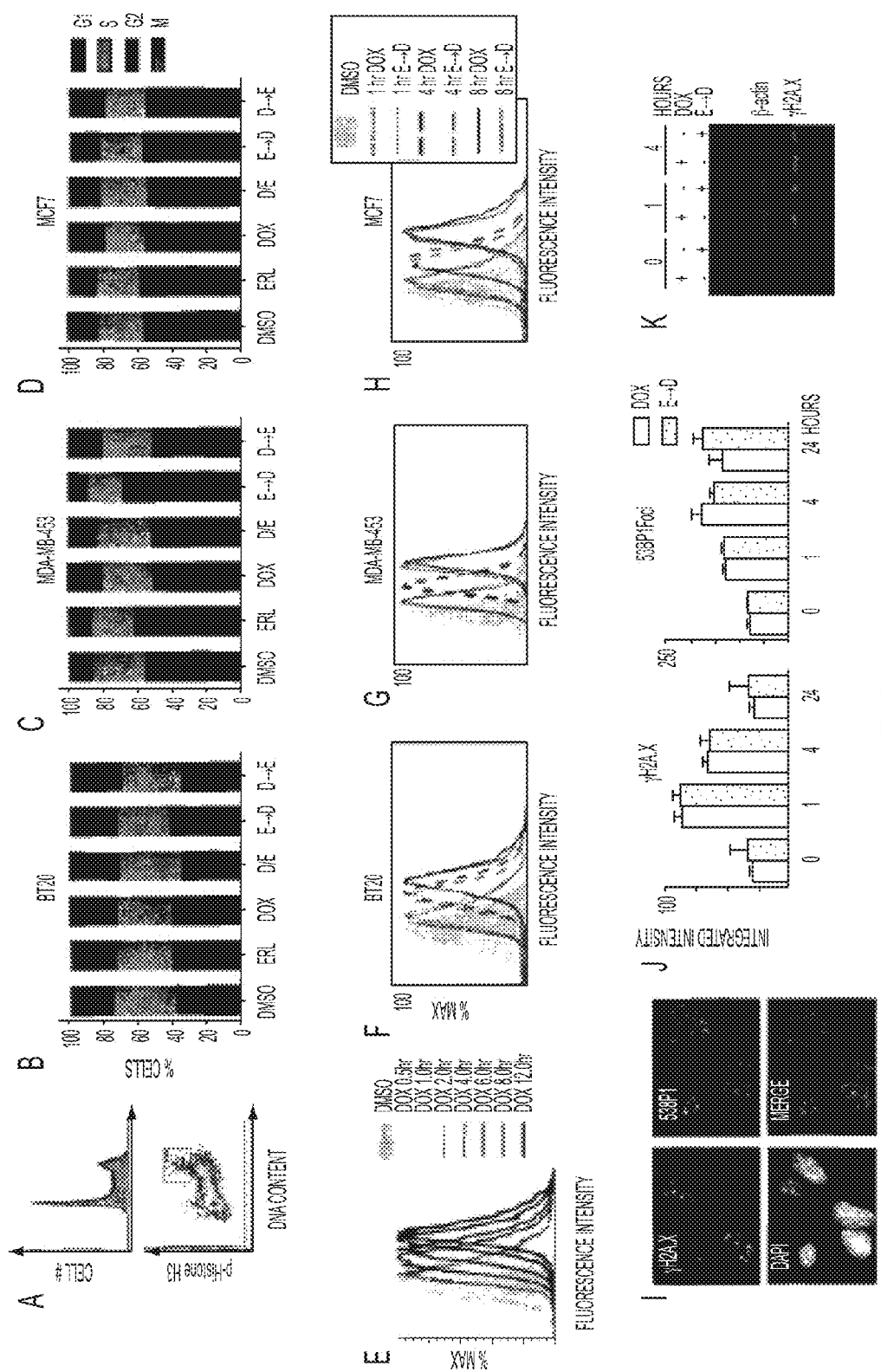
FIGS. 2A-2K. Prolonged Treatment with Erlotinib Does Not Change Cell-Cycle Profile, Doxorubicin Influx/Efflux, or the Level of DNA Damage (A-D) Quantitative cell-cycle analysis. DNA content and the percentage of mitotic cells were measured by FAGS. (A) Example FAGS plots from untreated BT-20 cells. (8-D) Cell-cycle stage quantified from three experiments, each performed in duplicate. Cells were treated as in FIG. 1, and data were collected at 6, 8, 12, 24, and 48 hr after OOX treatment. B hr data shown for each cell type. (E-H) Doxorubicin retention measured by flow cytometry. (E) Sample time course of BT-20 cells treated with 10 μM DOX for the indicated times. (F-H) Cells treated with doxorubicin or pretreated with erlotinib for 24 hr prior to DOX (E→D). Cells were collected at 1, 4, or 8 hr after DOX exposure as indicated, and internal doxorubicin fluorescence was measured. (I and J) Quantitative microscopy of the early DNA double-stranded break response. (I) Example image of cells treated with DOX for 1 hr and stained for yH2AX, 53BP1, or nuclear content (OAPI). (J) Integrated intensity per nucleus of yH2AX and 53BP1 foci was measured in BT-20 cells after the indicated treatments and times. Mean values±SO from triplicate experiments shown. (K) Western blot analysis of λH2AX in BT-20 cells. β-actin shown as a loading control.

Potential explanations for the increased sensitivity of cells to doxorubicin following sustained EGFR inhibition include modulation of cell-cycle progression, altered rates of doxorubicin influx/efflux, or changes in levels of DNA damage itself. To examine these, cell-cycle progression at five time points over 24 hr was monitored in the panel of breast cancer cell lines. Although doxorubicin and erlotinib altered cell-cycle dynamics depending on the cell type, cells that received both drugs had similar cell-cycle profiles regardless of the dosing regimen (FIGS. 2A-2D and 9D). In particular, there is no evidence that cells exposed to the ERL→DOX protocol accumulate in S/G2, the cell-cycle stage during which doxorubicin may be most effective. Thus, cell-cycle modulation cannot explain the unique efficacy of sequential drug exposure. Some membrane pumps can be modulated by EGFR inhibitors (Lopez, J. P., Wang-Rodriguez, J., Chang, C., Chen, J. S., Pardo, F. S., Aguilera, J., and Ongkeko, W. M. (2007). Gefitinib Inhibition of Drug Resistance to Doxorubicin by Inactivating ABCG2 in Thyroid Cancer Cell Lines. Arch. Otolaryngol. Head Neck Surg. 133, 1022-1027; Turner, J. G., Gump, J. L., Zhang, C., Cook, J. M., Marchion, D., Hazlehurst, 1., Munster, P., Schell, M. J., Dalton, W. S., and Sullivan, D. M. (2006). ABCG2 Expression, Function, and Promoter Methylation in Human Multiple Myeloma. Blood 108, 3881-3889) and are responsible for multidrug resistance in at least some breast cancers (Woehlecke, H., Osada, H., Herrmann, A., and Lage, H. (2003). Reversal of breast cancer resistance protein-mediated drug resistance by tryprostatin A. Int. J. Cancer 107, 721-728). the intracellular accumulation of doxorubicin was measured by flow cytometry and it was found that prior treatment with erlotinib did not alter the intracellular doxorubicin concentration (FIGS. 2E-2H). Next, as pharmacodynamic markers of doxorubicin action, two indicators of DNA double-stranded breaks: phosphorylation of histone H2AX at S139 and formation of 53BP1-containing nuclear foci were measured. Both assays showed similar responses across all treatment conditions (FIGS. 2I-2K). Taken together, these data indicate similar levels of DNA damage and early DNA damage-related signaling in DOX- and ERL→DOX-treated cells independent of the efficacy of the combination in cell killing.

Figures 3A, 3B, 3C:
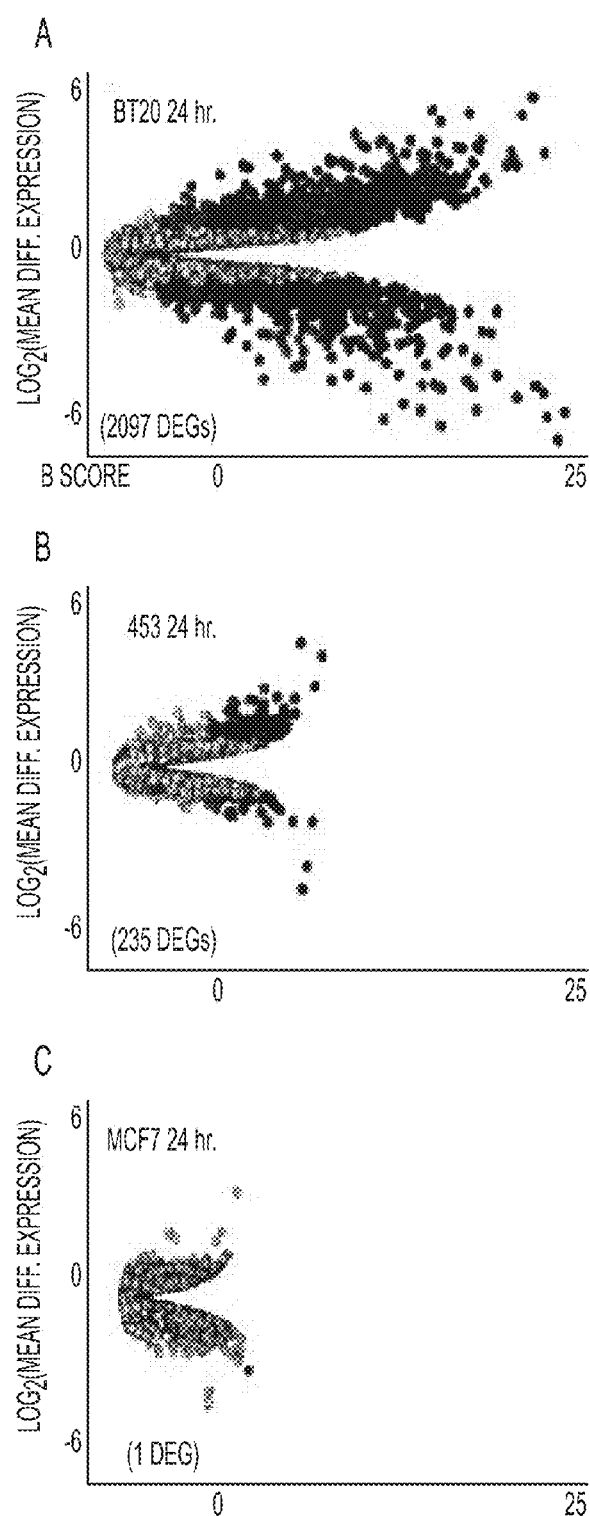
FIGS. 3A-3H. Triple-Negative BT-20 Cells Are Driven by Oncogenic EGFR Signaling (A-C) DEGs following erlotinib treatment for 24 hr versus untreated cells. Cut-off for DEG was ≥2-fold change and a p value≤0.05 (genes that meet both criteria are colored red). 8 score is the log of the odds of differential expression. (D) DEGs classified using GeneGO "pathway maps." Heatmap (left) colored according to −log(p value); (right) p value cut-off was 0.05 (dotted red line). (E and F) Microarray analysis using GSEA reveals loss of oncogene signatures in BT-20 cells after sustained EGFR inhibition. Ras oncogenic signature and false discovery rate (FDR)-adjusted p values are shown in (E). Eleven oncogenic signatures from the Molecular Signatures Database (MSigDB) are shown in (F). Boxes are colored according to normalized enrichment score (NES) (G). Illustrates soft agar colony formation in control and treated cell (H).
Figure 4A:
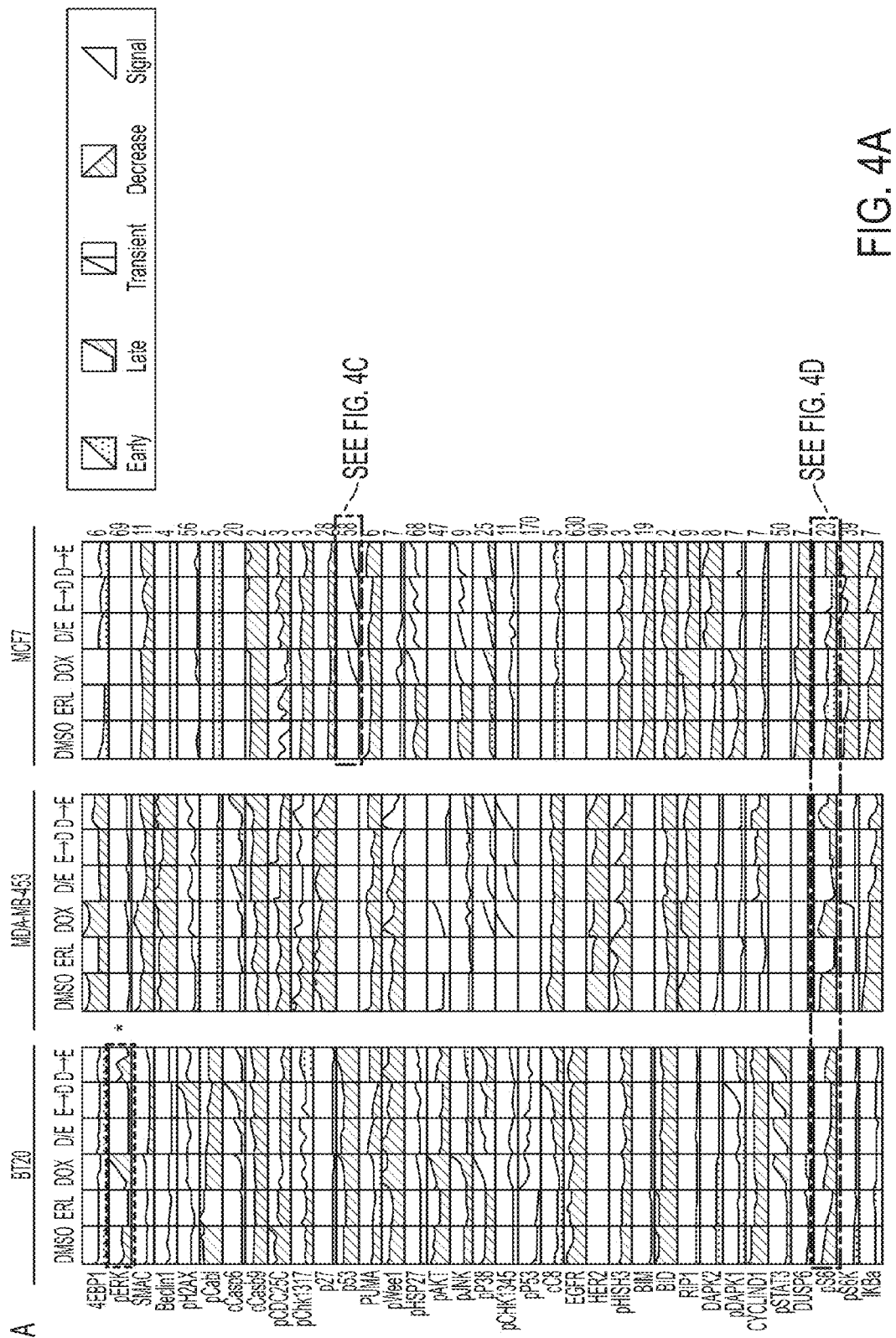
FIGS. 4A-4E. A Systems-Level Signal-Response Data Set Collected Using a Variety of High-Throughput Techniques (A-D) (A) The complete signaling data set for three different breast cancer subtypes following combined EGFR inhibition and genotoxic chemotherapy treatments as in FIG. 1. Each box represents an 8 or 12 point time course of biological triplicate experiments. Time course plots are colored by response profile, with early sustained increases in signal colored green, late sustained increases colored red, and transient increases colored yellow. Decreases in signal are colored blue. Signals that are not significantly changed by treatment are shaded gray to black with darkness reflecting signal strength. Numbers to the right of each plot report fold change across all conditions and/or cells. (B) Sample detailed signaling time course from (A), highlighted by dashed box and asterisk, showing p-ERK activation in BT-20 cells. Mean values±SD of three experiments are shown. (C) Forty-eight-sample western blots analyzed using two-color infrared detection. Each gel contained an antibody-specific positive control (P) for blot-to-blot normalization. The example shown is one of three gels for total p53 in MCF7 cells (p53 in green; J1-actin in red). (D) Reverse-phase protein lysate microarrays were used to analyze targets of interest when array-compatible antibodies were available. The slide shown contains approximately 2500 lysate spots (experimental and technical triplicates of all of our experimental samples, and control samples used for antibody calibration), probed for phospho-56. (E) The complete cellular response data set, colored as in (A).
Figures 4B, 4C, 4D, 4E:
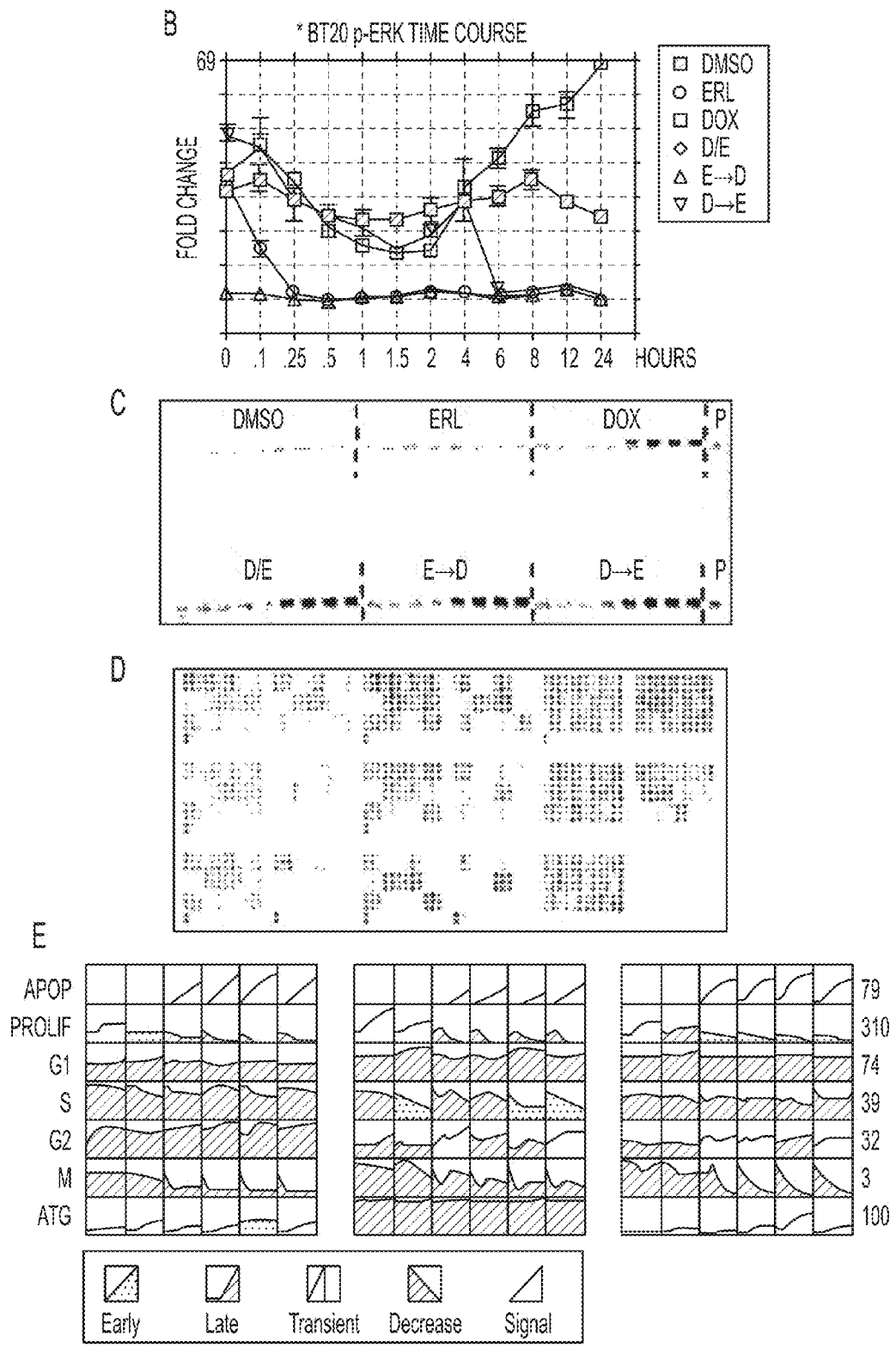
Figures 10A, 10B, 10C, 10D, 10E:
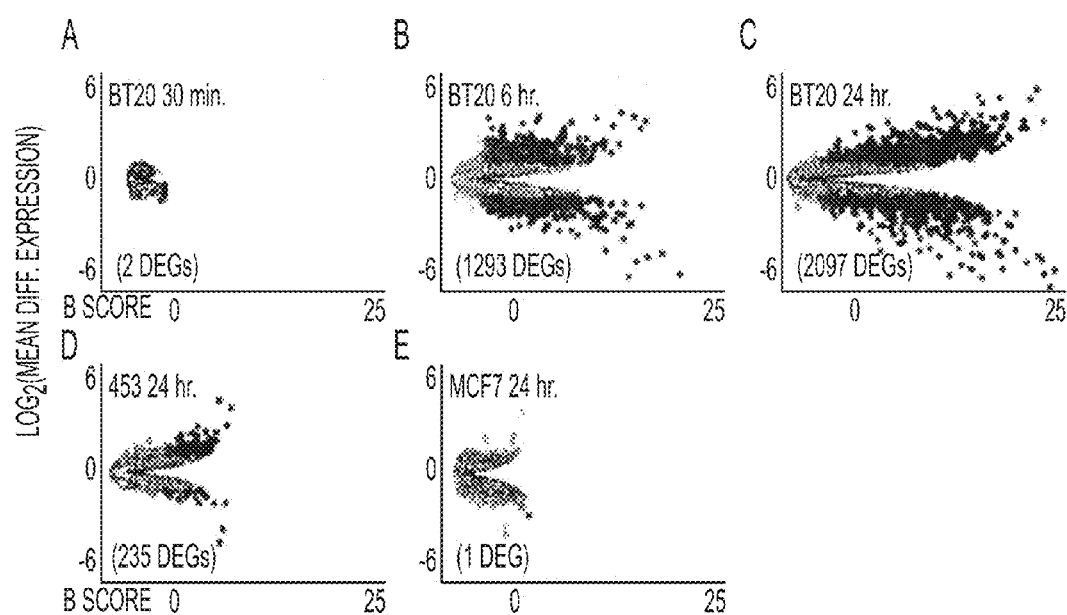

The absence of demonstrable changes in cell-cycle states, intracellular doxorubicin concentrations, or doxorubicin-induced DNA damage suggested that prolonged EGFR inhibition necessary for effective tumor cell killing might result from rewiring of the signaling networks that control responses to genotoxic stress. To investigate this idea, changes in gene expression in cells treated with erlotinib alone were measured. In triple-negative BT-20 cells, EGFR inhibition for 30 min resulted in few differentially expressed genes (DEGs) (FIG. 10A). Following 6 hr of erlotinib treatment, however, more than 1,200 DEGs were observed, and following 24 hr of treatment, when doxorubicin sensitivity was maximally enhanced, more than 2,000 DEGs (FIGS. 3A and 10B). By comparison, in the HER2+ MDA-MB-453 cells, which were desensitized to doxorubicin by erlotinib exposure, only 235 DEGs were observed following 24 hr exposure to erlotinib, and in hormone-sensitive MCF7 cells, only one gene was significantly altered (FIGS. 3B and 3C). Thus, the triple-negative BT-20 cells exhibited progressive and large-scale changes in gene expression following EGFR inhibition that were not observed in cell lines insensitive to the time staggered ERL→DOX combination.

Figure 3D:
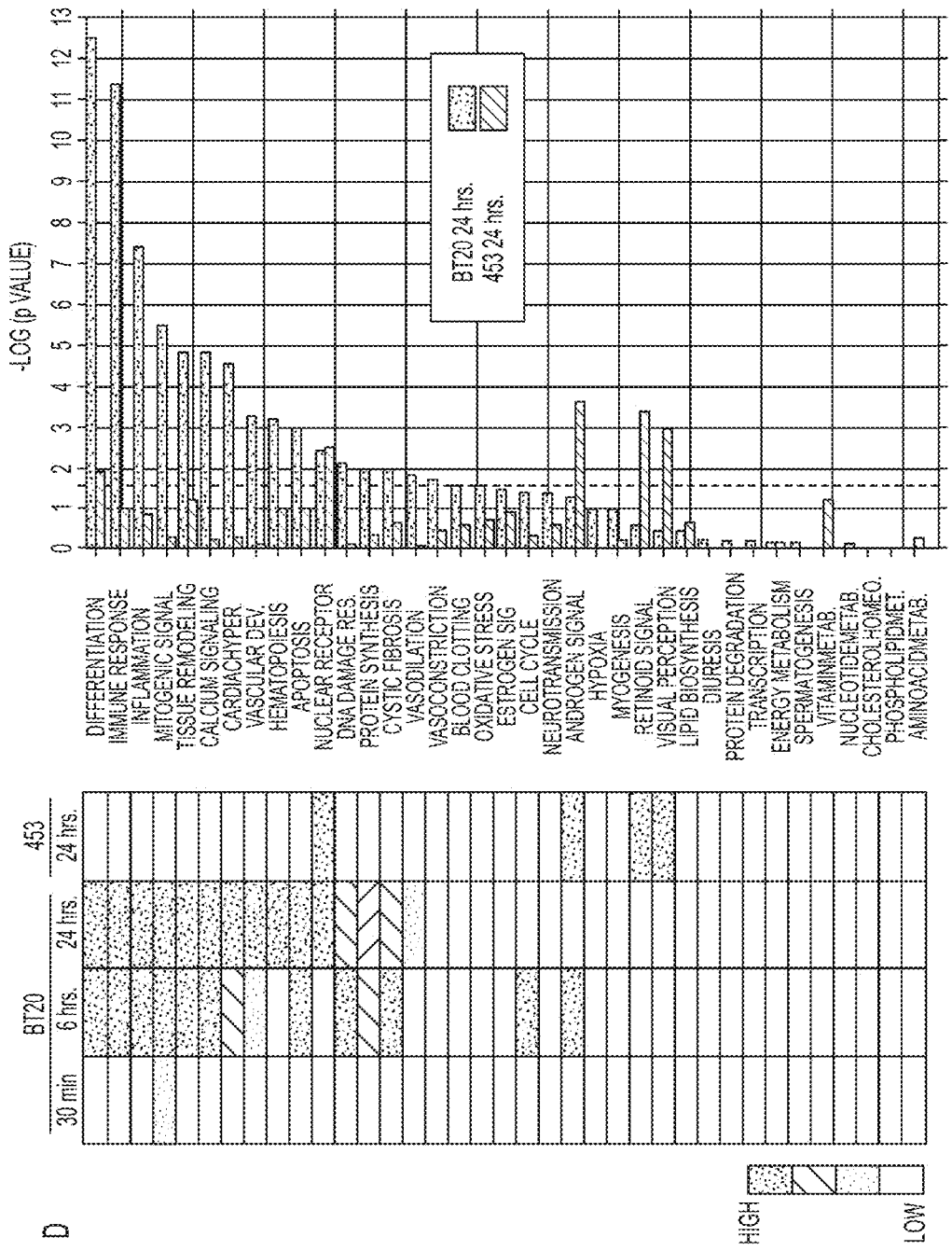
Figures 3E, 3F, 3G:
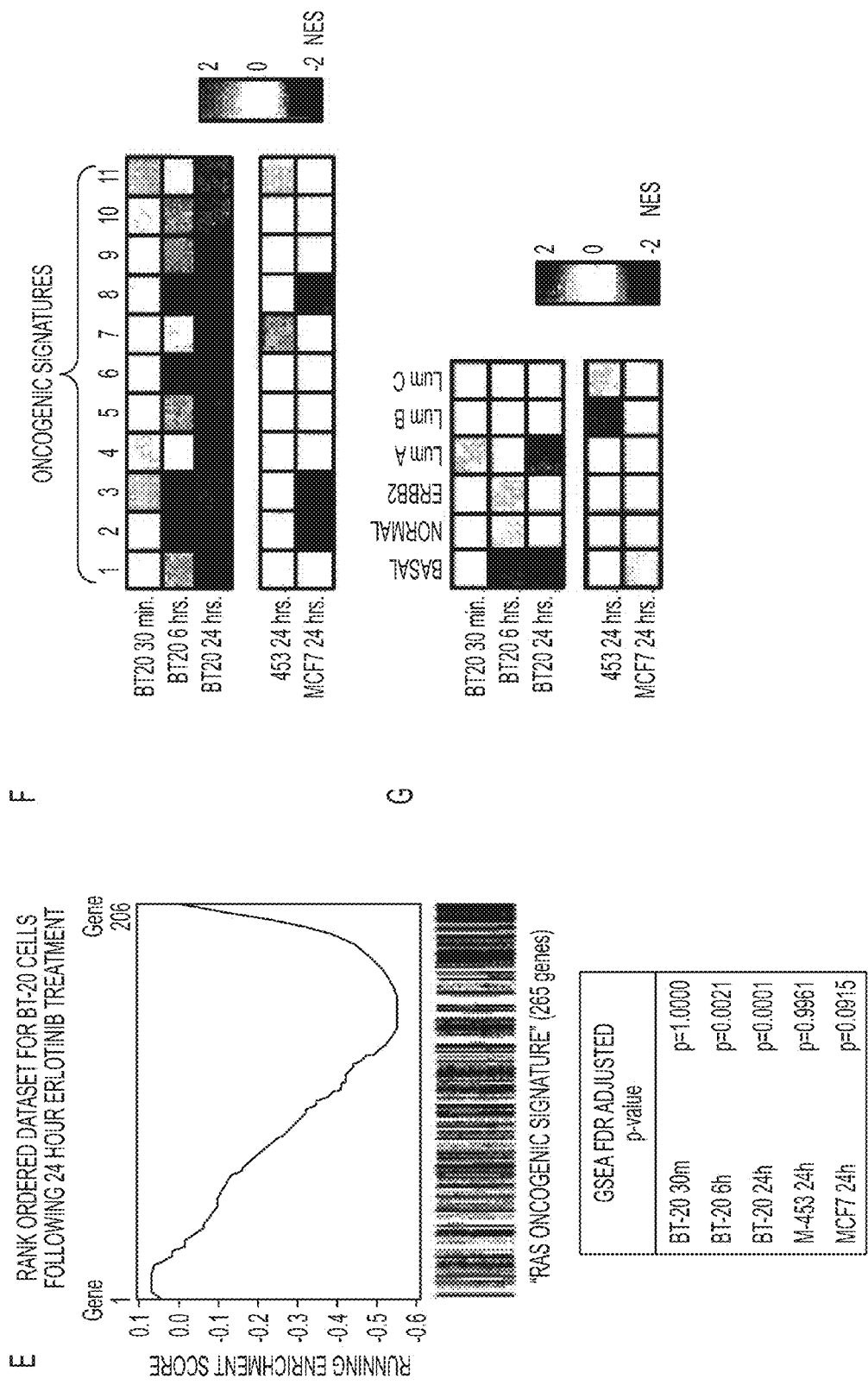

To examine which cellular processes were altered by long-term erlotinib treatment, DEGs in BT-20 cells were categorized by cellular process according to the GeneGO pathway annotation software (Ekins, S., Nikolsky, Y. Bugrim, A., Kirillov, E., and Nikolskaya, T. (2007). Pathway mapping tools for analysis of high content data. Methods Mol. Biol. 356, 319-350). Significant changes were observed in 16 of 34 GeneGO cellular networks, including those that mediate the DDR, apoptosis, and inflammation (FIG. 3D). In contrast, DEGs in MDA-MB-453 were not only fewer in number, but also lay in networks that did not overlap with those altered in BT-20 cells (FIG. 3D). Gene expression data was further analyzed using gene set enrichment analysis (GSEA), a tool for identification of enrichment or depletion of defined gene expression signatures within a rank-ordered gene list (Subramanian et al., Proc. Natl. Acad. Sci. USA 102, 15545-15550 2005). The most statistically significant changes in BT-20 cells upon sustained erlotinib exposure were loss of the Ras and MYC oncogenic signatures (FIG. 3E). These signatures were not significantly altered in MDA-MB-453 or MCF7 cells treated with erlotinib for 24 hr or in BT-20 cells exposed to erlotinib for 30 min (FIG. 3E). Within the GSEA molecular signatures database, there exist 11 oncogenic signatures (Subramanian et at., 2005). GSEA of EGFR-inhibited BT-20 cells showed a similar depletion pattern for all 11 oncogenic signatures (FIG. 3F). These changes were not consistently observed in either MDA-MB-453 cells or MCF7 cells following exposure to erlotinib.

Figure 3H:
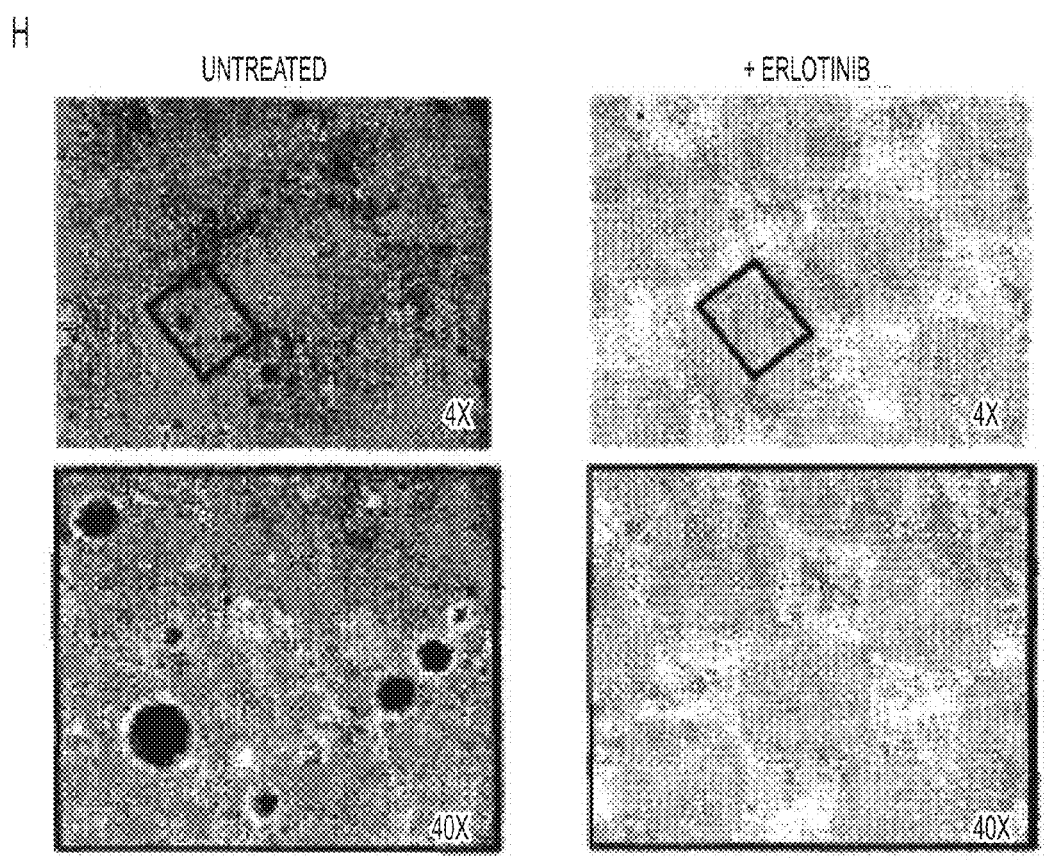

Distinct gene expression patterns have been used to define breast cancer subtypes. BT-20 cells, like most triple-negative cells, display a "basal-like" gene expression signature (Neve et al., 2006). Strikingly, analysis of the expression data set revealed that chronic erlotinib treatment of BT-20 cells caused progressive time-dependent loss of basal-like gene expression with concomitant gain in luminal A-like gene expression, a breast cancer subtype with the least aggression and best overall prognosis (FIG. 3G). In contrast, no such switch in breast cancer subtype patterns of gene expression was observed in HER2-overexpressing MDA-MB-453 cells or hormone-sensitive MCF7 cells following erlotinib exposure. These expression data indicate that the oncogenic potential of BT-20 cells is maintained by chronic EGFR-driven patterns of gene expression and that this cell state could be remodeled through sustained inhibition of EGFR. To directly test this, the ability of BT-20 cells to form colonies in soft agar, a classic test of transformation that typically shows good correlation with tumorigenic potential in vivo (Montesano, A., Drevon, C., Kuroki, T., Saint Vincent, L., Handleman, S., Sanford, K. K. DeFeo, D. and Weinstein, 1.8. (1977). Test for Malignant Transformation of Rat Liver Cells in Culture: Cytology, Growth in Soft Agar, and Production of Plasminogen Activator. J. Nail. Cancer Inst. 59, 1651-1658) was used. Consistent with the predictions derived from the GSEA, sustained EGFR inhibition with erlotinib potently inhibited soft agar colony formation (FIG. 3H).

Creation of a Data-Driven Model for Combined EGFR Inhibition/DNA Damage

Figure 11A:
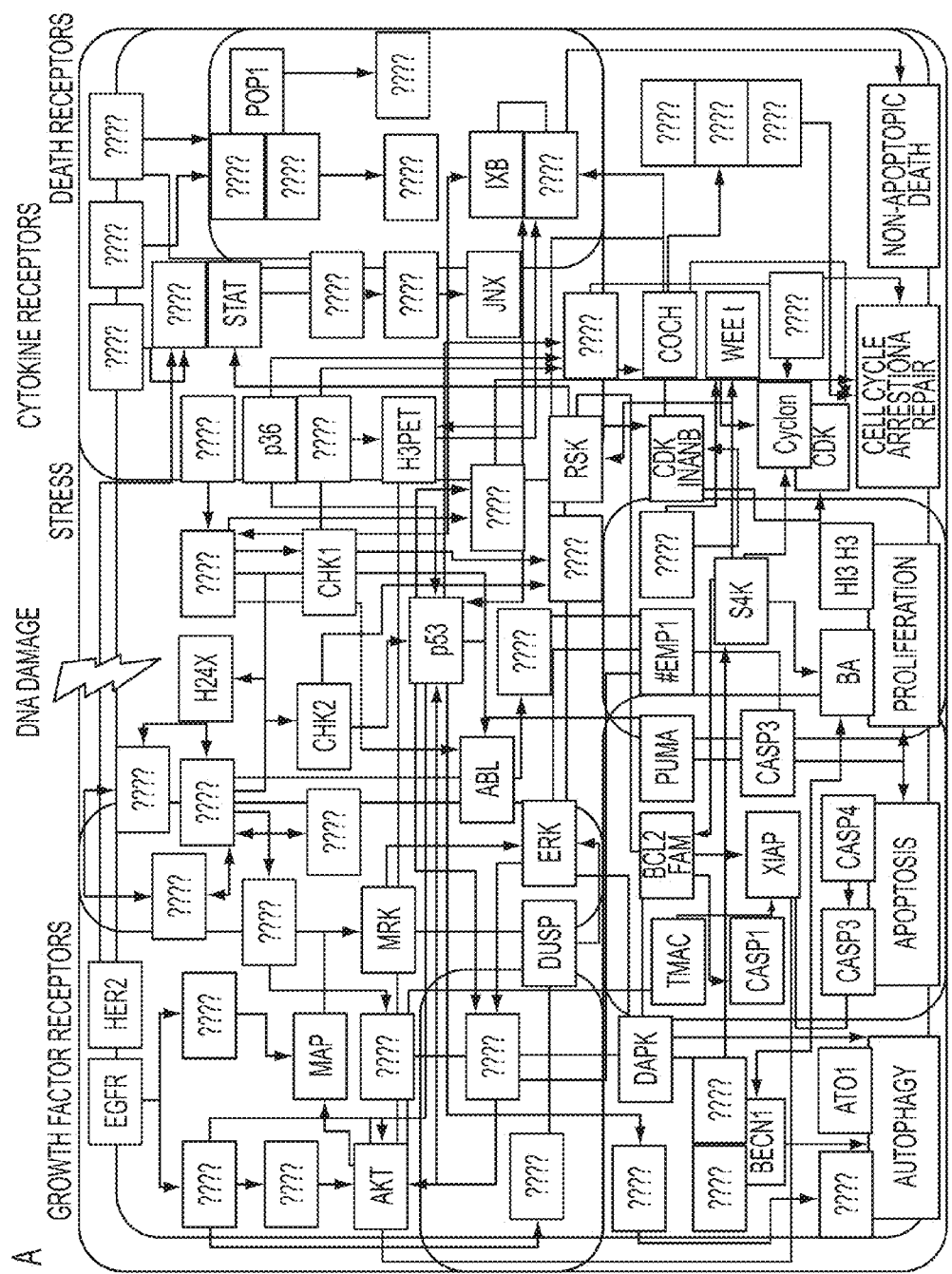
Figures 11B, 11C, 11D:
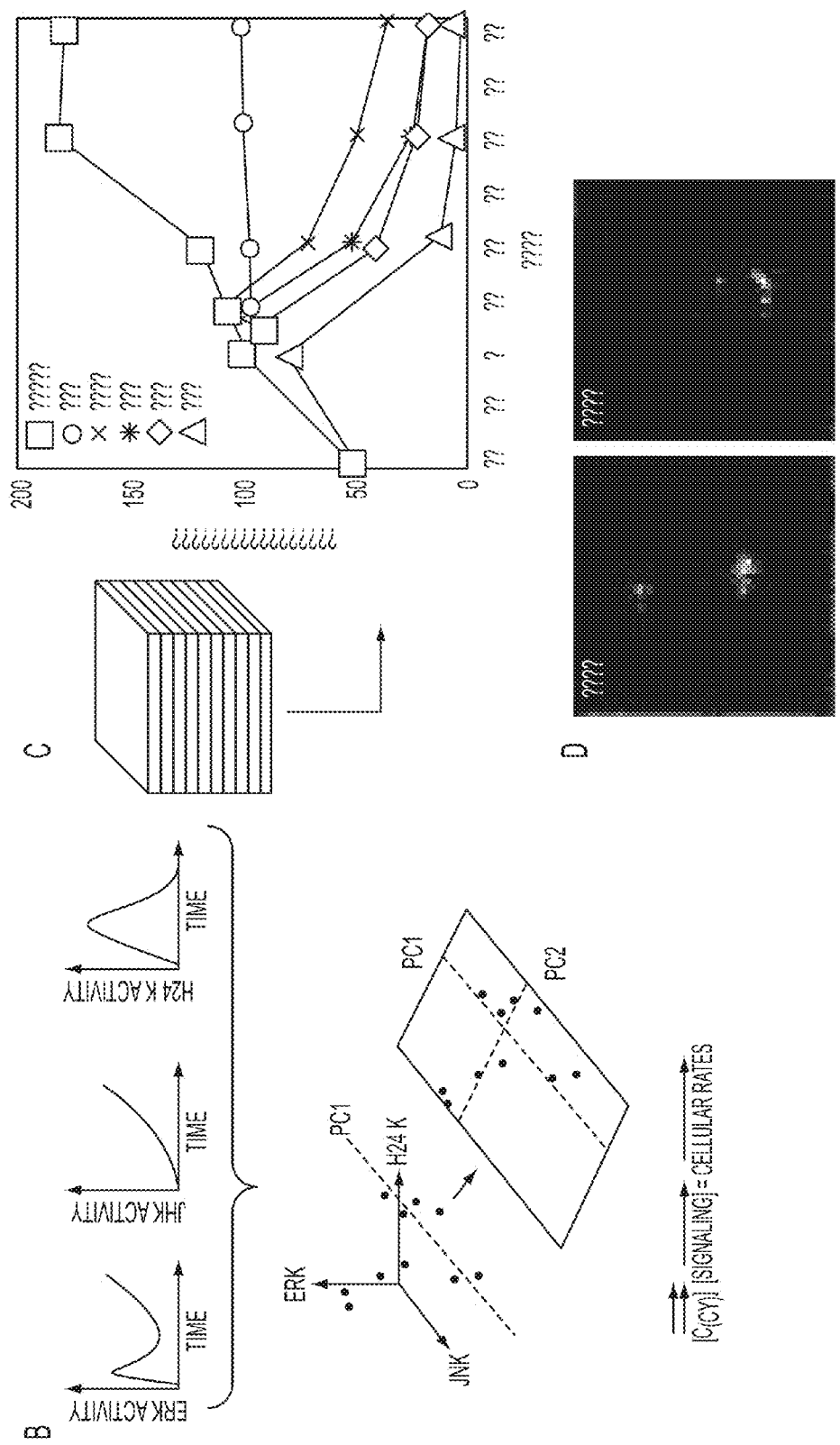
Figures 11E, 11F:
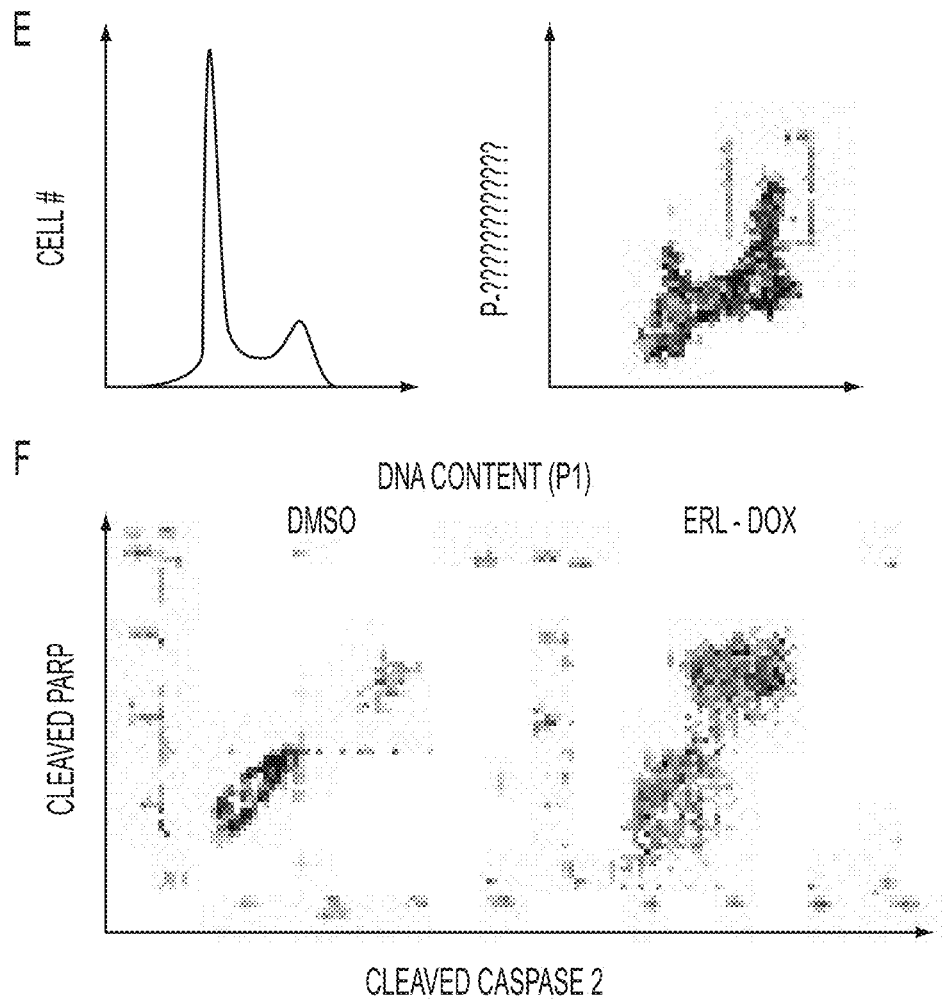

To better understand the biochemical changes in signaling that accompany time-staggered ERL→DOX treatment, quantitative high-throughput reverse-phase protein microarrays and quantitative western blotting were used to measure the levels or activation states of 35 signaling proteins within multiple signaling pathways at 12 time points following exposure to erlotinib and doxorubicin both individually and in combination (FIGS. 4A-4D and see FIG. 11 for a description of the selection of 35 proteins for analysis) (MacBeath, G. (2002). Protein microarrays and proteomics. Nat. Genet. Suppl. 32, 526-532). Oncogenic signaling networks typically exhibit multiple levels of feedback and cross-talk with other networks, rendering single protein measurements ineffective in predicting complex cellular responses to drugs such as those leading to DNA damage-induced apoptosis (Fitzgerald, J. B., Schoeberl, B., Nielsen, U. B. and Sorger, P. K. (2006). Systems biology and combination therapy in the quest for clinical efficacy. Nat. Chem. Bioi. 2, 458-466). A multifactorial data-driven mathematical model relating signaling "inputs" to phenotypic "outputs." Was constructed. In addition to examining signaling pathways known to contribute to the DDR, the list of differentially expressed genes (FIG. 3) was used to identify other proteins that might function as critical signaling nodes. This DEG-expanded list of signaling proteins extends far beyond the canonical components of the DDR, including proteins involved in apoptotic and nonapoptotic death, growth and stress responses, and cytokine/inflammatory signaling (FIG. 11A). Specific proteins, whose measurement was motivated by gene expression data, included Bcl2-interacting mediator of cell death (BIM), BH3-interacting domain (BID), capase-8, 4E-BP1, S6K, Stat3, DUSP6, and inhibitor of kappa B (IKB). Phenotypic responses, including cell-cycle arrest and progression, autophagy, and apoptotic and nonapoptotic cell death, were scored at six time points using luminescent microplate assays, flow cytometry, and automated microscopy (FIGS. 4E and 11C-11F). All signaling and phenotypic response measurements were performed in biological and experimental triplicate in BT-20, MDA-MB-453, and MCF7 cells. In total, this data set comprised more than 45,000 measurements of molecular signals and 2,000 measurements of cellular responses (FIGS. 4A and 4E), revealing many changes in cell state and phenotype associated with drug exposure.

Several mathematical modeling approaches were employed to relate signaling data to cell phenotypes. Initial modeling efforts used principal component analysis (PCA) to identify covariation between signals, whereas partial least-squares (PLS) regression was used to identify statistically significant covariation between molecular signals and corresponding cellular responses (FIG. 11B) (Janes and Yaffe, 2006). In both PCA and PLS modeling, vectors were constructed whose elements contained quantitative measures of the level, state, and/or activity of specific signaling proteins. The vectors were then reduced to a set of principal components, calculated so that each additional PCA or PLS dimension maximally captures information not captured by preceding components. This process was iteratively repeated until additional principal components ceased to capture meaningful data, as judged relative to experimental noise.

Figures 5A, 5B, 5C, 5D, 5E, 5F:
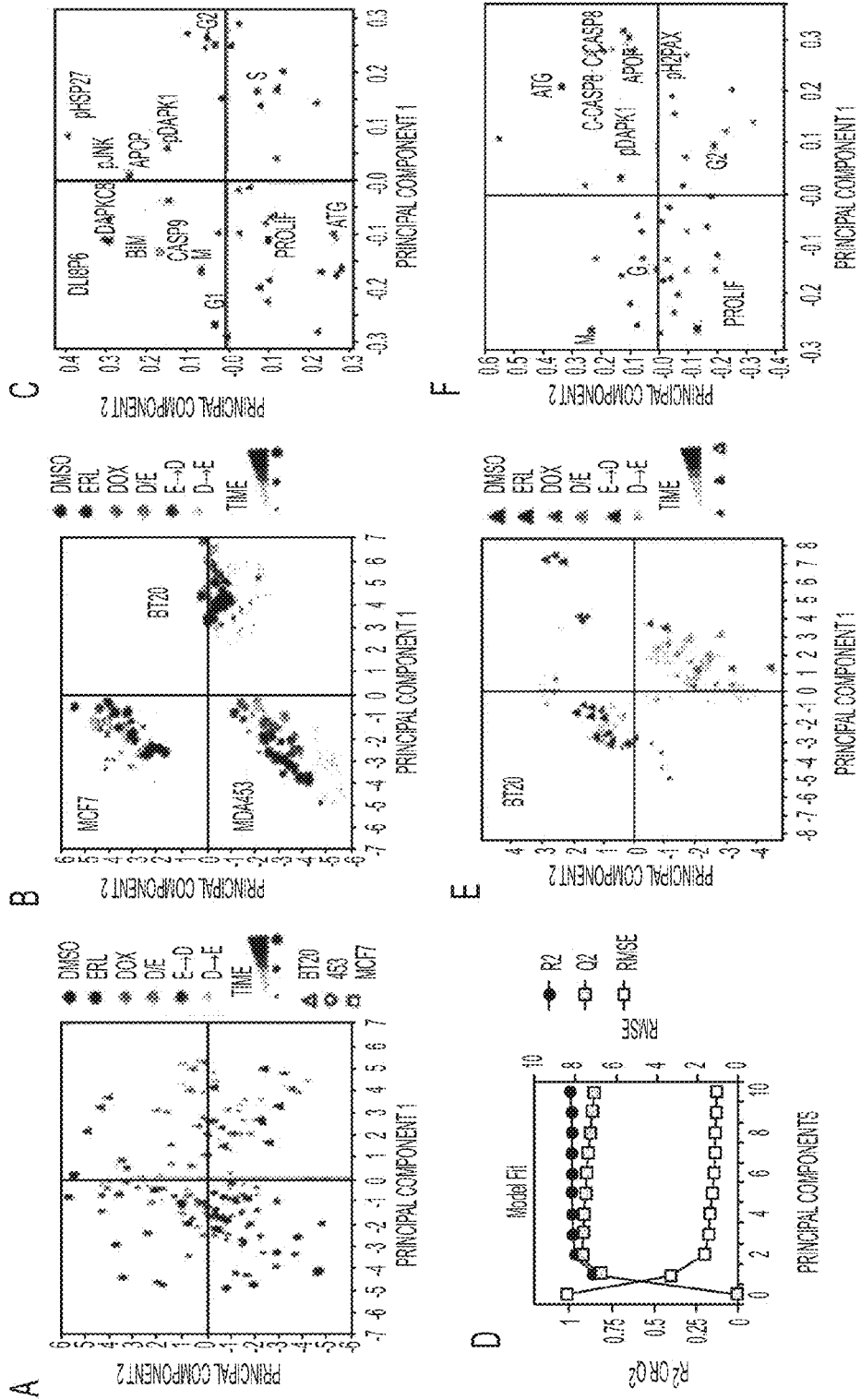
FIGS. 5A-5I. A PLS Model Accurately Predicts Phenotypic Responses from Time-Resolved Molecular Signals (A) Principal components analysis of covariation between signals. Scores plot represents an aggregate measure of the signaling response for each cell type under each treatment condition at a specified time, as indicated by the colors and symbols in the legend. (B and C) Scores and loadings for a PLS model. (B) Scores calculated and plotted as in (A), except the principal components now reflect covariation between signals and responses. (C) PLS loadings plotted for specific signals and responses projected into principal component space. (0-1) BT-20 cell line-specific model calibration. (D) A 2, a2, and AMSE for BT-20 models built with increasing numbers of principal components. (E and F) Scores and loadings plots, respectively, for a two-component model of BT-20 cells. (G-1) Apoptosis as measured by flow cytometry or as predicted by our model using jack-knife cross-validation. A 2 reports model fit, and a2 reports model prediction accuracy. (G) Final refined model of apoptosis in BT-20. (H) BT-20 model minus targets identified as DEGs in microarray analysis. (I) Model using only the top four signals: c-caspase-8, c-caspase-6, p-DAPK1, and pH2AX.
Figures 12A, 12B, 12C, 12D, 12E, 12F, 12G, 12H, 12I, 12J, 12K, 12L:
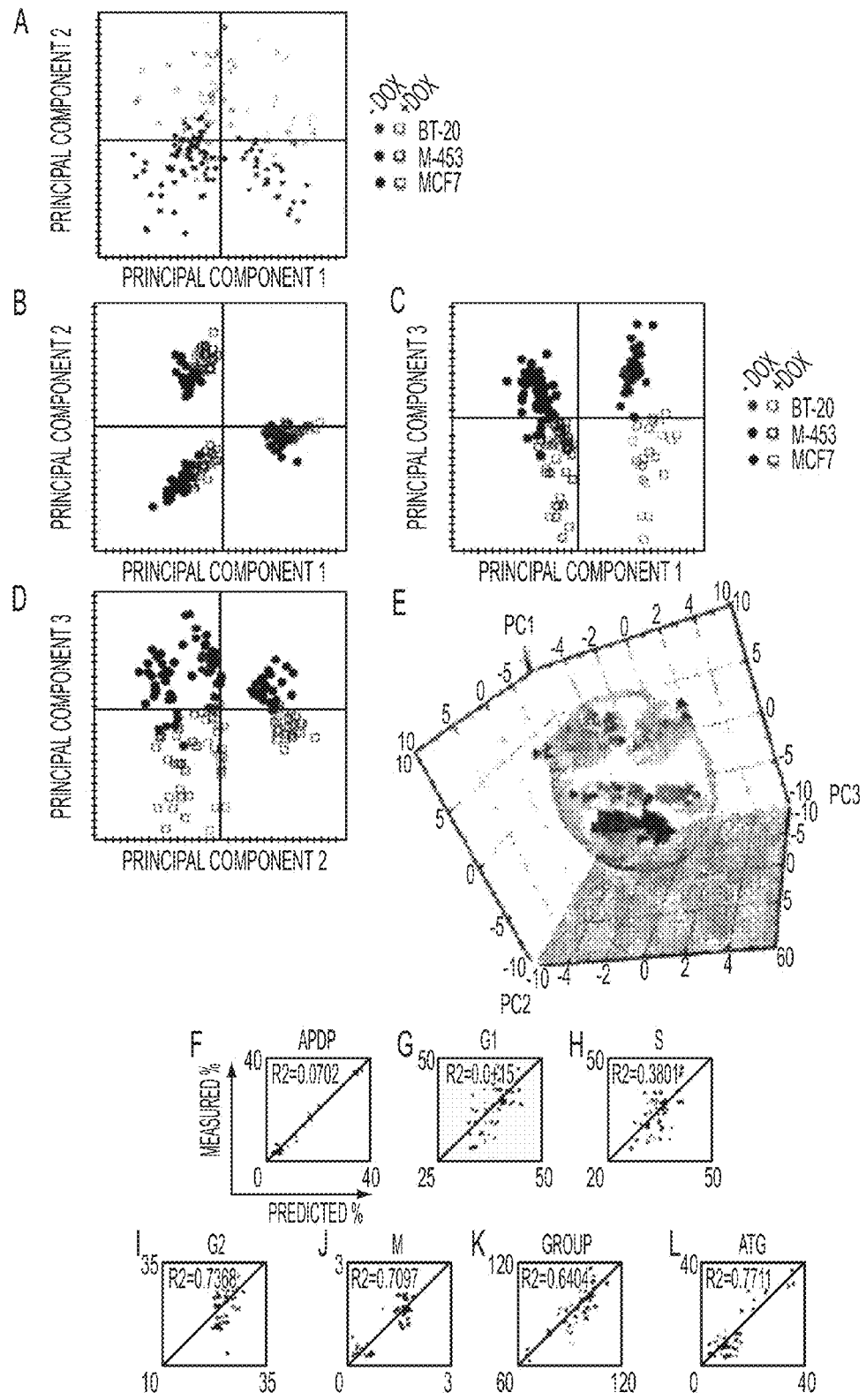
Figures 13A, 13B, 13C, 13D, 13E, 13F:
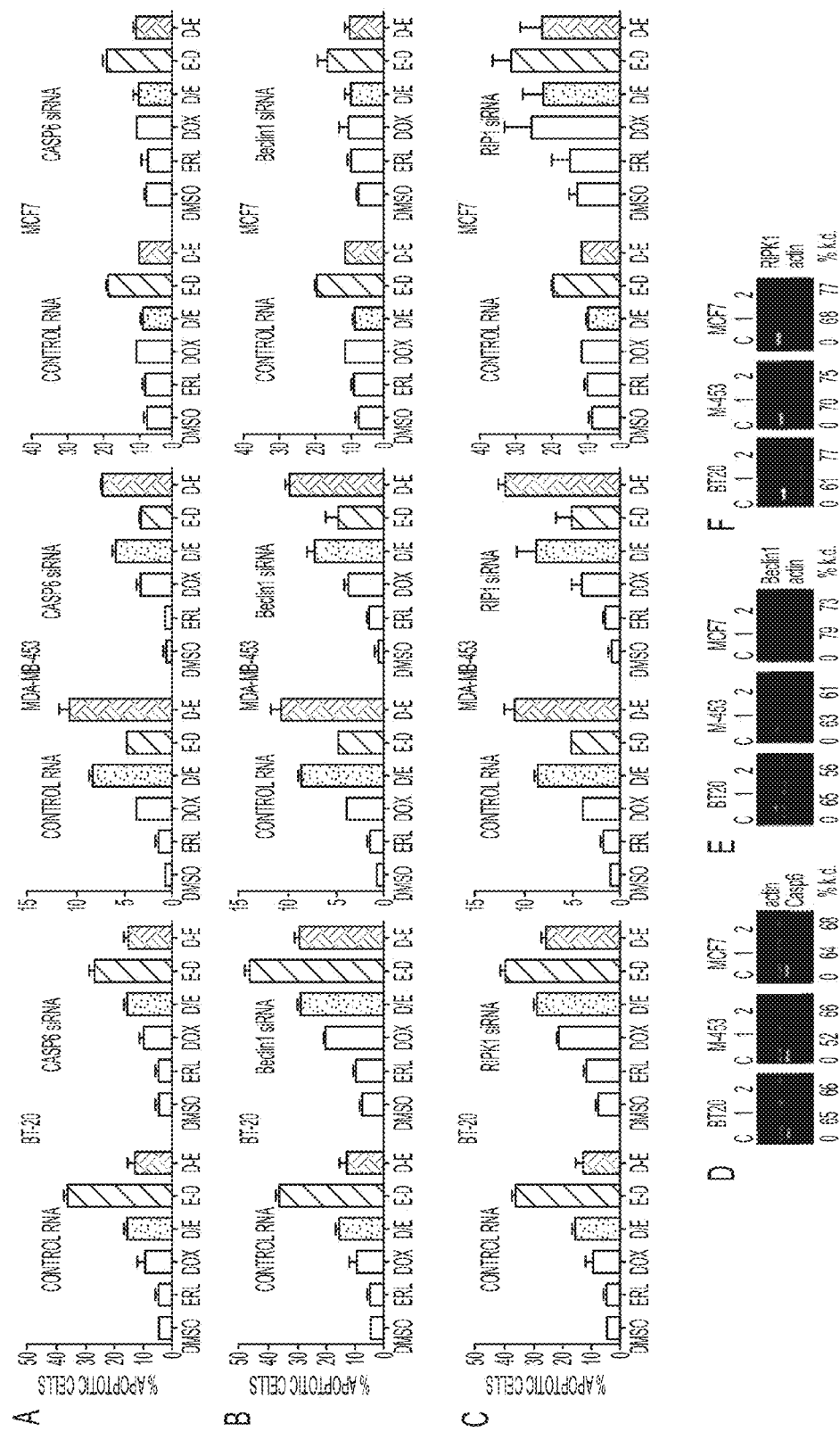

Following PCA, multiplex data from MDA-MB-453 cells projected negatively along principal component one (PC1), data from BT-20 cells projected positively along PC1, and MCF7 data were largely neutral (FIGS. 5A and 12A). Thus, the first principal component captured cell type-specific variance in the data. In contrast, data from all cell types projected similarly along/PC2 but in a manner that was drug dependent. Data from DMSO- or erlotinib-treated cells not exposed to doxorubicin projected negatively along PC2, whereas data from cells cotreated with doxorubicin and erlotinib or exposed sequentially to ERL→DOX projected positively along PC2. Finally, data from cells treated with doxorubicin alone or DOX→ERL were largely neutral along PC2. Thus, the second principal component; captured signaling variance from treatment-specific modulation of the signaling networks regardless of cell type (FIGS. 5A and 12A). These data suggest that, although significant differences in the state of the networks exist between cell lines, the drugs that applied modulated signaling networks were applied in similar ways across all lines examined. PLS analysis linking signals to responses gave similar results, with differences between the cell lines now captured in both PC1 and PC2 and treatment-specific variance emerging in the third principal component, PC3 (FIGS. 5B and 12B-12E). The expected differences observed between these cell types, captured by both PCA and PLS analyses, confirm that the measured signaling molecules can be used to define both the cell-type-specific and drug treatment-specific differences between these cells. Based on these cell-type-specific differences in the global PCAIPLS model, models for each cell line in isolation were built, focusing primarily on triple-negative BT-20 cells. To optimize the BT-20 PLS model, fitness measures such as $R^2$ (percent of variance captured by model), $O^2$ (percent of variance predicted by the model using a leave-one-out cross-validation approach), and root-mean-square error (rmse; the mean deviation between model and data) were compared across models containing increasing numbers of principal components. With BT-20 data alone, >97% of the variance linking signals to responses under different conditions of drug treatment was captured by two principal components. Incorporation of additional components actually reduced the predictive ability of the model (FIG. 5D), a common finding reflecting the addition of noise when components with little predictive value are added. Similar trends were observed for each of the other cell lines.

To derive molecular understanding from the models, the loading vectors (i.e., individual signals and responses) were projected into PLS component space. It was observed a strong anticorrelation between the apoptotic and proliferative responses (FIGS. 5C and 5F) that was captured by the first principal component in the BT-20 model (FIG. 5F) and by the second principal component in the aggregate cell line model (FIG. 5C). To further test model quality, each measured cellular response was compared in isolation to that predicted by the model using jack-knife-based cross-validation (FIGS. 12F-12L). The model was particularly accurate at predicting apoptosis following treatment (FIG. 5G) and was moderately good at predicting proliferation and autophagy (FIGS. 12K and 12L). Other responses (G1, G2, and S) were not predicted as accurately, likely due to the limited dynamic range in our cell-cycle response data set (FIGS. 12G-12J).

Figures 5G, 5H, 5I:
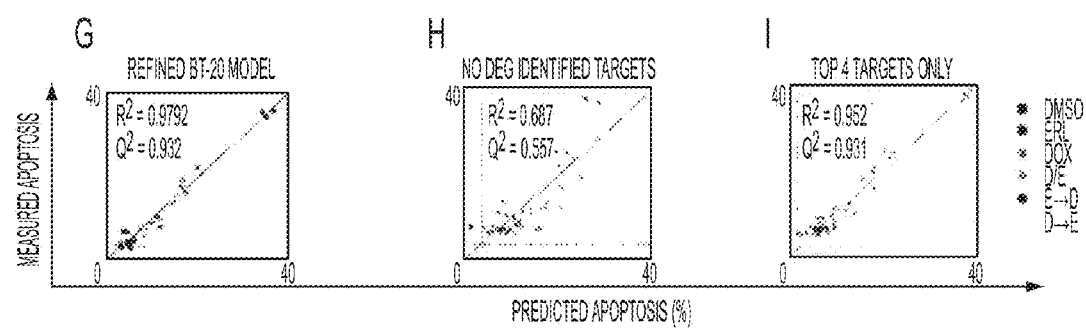
Figure 6A:
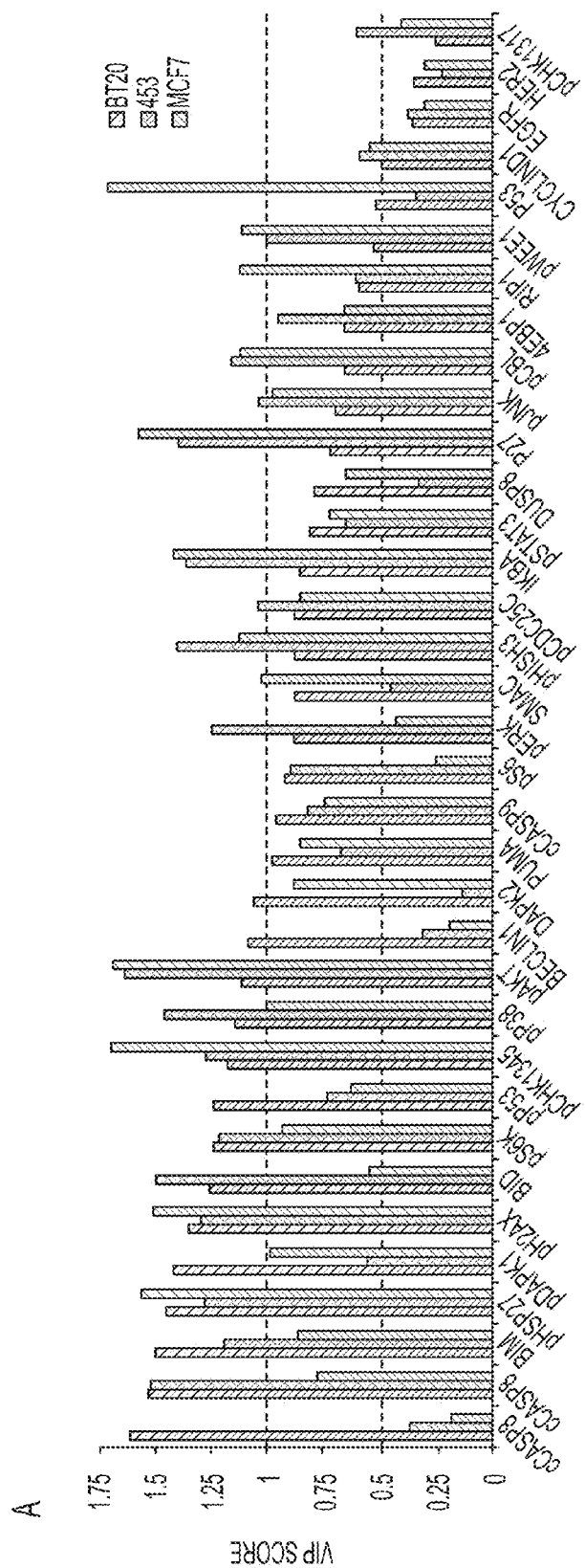
FIGS. 6A-6G. Enhanced Sensitivity to Doxorubicin Is Mediated by Caspase-8 Activation (A) VIP scores for predicting apoptosis plotted for each cell line-specific PLS model.
Figures 6B, 6C, 6D, 6E:
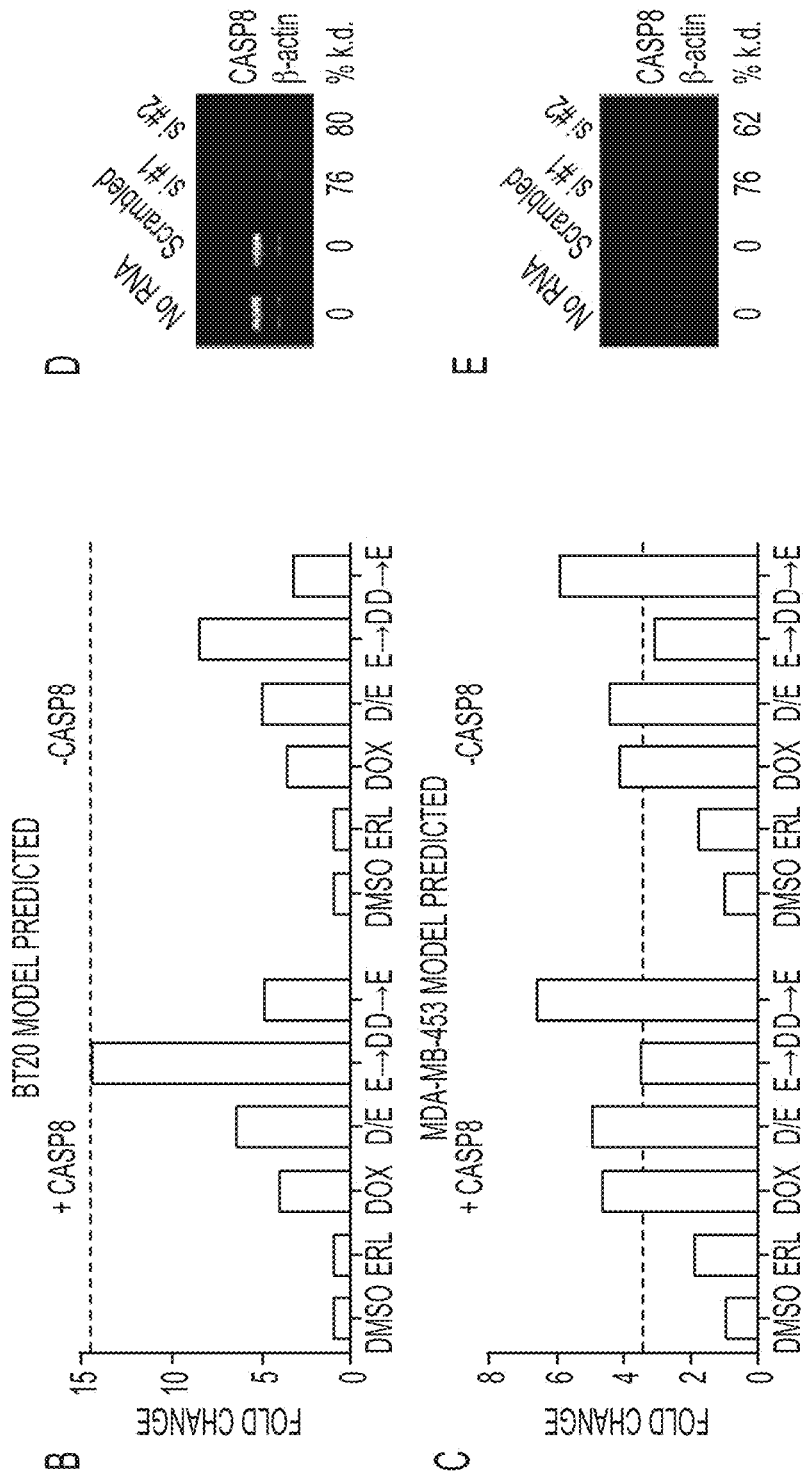
Figures 6F, 6G:
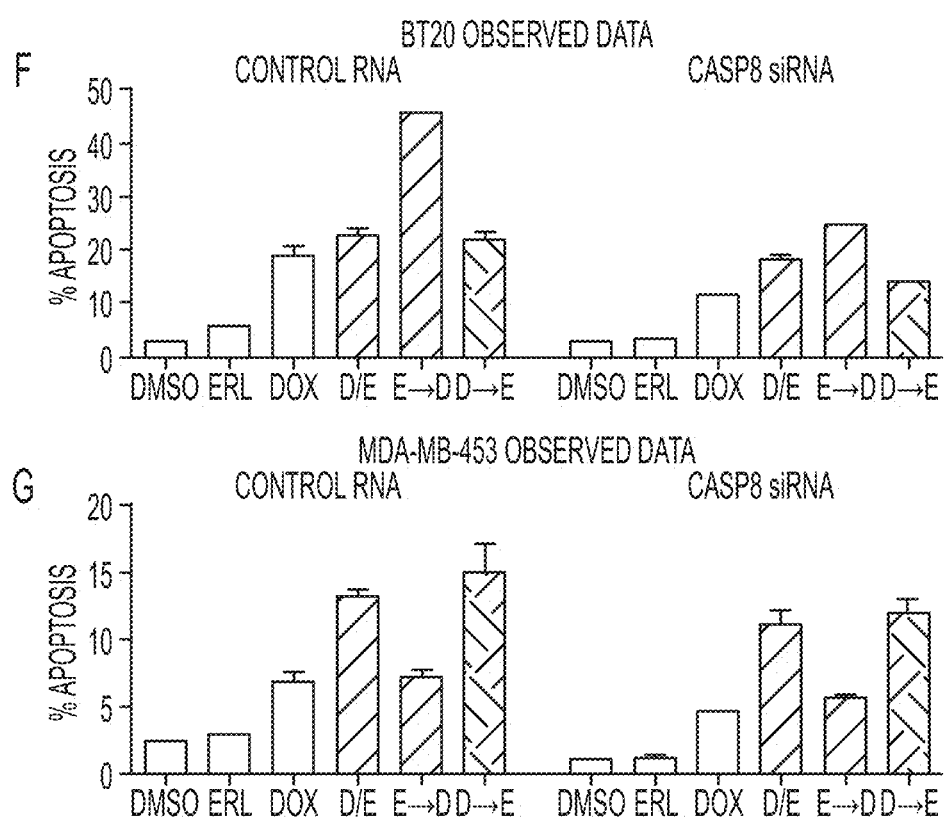

PLS Modeling Reveals that Chemosensitlzation Following Network Rewiring is Driven by Caspase-8 Activation Because PLS models of individual cell lines could accurately predict apoptosis, models to identify specific proteins or signals that might account for the enhanced sensitivity of BT-20 cells to doxorubicin following EGFR inhibition were analyzed. The BT-20 two-component PLS model identified four signals (cleaved caspase-8, cleaved-caspase-6, phospho-DAPK1, and phospho-H2AX) that were highly covariant with apoptosis (FIG. 5F). Remarkably, a model including only these four signals was just as accurate at predicting apoptosis as the complete 35-signal model (FIGS. 5G-5I). Of these signals, only pDAPK1 would have been identified using the aggregate cell line PLS model (FIG. 5C). It was reasoned that the enhanced sensitivity of BT-20 cells to doxorubicin, mediated by erlotinib pretreatment, likely involved one of these molecular signals. The "variable importance in the projection" (VIP) score was calculated and plotted for each signal (FIG. 6A). The VIP score reports the sum (over all model dimensions) of each variable x (molecular signals in this case), weighted by the amount of the cellular response y (apoptosis) explained by variable x. Strikingly, caspase-8, an initiator caspase in death receptor-mediated apoptosis, was the single most important variable for predicting apoptosis in BT-20 cells and was simultaneously among the least important variables in MDA-MB-453 and MCF7 cells. Caspase-8 has previously been implicated in cell death mediated by EGFR inhibition in other contexts (Kang, N., Zhang, J. H., Qiu, F., Tashiro, S., Onodera, s. and lkejima, T. (2010). Inhibition of EGFR signaling augments oridonin-induced apoptosis in human laryngeal cancer cells via enhancing oxidative stress coincident with activation of both the intrinsic and extrinsic apoptotic pathways. Cancer Lett. 294, 147-158; Morgillo, F., D'Aiuto, E., Troiani, T., Martinelli, E., Cascone, T.•De Palma, A., Orditura, M., De Vita, F., and Ciardiello, F. (2011). Antitumor activity of bortezomib in human cancer cells with acquired resistance to anti-epidermal growth factor receptor tyrosine kinase inhibitors. Lung Cancer 71, 283-290); however, erlotinib alone did not cause death in any of the cell types. Instead, apoptosis in these cells and the potential importance of caspase-8 resulted from their exposure to the genotoxic agent doxorubicin. In most cells, DNA damage activates cell-intrinsic apoptosis mediated through caspase-9 (FIG. 5C), not caspase-8 (Kim, A. (2005). Recent advances in understanding the cell death pathways activated by anticancer therapy. Cancer 103, 1551-1560). Thus, the strong influence of caspase-8 was unexpected. As an in silica test for the importance of caspase-8 in particular erlotinib/doxorubicin protocols, caspase-8 activity was set to zero in the model and all other variables left unchanged. The BT-20 model specifically predicted a dramatic decrease in the enhanced sensitivity to doxorubicin following sustained erlotinib treatment (FIG. 6B), with much smaller decreases in apoptosis occurring under all other treatments. In contrast, the apoptosis model for MDA-MB-453 cells predicted no change following loss of caspase-8 activity under any conditions (FIG. 6C). To test these predictions experimentally, two separate caspase-8 siRNAs were used in both BT-20 cells and MDA-MB-453 cells (FIGS. 6D and 6E). In excellent agreement with the model, knockdown of caspase-8 mitigated the enhanced cell death following erlotinib treatment in BT-20 cells while having minimal effect on apoptosis following other treatment combinations (FIG. 6F). Furthermore, caspase-8 knockdown had little effect on apoptosis in MDA-MB-453 under any condition (FIG. 6G). To further assess model predictions and evaluate the relative importance of caspase-8 in the enhanced doxorubicin-induced apoptosis, several other model-generated predictions were tested, including proteins predicted to contribute strongly (caspase-6), moderately (Beclin-1), or weakly (RIP1) to apoptosis in BT-20 cells. Based on the VIP plot and loadings projections, caspase-6 is predicted to be a strong driver of the apoptotic response in BT-20 and MDA-MB-453 cells, but not MCF7 cells; Beclin-1 is predicted to be moderately antiapoptotic in BT-20 cells but has no role in the other cell lines; and RIP1 is predicted to be weakly antiapoptotic in BT-20 and MDA-MB-453 cells but strongly antiapoptotic in MCF7 cells. As shown in FIG. 13, these cell type dependences were confirmed using siRNA and the relative magnitude of the effect of each target on the apoptotic response was confirmed following various combinations of erlotinib and/or doxorubicin. Importantly, although caspase-6 contributed strongly to cell death in BT-20 cells, caspase-8 remained the strongest predictor. None of the other targets tested modulated the apoptotic response to the same extent as caspase-8, further highlighting its importance. Thus, the increased cell killing by ERL→DOX treatment in BT-20 cells appears to involve rewiring of the DNA damage response, allowing activation of both cell-intrinsic and extrinsic apoptotic programs to contribute to cell death.

Figures 7A, 7B, 7C, 7D:
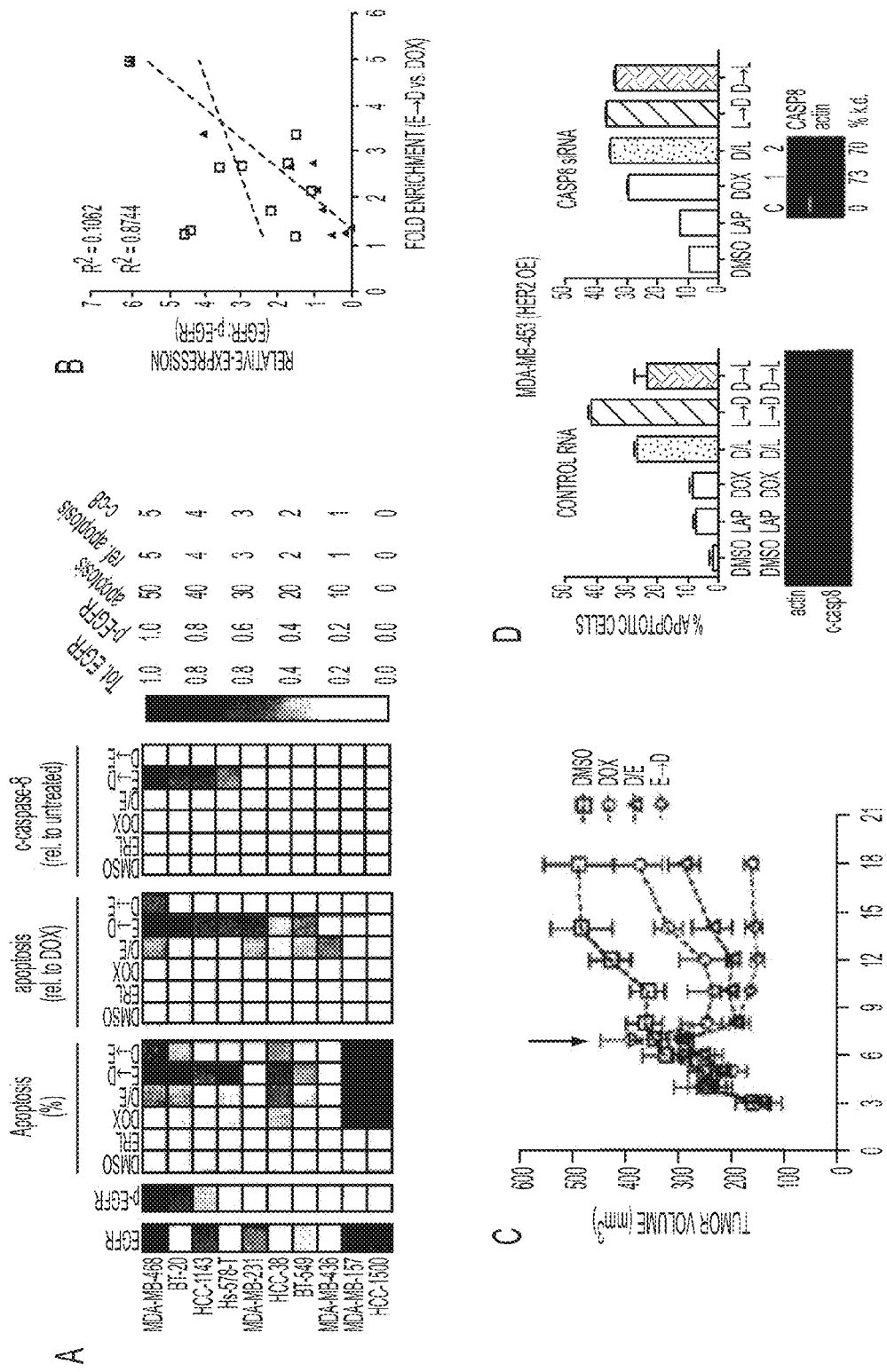
Figure 14A:
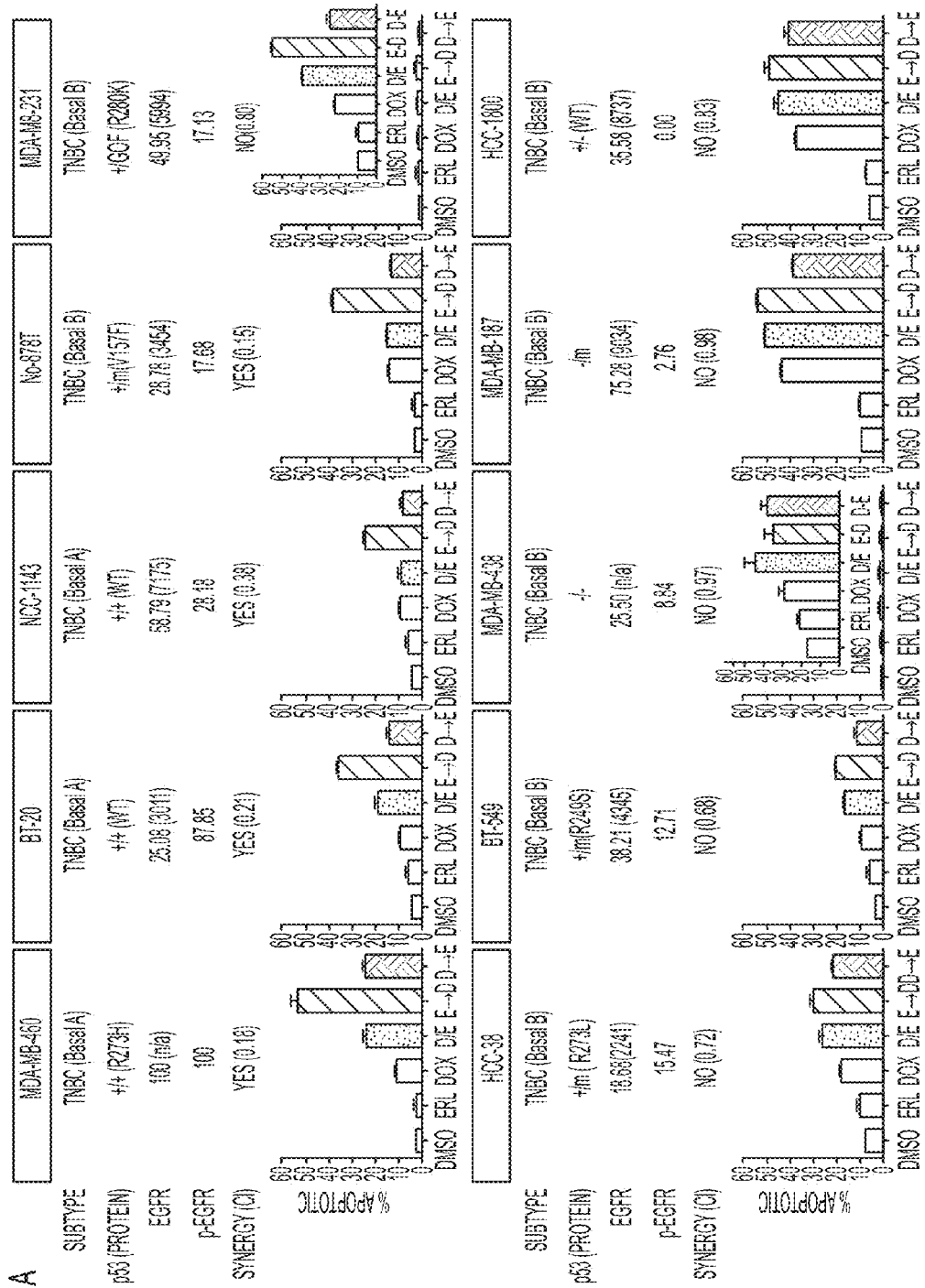

Time-Staggered Inhibition of EGFR Enhances Apoptotic Response in a Subset of TNBC Cells and Other Oncogene-Driven Cells To examine whether the efficacy of time-staggered ERL→DOX treatment was unique to BT-20 cells or potentially a more general phenomenon of TNBC cells, other triple-negative cell lines (Neve et al., 2006) were examined. The selected cell lines have markedly different growth rates, EGFR expression levels, and p53 states (FIG. 14A). Despite these differences, sustained EGFR inhibition enhanced sensitivity to doxorubicin in nine of ten triple-negative cell lines tested. A synergistic effect, however, was observed in only four of the ten TNBC lines (FIGS. 14A, 14A, and 14 B). To identify potential reasons for this, total EGFR protein levels and basal EGFR activation were measure d by immunoblotting. The quantitative measurement of EGFR protein expression was very similar to previously reported values (Neve et al., 2006) and correlated only very weakly with sensitivity to ERL→.DOX treatment (FIGS. 14 A and 14B). In marked contrast, the levels of basal EGFR activity exhibited a much higher correlation (FIGS. 7A and 7B). Furthermore, in those TNBC cell lines in which ERL→DOX treatment was synergistic, it was consistently observed caspase-8 cleavage following sequential administration, but not other drug treatments, suggesting a similar mechanism of enhanced apoptosis in these cells as that observed in BT-20 cells (FIGS. 7A and 7B). Taken in context with the observation that EGFR signaling drives expression of an oncogenic gene expression signature in BT-20 cells, these findings suggest that a subset of triple-negative cell lines are similarly driven by aberrant EGFR signaling. Importantly, however, these cells could not be distinguished by measuring EGFR gene amplification or EGFR abundance. Instead, they are unique in displaying high levels of activated (phosphorylated) EGFR as a biomarker of response to time-staggered EGFR inhibition and cytotoxic treatment.

It was then determined whether the initial chemosensitizing effects of an ERL→DOX protocol could be observed when treating EGFR-driven triple-negative tumors in vivo. BT-20 cells were injected into the flanks of nude mice, and tumors were allowed to form for 7 days before treatment with either doxorubicin alone or erlotinib-doxorubicin combinations. Following single dose of doxorubicin alone, a marked reduction in tumor volume was observed over the first 3 days after treatment. The residual tumors continued to grow, however, reaching pretreatment volume after 14 days (FIG. 7C). A similar trend was observed for tumors cotreated with erlotinib and doxorubicin, although the initial reduction in tumor size was greater. In contrast, when mice were given erlotinib 8 hr prior to doxorubicin, the tumors not only exhibited a similar initial reduction in size, but also failed to regrow throughout the 14 day monitoring period. Thus, the chemosensitizing effect of sequential ERL DOX treatment seen in culture was also observed in vivo. These results provide evidence that time-staggered inhibition of EGFR, in combination with DNA damaging agents, should be a useful therapeutic strategy for treating a subset of triple-negative tumors, particularly those with high basal levels of phosphorylated EGFR.

The Applicability of Time-Staggered Inhibition to Sensitize Other Breast Cancer Subtypes to Doxorubicin.

Figures 14B, 14C, 14D:
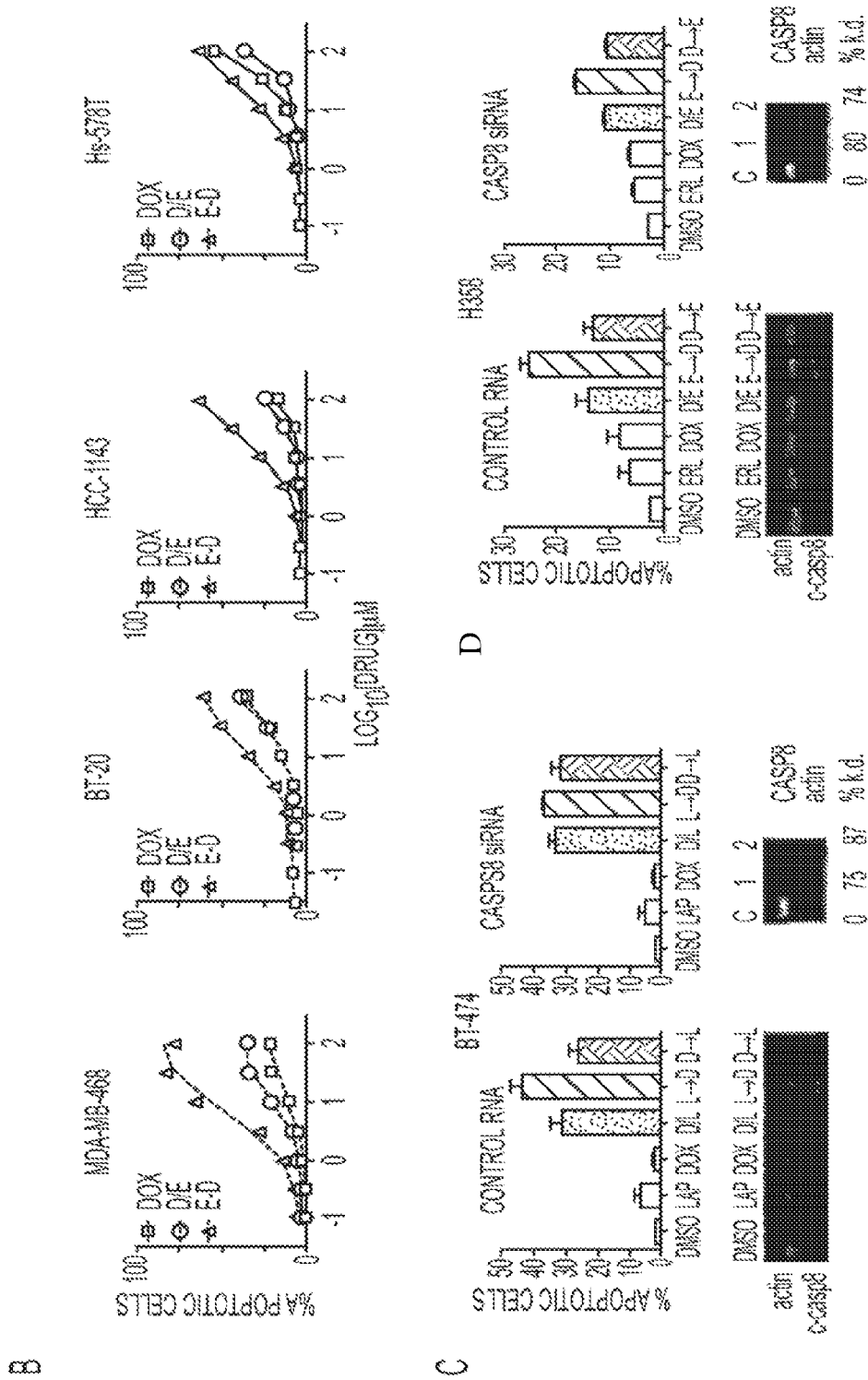

In contrast to BT-20 MDA-MB-453 cells were not sensitized by sustained EGFR inhibition but instead were desensitized to DNA-damaging chemotherapy (FIG. 1D). However, MDA-MB-453- and other widely used cell lines like BT-474 have a well-established oncogene addiction to HER2 (Neve et al., 2006). Time-staggered inhibition of HER2 was therefore testing using the drug lapatinib (a potent inhibitor of both EGFR and HER2) in combination with doxorubicin in these cells. In both MDA-MB-453 and BT-474 cells, in contrast to the desensitization caused by pretreatment with erlotinib, it was observed that lapatinib pretreatment enhanced sensitivity to doxorubicin to a similar extent as the enhancement observed with erlotinib in BT-20 and other EGFR-driven TNBC cells (FIGS. 7C and 14C). Importantly, whereas all temporal combinations of lapatinib and doxorubicin were synergistic in HER2-overexpressing cells, pretreatment with lapatinib resulted in the largest increase in apoptosis. Furthermore, caspase-8 cleavage was only observed following LAP→DOX treatment of HER2-driven cells, but not by other drug combinations. Knockdown of caspase-8 in these cells eliminated the specific component of enhanced cell death observed only in the pretreatment condition (FIGS. 7C and 14C), suggesting that this portion of the overall cell death was driven by caspase-8 activity.

Figures 7E, 7F, 7G:
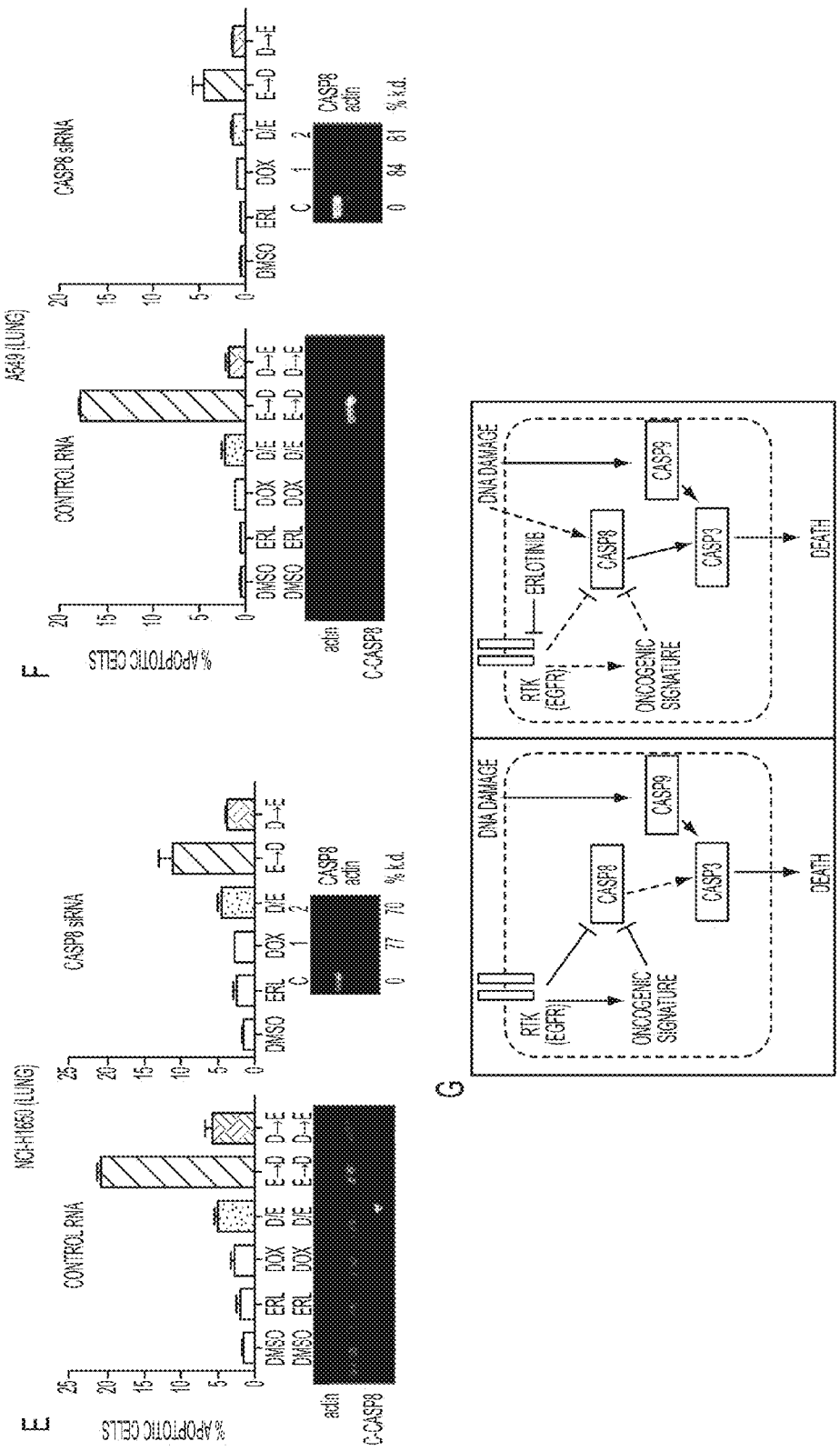

Finally, whether the efficacy of time-staggered inhibition of EGFR was limited to breast cancer cells was tested. Many lung cancers, for example, contain either high levels of phosphorylated wild-type EGFR or mutations within EGFR itself. The ERL→DOX treatment protocol was tested on NCI-H1650 cells, a lung cancer cell that contains an in-frame deletion that is commonly seen in lung cancers (Sardella, A., Bell, D. W., Haber, D. A., and Settleman, J. (2004). Gefitinib-sensitizing EGFR mutations in lung cancer activate antiapoptotic pathways. Science 305, 1163-1167), as well as on A549 and NCI-H358, cells that have high levels of phosphorylated wild-type EGFR, possibly due to HER2 amplification (Balko, J. M., Patti, A., Saunders, C., Stromberg, A., Haura, E. B., and Black, E. P. (2006). Gene expression patterns that predict sensitivity to epidermal growth factor receptor tyrosine kinase inhibitors in lung cancer cell lines and human lung tumors. BMC Genomics 7, 289; Diaz, A., Nguewa, P. A., Parrondo, A. Perez-Stable, C., Manrique, Redrado, M., Catena, A., Collantes, M., Peiiuelas, 1., Diaz-Gonzalez. J. A., and Calvo, A. (2010). Antitumor and antiangiogenic effect of the dual EGFA and HEA-2 tyro-sine kinase inhibitor lapatinib in a lung cancer model. BMC Cancer 10, 188; Helfrich, B. A., Raben, D., Varella-Garcia, M., Gustafson, D., Chan, D. C., Bemis, L., Coldren, C., Baron, A., Zeng, C., Franklin, W. A., et al. (2006). Antitumor activity of the epidermal growth factor receptor (EGFR) tyrosine kinase inhibitor gelitinib (ZD1839, lressa) in non-small cell lung cancer cell lines correlates with gene copy number and EGFR mutations but not EGFR protein levels. Clin. Cancer Res. 12, 7117-7125; Rusnak, D. W., Alligood, K. J., Mullin, A. J., Spehar, G. M., Arenas-Elliott, C., Martin, A. M.•Degenhardt, Y. •Rudolph, S. K., Haws, T. F., Jr., Hudson-Curtis, B. L., and Gilmer, T. M. (2007). Assessment of epidermal growth factor receptor (EGFR, ErbB1) and HER2 (Erb82) protein expression levels and response to lapatinib (Tykerb, GW572016) in an expanded panel of human normal and tumour cell lines. Cell Prolif. 40, 580-594). Remarkably, in all three lung cancer cell lines, it was found that time-staggered inhibition of EGFR using erlotinib caused a dramatic sensitization to killing by doxorubicin that was associated with caspase-8 cleavage (FIGS. 7E, 7F, and 14D). Furthermore, knockdown of caspase-8 largely abrogated the enhanced cell death observed in the pretreatment condition, exactly as was seen in the setting of TNBCs. Thus, time-staggered inhibition of EGFR in cells with highly active EGFR signaling may be a generalizable approach to potentiate the effects of DNA damaging chemotherapy.

A systematic time- and dose-dependent approach to identifying drug combinations that are efficacious in killing cancer cells, depending on changes in the order and duration of drug exposure, has been developed. It was found that EGFR inhibition dramatically sensitizes a subset of TNBCs to DNA damage if the drugs are given sequentially, but not simultaneously. Furthermore, the transcriptional, proteomic, and computational analyses of signaling networks and phenotypes in drug-treated cells revealed that the enhanced treatment efficacy results from dynamic network rewiring of an oncogenic signature maintained by active EGFR signaling to unmask an apoptotic process that involves activation of caspase-8. The enhanced sensitivity to damaging agents that was observed required sustained inhibition of EGFR because the phenotype did not result from the rapid, direct inhibition of the oncogene but, rather, from modulation of an oncogene-driven transcriptional network as indicated schematically in the model shown in FIG. 7G. Furthermore, the data indicate that it is activity of the EGFR pathway, rather than EGFR expression per se, that determines whether time-staggered inhibition will result in synergistic killing. Because EGFR can be activated through a diverse set of genetic alterations, some of which do not necessarily include EGFR itself (Sun, T., Aceto, N., Meerbrey, K. L., Kessler, J. D., Zhou, C. Migliaccio, 1., Nguyen, D. X., Pavlova, N, N., Botero, M., Huang, J., et al. (2011). Activation of multiple proto-oncogenic tyrosine kinases in breast cancer via loss of the PTPN12 phosphatase. *Cell* 144, 703-718), these findings highlight the need to understand network connectivity and dynamics (Pawson, T., and Linding, A. (2008). Network medicine. FEBS Lett. 582, 1266-1270). Conversely, these observations indicate that EGFR phosphorylation is a useful biomarker of response to time-staggered inhibition in at least some tumor types that are EGFR driven, including some TNBCs and lung cancers.

A key consequence of the erlotinib-dependent dynamic remodeling of the DDR network is activation of caspase-8 following DNA damage. The mechanism of caspase-8 activation is unclear because it is generally thought to be specific to receptor-mediated apoptosis triggered by ligands such as the tumor necrosis factor (TNF) and TNF-related apoptosis-inducing ligand (TRAIL). Possibilities include feedback activation by caspase-3, possibly involving caspase-6 (Albeck, J. G., Burke, J. M.•Spencer, S. L., Lauffenburger, D. A., and Sorger, P. K. (2008). Modeling a snap-action, variable-delay switch controlling extrinsic cell death. PLoS Bioi. 6, 2831-2852); direct activation of death receptors by DDR proteins (Yoon, C. H., Kim, M. J., Park, M. T., Byun, J. Y., Choi, Y. H., Yoo, H. S., Lee, Y. M., Hyun, J W., and Lee, S. J. (2009). Activation of p38 mitogen-activated protein kinase is required for death receptor-independent caspase-8 activation and cell death in response to sphingosine. Mol. Cancer. Res. 7, 361-370); or an autocrine/paracrine mechanism involving an as-yet unidentified death ligand.

Those skilled in the art will recognize, or be able to ascertain using no more than routine experimentation, many equivalents to the specific embodiments of the invention described herein. Such equivalents are intended to be encompassed by the following claims.

We claim:

1. A method for treating a cancer in a subject in need thereof, wherein the cancer is resistant to a DNA-damaging chemotherapeutic agent, the method comprising:
   administering to the patient an effective amount of a pharmaceutical composition comprising a liposome in a pharmaceutically effective excipient,
   wherein the liposome includes an aqueous interior layer and a lipophilic exterior layer, the lipophilic exterior layer including a hydrophobic inhibitor of an EGFR pathway, and the aqueous interior layer including a hydrophilic DNA-damaging chemotherapeutic agent,
   wherein the pharmaceutical composition further comprises a controlled release excipient, and wherein a therapeutically effective amount of the EGFR inhibitor is released at the time of administration, and a therapeutically effective amount of the DNA damaging agent is released at least four hours later.

2. The method of claim 1, wherein the therapeutically effective amount of the EGFR inhibitor is released at the time of administration, and the therapeutically effective amount of the DNA damaging agent is released at least eight hours later.

3. The method of claim 1 wherein the EGFR pathway inhibitor includes at least one compound selected from the group consisting of:

Erlotinib, gefitinbib, herceptin, tarceva;
Sunitinib;
Imatinib;
Bevacizumab;
Sorafenib;
BEZ-235;
Torin, rapamycin;
PD98059;
SB203580;
Wortmannin, LY294002;
PF-3758309;
BIBF1120, Ponatinib; and
SP600125.

4. The method of claim 1 wherein the DNA damaging agent includes at least one compound selected from the group consisting of: daunomycin, arugamycin, epirubicin, idarubicin, Dynemycin, Adriamycin, cyclophosphamide, Taxotere, bleomycin, vinblastine, dacarbazine, vincristine, prednisone, 5-fluorouracil, camptothecin, topotecan, irinotecan, BCNU, carmustine, and cis-platin.

5. The method of claim 1 wherein the cancer is breast cancer.

6. The method of claim 5 wherein the cancer is triple negative breast cancer.

7. The method of claim 1 wherein the cancer is a lung cancer, and wherein said lung cancer is caused by either a high level of phosphorylation of a wild-type EGFR or a mutations within an EGFR amino acid sequence.

8. A pharmaceutical composition, comprising a liposome in a pharmaceutically effective excipient, wherein the liposome includes:

an aqueous interior layer and a lipophilic exterior layer,
the lipophilic exterior layer including a hydrophobic inhibitor of an EGFR pathway;
the aqueous interior layer including a hydrophilic DNA-damaging chemotherapeutic agent; and
a controlled release excipient,
wherein, when the pharmaceutical composition is administered to a patient in need thereof, a therapeutically effective amount of the EGFR inhibitor is released at the time of administration, and a therapeutically effective amount of the DNA damaging agent is released at least four hours later.

9. The pharmaceutical composition of claim 8, wherein the exterior layer includes an EGFR-targeting moiety.

10. The pharmaceutical composition of claim 8, wherein, when the pharmaceutical composition is administered to a patient in need thereof, the therapeutically effective amount of the EGFR inhibitor is released at the time of administration, and the therapeutically effective amount of the DNA damaging agent is released at least eight hours later.

* * * * *

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: sense for EGFR

<400> SEQUENCE: 1
gaucuuuccu ucuuaaagat t                                         21

<210> SEQ ID NO 2
<211> LENGTH: 21

```
<212> TYPE: DNA
<213> ORGANISM: Artificial Sequence
<220> FEATURE:
<223> OTHER INFORMATION: antisense for EGFR

<400> SEQUENCE: 2
ucuuuaagaa ggaaagauca t                                      21

<210> SEQ ID NO 3
<211> LENGTH: 21
<212> TYPE: DNA
<213> ORGANISM: Artificial Sequence
<220> FEATURE:
<223> OTHER INFORMATION: sense for EGFR

<400> SEQUENCE: 3
ccauaaaugc uacgaauaut t                                      21

<210> SEQ ID NO 4
<211> LENGTH: 21
<212> TYPE: DNA
<213> ORGANISM: Artificial Sequence
<220> FEATURE:
<223> OTHER INFORMATION: antisense for EGFR

<400> SEQUENCE: 4
auauucguag cauuuaugga g                                      21

<210> SEQ ID NO 5
<211> LENGTH: 21
<212> TYPE: DNA
<213> ORGANISM: Artificial Sequence
<220> FEATURE:
<223> OTHER INFORMATION: sense for caspse-8

<400> SEQUENCE: 5
gauacugucu gaucaucaat t                                      21

<210> SEQ ID NO 6
<211> LENGTH: 21
<212> TYPE: DNA
<213> ORGANISM: Artificial Sequence
<220> FEATURE:
<223> OTHER INFORMATION: antisense for caspase-8

<400> SEQUENCE: 6
uugaugauca gacaguaucc c                                      21

<210> SEQ ID NO 7
<211> LENGTH: 21
<212> TYPE: DNA
<213> ORGANISM: Artificial Sequence
<220> FEATURE:
<223> OTHER INFORMATION: sense for caspase-8

<400> SEQUENCE: 7
gaucagaauu gaggucuuut t                                      21

<210> SEQ ID NO 8
<211> LENGTH: 21
<212> TYPE: DNA
<213> ORGANISM: Artificial Sequence
<220> FEATURE:
<223> OTHER INFORMATION: antisense for caspase-8

<400> SEQUENCE: 8
```

-continued aaagaccuca auucugauct g                    21

<210> SEQ ID NO 9
<211> LENGTH: 21
<212> TYPE: DNA
<213> ORGANISM: Artificial Sequence
<220> FEATURE:
<223> OTHER INFORMATION: sense for caspase-6

<400> SEQUENCE: 9
ggcuccuccu uagaguugat t                    21

<210> SEQ ID NO 10
<211> LENGTH: 21
<212> TYPE: DNA
<213> ORGANISM: Artificial Sequence
<220> FEATURE:
<223> OTHER INFORMATION: antisense for caspase-6

<400> SEQUENCE: 10
ugaacucuaa ggaggagcca t                    21

<210> SEQ ID NO 11
<211> LENGTH: 20
<212> TYPE: DNA
<213> ORGANISM: Artificial Sequence
<220> FEATURE:
<223> OTHER INFORMATION: sense for caspase-6

<400> SEQUENCE: 11
gcaucacauu uaugcauatt                      20

<210> SEQ ID NO 12
<211> LENGTH: 21
<212> TYPE: DNA
<213> ORGANISM: Artificial Sequence
<220> FEATURE:
<223> OTHER INFORMATION: antisense for caspase-6

<400> SEQUENCE: 12
uaugcauaaa ugugauugcc t                    21

<210> SEQ ID NO 13
<211> LENGTH: 21
<212> TYPE: DNA
<213> ORGANISM: Artificial Sequence
<220> FEATURE:
<223> OTHER INFORMATION: sense for Beclin1

<400> SEQUENCE: 13
caguuacaga uggagcuaat t                    21

<210> SEQ ID NO 14
<211> LENGTH: 21
<212> TYPE: DNA
<213> ORGANISM: Artificial Sequence
<220> FEATURE:
<223> OTHER INFORMATION: antisense for Beclin1

<400> SEQUENCE: 14
uuagcuccau cuguaacugt t                    21

<210> SEQ ID NO 15
<211> LENGTH: 21
<212> TYPE: DNA
<213> ORGANISM: Artificial Sequence

```
<220> FEATURE:
<223> OTHER INFORMATION: sense for Beclin1

<400> SEQUENCE: 15
gcaguugaaa gaagagguut t                                              21

<210> SEQ ID NO 16
<211> LENGTH: 21
<212> TYPE: DNA
<213> ORGANISM: Artificial Sequence
<220> FEATURE:
<223> OTHER INFORMATION: antisense for Beclin1

<400> SEQUENCE: 16
aaccucuucu uugaacugct g                                              21

<210> SEQ ID NO 17
<211> LENGTH: 21
<212> TYPE: DNA
<213> ORGANISM: Artificial Sequence
<220> FEATURE:
<223> OTHER INFORMATION: sense for RIP1

<400> SEQUENCE: 17
ccacuagucu gacggauaat t                                              21

<210> SEQ ID NO 18
<211> LENGTH: 21
<212> TYPE: DNA
<213> ORGANISM: Artificial Sequence
<220> FEATURE:
<223> OTHER INFORMATION: antisense for RIP1

<400> SEQUENCE: 18
uuauccguca gacuaguggt a                                              21

<210> SEQ ID NO 19
<211> LENGTH: 22
<212> TYPE: DNA
<213> ORGANISM: Artificial Sequence
<220> FEATURE:
<223> OTHER INFORMATION: sense for RIP1

<400> SEQUENCE: 19
gcaaagaccu uacgagaauu tt                                             22

<210> SEQ ID NO 20
<211> LENGTH: 21
<212> TYPE: DNA
<213> ORGANISM: Artificial Sequence
<220> FEATURE:
<223> OTHER INFORMATION: antisense for RIP1

<400> SEQUENCE: 20
auucucguaa ggucuuugct g                                              21
```